(12) United States Patent
Thomas et al.

(10) Patent No.: US 8,759,031 B2
(45) Date of Patent: Jun. 24, 2014

(54) TYPE I POLYKETIDE SYNTHASE EXTENDER UNITS

(75) Inventors: Michael G. Thomas, Madison, WI (US); Jo Handelsman, Madison, WI (US); Yolande Alia Chan, Madison, WI (US); Angela M. Podevels, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1208 days.

(21) Appl. No.: 12/100,150

(22) Filed: Apr. 9, 2008

(65) Prior Publication Data

US 2008/0254508 A1 Oct. 16, 2008

Related U.S. Application Data

(60) Provisional application No. 60/923,105, filed on Apr. 12, 2007.

(51) Int. Cl.
*C12P 19/62* (2006.01)
*C12N 9/10* (2006.01)

(52) U.S. Cl.
USPC ............................................. 435/76; 435/193

(58) Field of Classification Search
None
See application file for complete search history.

(56) References Cited

U.S. PATENT DOCUMENTS

| | | | |
|---|---|---|---|
| 4,874,784 A | 10/1989 | Smith et al. | |
| 5,063,155 A | 11/1991 | Cox et al. | |
| 5,098,837 A | 3/1992 | Beckmann et al. | |
| 5,149,639 A | 9/1992 | Katz et al. | |
| 5,672,491 A | 9/1997 | Khosla et al. | |
| 5,712,146 A | 1/1998 | Khosla et al. | |
| 5,830,750 A | 11/1998 | Khosla et al. | |
| 5,843,718 A | 12/1998 | Khosla et al. | |
| 6,274,560 B1 | 8/2001 | Khosla et al. | |
| 6,531,299 B1 | 3/2003 | Khosla et al. | |
| 6,551,802 B2 | 4/2003 | Khosla et al. | |
| 6,660,862 B2 | 12/2003 | Reeves et al. | |
| 6,750,040 B1 | 6/2004 | Khosla et al. | |
| 6,753,173 B1 | 6/2004 | Gokhale et al. | |
| 6,939,691 B1 | 9/2005 | Khosla et al. | |
| 7,101,684 B2 | 9/2006 | Khosla et al. | |
| 2005/0089982 A1* | 4/2005 | Leadlay et al. | 435/193 |

FOREIGN PATENT DOCUMENTS

| | | | |
|---|---|---|---|
| EP | 1493814 | * | 1/2005 |
| WO | WO 93/13663 | | 7/1993 |
| WO | WO 95/08548 | | 3/1995 |
| WO | WO 96/40968 | | 12/1996 |
| WO | WO 97/02358 | | 1/1997 |
| WO | WO 98/27203 | | 6/1998 |
| WO | WO 98/49315 | | 11/1998 |
| WO | WO/00/58351 | * | 10/2000 |

OTHER PUBLICATIONS

Polyketide synthases (last viewed on Sep. 13, 2011).*
Kevany et al., Characterization of the Complete Zwittermicin A biosynthesis Gene Cluster from *Bacillus cereus*., Applied and Environmental Microbiology, Feb. 2009, vol. 75, pp. 1144-1155.*

(Continued)

*Primary Examiner* — Alexander Kim
(74) *Attorney, Agent, or Firm* — Quarles & Brady LLP

(57) ABSTRACT

Novel extender units for Type I polyketide synthases are provided. Also provided are genes, compounds, and methods for generating these units, and for incorporation of the novel extender units into polyketides for the purpose of generating new structural derivatives of polyketide-containing products.

10 Claims, 14 Drawing Sheets

(56) References Cited

OTHER PUBLICATIONS

Guo et al., Protein tolerance to random amino acid change, 2004, Proc. Natl. Acad. Sci. USA 101: 9205-9210.*
Lazar et al., Transforming Growth Factor α: Mutation of Aspartic Acid 47 and Leucine 48 Results in Different Biological Activity, 1988, Mol. Cell. Biol. 8:1247-1252.*
Hill et al., Functional Analysis of conserved Histidines in ADP-Glucose Pyrophosphorylase from *Escherichia coli*, 1998, Biochem. Biophys. Res. Comm. 244:573-577.*
Wacey et al., Disentangling the perturbational effects of amino acid substitutions in the DNA-binding domain of p53., Hum Genet, 1999, vol. 104, pp. 15-22.*
Manning et al., Structural Basis of Protein Kinetic Stability: Resistance to Sodium Dodecyl Sulfate Suggests a Central Role for Rigidity and a Bias Toward β-Sheet Structure, Biochemistry, 2004, vol. 43, pp. 11248-11254.*
Wiesmann et al., Polyketide synthesis in vitro on a modular polyketide synthase., Chemistry & Biology, (1995) vol. 2, pp. 583-589.*
Leadlay Research Group (last viewed on Jan. 6, 2009).*
Leadlay, Combinatorial approaches to polyketide biosynthesis, Current Opinion in Chemical Biology, (1997), vol. 1, pp. 162-168.*
Cheng et al., Type I polyketide synthase requirring a discrete acyltransferase for polyketide biosynthesis., PNAS (2003), vol. 100, pp. 3149-3154.*
*Advanced Organic Chemistry: Reactions, Mechanisms and Structure*, 4th Ed., Wiley-Interscience, New York, Mar. 1992.
Altschul et al., "Gapped BLAST and PSI-BLAST: A New Generation of Protein Dtatabase Search Programs," *Nucl. Acids Res.* 25(17):3389-3402 (1997).
Ausubel et al., *Current Protocols in Molecular Biology*, vols. 1-3, John Wiley & Sons, Inc. (1993).
Brunker et al., "Genetic Engineering of an Industrial Strain of *Saccharopolyspora erythraea* for Stable expression of the *Vitreoscilla* Haemoglobin Gene (vhb)", *Microbiology* 144: 2441-2448 (1998).
Caffrey et al., "Identification of DEBS 1, DEBS 2, and DEBS 3, the Multienzyme Polypeptides of the Erythromycin-Producing Polyketide Synthase From *Saccharopolyspora etythraea*," *FEBS Lett.* 304(2,3):225-228 (1992).
Carroll et al., "Identification of a Set of Genes Involved in the Formation of the Substrate for the Incorporation of the Unusual 'Glycolate' Chain Extension Unit in Ansomitocin Biosynthesis," *J. Am. Chem. Soc.*, 124:4176-4177 (2002).
Chan et al., "Hydroxymalonyl-acyl Carrier Protein (ACP) and Aminomalonyl-ACP are Two Additional Type I Polyketide Synthase Extender Units," *Proc. Natl. Acad. Sci., U.S.A.* 103 (39):14349-14354 (2006).
Donadio et al., "Modular Organization of Genes Required for Complex Polyketide Biosynthesis," *Science* 252:675-679 (1991).
Dorrestein et al., "Facile Detection of Acyl and Peptidyl Intermediates on Thiotemplate Carrier Domains via Phosphopantetheinyl Elimination Reactions During Tandem Mass Spectrometry," *Biochemistry*, 45:12756-12766 (2006).
Emmert et al., "Genetics of Zwittermicin A Production by *Bacillus cereus*," *Appl. Environ. Microbiol.*, 70:104-113 (2004).
Falzari et al., "In Vitro and In Vivo Activities of Macrolide Derivatives against *Mycobacterium tuberculosis*," *Antimicrob. Agents Chemother*, 49(4):1447-1454 (2004).
Fu et al., "Engineered Biosynthesis of Novel Polyketides: Stereochemical Course of Two Reactions Catalyzed by a Polyketide Synthase," *Biochemistry*, 33:9321-9326 (1994).
Hans et al., "Mechanistic Analysis of Acyl Transferase Domain Exchange in Polyketide synthase Modules," *J. Am. Chem. Soc.*, 125:5366-5374 (2003).
Kao el al., "Engineered Biosynthesis of a Complete Macrolactone in a Heterologous Host," *Science* 265:509-512 (1994).
Karlin and Altschul, "Methods for Assessing the Statistical Significance of Molecular Sequence Features by Using General Scoring Schemes," *Proc. Natl. Acad. Sci. USA*, 87:2264-2268 (1990).
Kriegler, *Gene Transfer and Expression: A Laboratory Manual*, Stockton Press, New York (1990).
McDaniel et al., "Multiple Genetic Modifications of the Erythromycin Polyketide Synthase to Produce a Library of Novel 'Unnatural' Natural Products," *Proc. Natl. Acad. Sci. USA*, 96:1846-1851 (1999).
McDaniel et al., "Engineered Biosynthesis of Novel Polyketides," *Science*, 262:1546-550 (1993).
MacNeil et al., "Complex Organization of the *Streptomyces avermitilis* Genes Encoding the Avermectin Polyketide Synthase," *Gene*, 115:119-125 (1992).
Menzella et al., "Combinatorial Polyketide Biosynthesis by de novo Design and Rearrangement of Modular Polyketide Synthase Genes," *Nature Biotech.*, 23:1171-1176 (2005).
Overman, *Organic Reactions*, vol. 66, John Wiley & Sons, Inc. (2005).
Pearson and Lipman, "Improved Tools for Biological Sequence Comparison," *Proc. Natl. Acad. Sci. USA.*, 85:2444-2448 (1988).
Pieper et al., "Cell-Free Synthesis of Polyketides by Recombinant Erythromycin Polyketide Synthases," *Nature*, 378:263-266 (1995).
Quadri et al., "Characterization of Sfp, a *Bacillus subtilis* Phosphopantetheinyl Transferase for Peptidyl Carrier Protein Domains in Peptide Synthetases," *Biochemistry*, 37:1585-1595 (1998).
Rohr, "Combinatorial Biosynthesis—An Approach in the New Future?" *Angew. Chem. Int. Ed. Engl.*, 34:881-888 (1995).
Sambrook et al., *Molecular Cloning—A Laboratory Manual*, Cold Spring Harbor Laboratory, Cold Spring Harbor, New York (1989).
Smith and Waterman, "Comparison of Biosequences," *Adv. Appl. Math.*, 2:482-489 (1981).
Taylor et al., "Web and Database Software for Identification of Intact Proteins Using 'Top Down' Mass Spectrometry," *Anal. Chem.*, 75:4081-4086 (2003).
Thomas et al., "Conversion of L-Proline to Pyrrolyl-2-Carboxyl-S-PCP During Undecylprodigiosin and Pyoluteorin Biosynthesis," *Chem. Biol.*, 9:171-184 (2002).
Watanabe et al., "Total Biosynthesis of Antitumor Nonribosomal Peptides in *Escherichia coli*," *Nat. Chem. Biol.*, 2:423-428 (2006).
Wilkinson et al., "Novel Octaketide Macrolides Related to 6-Deoxyerythronolide B Provide Evidence for Iterative Operation of the Erythromycin Polyketide Synthase," *Chem. Biol.*, 7:111-117 (2000).
Wu et al., The FK520 Gene Clust of *Streptomyces hygroscopicus* var. *ascomyceticus* (ATCC 14891) Contains Genes for Biosynthesis of Unusual Polyketide Extender Units, Gene, 251:81-90 (2000).

\* cited by examiner

SEQUENCE LISTING

```
<160> NUMBER OF SEQ ID NOS: 14

<210> SEQ ID NO 1
<211> LENGTH: 359
<212> TYPE: PRT
<213> ORGANISM: Bacillus cereus

<400> SEQUENCE: 1

Met Ser Lys Glu Ile Lys Cys Val Val Trp Asp Leu Asp Cys Thr Ile
1               5                   10                  15

Trp Asp Gly Val Leu Leu Glu Ser Gly Thr Val Thr Leu Lys Pro Gly
                20                  25                  30

Ile Tyr Glu Ile Ile Cys Glu Leu Asp Arg Arg Gly Ile Leu Gln Ser
            35                  40                  45

Val Ala Ser Lys Asn Asn Tyr Glu Asp Ala Ile Ala Lys Leu Arg Glu
        50                  55                  60

Phe Gly Ile Glu Glu Tyr Phe Leu Tyr Pro Glu Ile His Trp Asn Ser
65                  70                  75                  80

Lys Ser Ser Ser Ile Glu Lys Ile Arg Lys Asn Leu Asn Ile Gly Ile
                85                  90                  95

Asp Thr Phe Ala Phe Ile Asp Asp Gln Pro Phe Glu Leu Glu Glu Val
                100                 105                 110

Gln Ser Val His Asn Asp Ile Leu Cys Ile His Val Asn Glu Tyr Lys
            115                 120                 125

Ser Leu Leu Asp Leu Pro Arg Leu Gln Pro Lys Arg Ile Thr Glu Asp
        130                 135                 140

Ser Gly Arg Arg Arg Leu Met Tyr Leu Glu Asn Leu Lys Arg Thr Lys
145                 150                 155                 160

Asp Glu Glu Glu Tyr Glu Gly Pro Lys Glu Glu Phe Leu Ala Ser Leu
                165                 170                 175
```

-continued

```
Gly Met Asn Phe Val Ile Ser Glu Ala Arg Glu Glu Asp Leu Gln Arg
            180                 185                 190

Ala Glu Glu Leu Thr Val Arg Thr Asn Gln Leu Asn Ser Thr Gly Ile
        195                 200                 205

Thr Tyr Asp Tyr Asp Glu Leu Asn Tyr Tyr Arg Asn His Pro Asp Tyr
    210                 215                 220

Leu Leu Leu Val Cys Glu Leu Ser Asp Lys Tyr Gly Ser Tyr Gly Lys
225                 230                 235                 240

Ile Gly Leu Thr Leu Val Lys Arg Thr Glu Glu Ala Asp Cys Leu Lys
                245                 250                 255

Leu Leu Leu Met Ser Cys Arg Val Met Ser Arg Gly Val Gly Thr Ile
            260                 265                 270

Leu Leu Thr Tyr Leu Met Glu Arg Thr Lys Gln Ala Gly Lys Arg Phe
        275                 280                 285

Leu Ala Glu Phe Arg Gln Thr Asp Arg Asn Arg Met Met Phe Val Thr
    290                 295                 300

Tyr Arg Leu Ala Gly Phe Lys Glu Thr Ser Asn Glu Asn Gly Ile Leu
305                 310                 315                 320

Ile Leu Glu His Asn Leu Glu Asn Ile Asn Pro Tyr Pro His Tyr Ile
                325                 330                 335

Asn Ile Gln Phe Pro Glu Thr Pro Thr Asp Val Asp Arg Gly Glu Val
            340                 345                 350

Glu Ile Cys Asn Lys Gln Leu
        355

<210> SEQ ID NO 2
<211> LENGTH: 87
<212> TYPE: PRT
<213> ORGANISM: Bacillus cereus

<400> SEQUENCE: 2

Met Asp Asn His Glu Lys Ile Arg Gln Tyr Ile Lys Lys Asn Leu Ile
1               5                   10                  15

Ile Phe Asn Ala Glu Glu Thr Ile Val Ala Asn Asp Glu Asn Ile Phe
            20                  25                  30

Glu Lys Gly Tyr Val Asn Ser Leu Phe Ala Met Gln Met Leu Asn Phe
        35                  40                  45

Ile Glu Thr Glu Phe Asp Ile Val Val Asp Asn Asp Glu Leu Asp Ile
    50                  55                  60

Ile Asn Phe Ser Thr Ile Asn Asn Met Val Asp Leu Ile Asn Lys Lys
65                  70                  75                  80

Lys Asn Gly Asn Phe Thr Val
                85

<210> SEQ ID NO 3
<211> LENGTH: 382
<212> TYPE: PRT
<213> ORGANISM: Bacillus cereus

<400> SEQUENCE: 3

Met Ser Asn Ala Glu Glu Ile Leu Gly Val Val Asp Glu Phe Ala Glu
1               5                   10                  15

Lys Lys Leu Arg Pro Arg Ala Ser Glu Phe Glu Ser Asn Glu Glu Leu
            20                  25                  30

Pro Tyr Asp Val Ile Gln Glu Ile Ser Ser Tyr Gly Val Leu Gly Ala
        35                  40                  45
```

```
Thr Ile Pro Lys Glu Tyr Gly Gly Leu Ser Leu Asp Ser Leu Asp Tyr
     50                  55                  60
Gly Arg Leu Thr Glu Ile Ile Gly Lys Ala Cys Asn Ser Val Arg Glu
 65                  70                  75                  80
Leu Leu Thr Val His Val Ser Leu Val Gly Glu Ser Ile Lys Arg Trp
                     85                  90                  95
Gly Thr Glu Glu Gln Lys Arg Lys Trp Leu Pro Glu Met Ala Lys Gly
                100                 105                 110
Asn Leu Leu Phe Ser Phe Ala Leu Thr Glu Pro Glu Val Gly Ser Asp
            115                 120                 125
Ala Lys Ala Val Gly Thr Ser Tyr Lys Gln Val Asn Asp His Phe Ile
130                 135                 140
Leu Asn Gly His Lys Lys Trp Ile Ser Phe Ala Asp Ile Ala Asp Cys
145                 150                 155                 160
Phe Leu Val Phe Ala Ser Ser Glu Gly Lys Val Ser Ala Phe Ile Val
                    165                 170                 175
Glu Arg Ser Met Thr Gly Val Ser Thr Asn Lys Met Ser Lys Leu Leu
                180                 185                 190
Ala Ser Asn Ser Ser His Ile Ala Glu Ile His Leu Gln Asp Val Lys
            195                 200                 205
Val Pro Ala Glu Asn Leu Leu Gly Pro Ile Gly Gly Trp Ser Tyr
210                 215                 220
Val Val Asn Thr Ala Leu Asp His Gly Arg Tyr Ser Ile Ala Trp Ala
225                 230                 235                 240
Gly Val Ala Ile Ala Gln Glu Ala Leu Glu Ala Met Val Ala Tyr Ser
                    245                 250                 255
Arg Arg Arg Lys Gln Gly Asn Lys Tyr Ile Cys Glu Tyr Glu Ala Ile
                260                 265                 270
Gln Thr Ile Leu Ala Glu Ala Ser Val Asn Ile Lys Ala Ala Arg Ser
            275                 280                 285
Leu Cys Gln Glu Ala Gly Lys Lys Arg Gln Asp Arg Gln Thr Asp Ala
290                 295                 300
Val Ile Glu Thr Thr Ile Ala Lys Tyr Phe Ala Ser Lys Met Ala Met
305                 310                 315                 320
Lys Val Ala Thr Asp Ala Val Gln Val Phe Gly Gly Asn Gly Phe Ser
                325                 330                 335
Arg Glu Tyr Pro Val Glu Arg Leu Phe Arg Glu Ala Lys Val Leu Glu
                340                 345                 350
Ile Ile Glu Gly Thr Ser Gln Val Leu Gln Pro Ile Ile Ala Gln His
            355                 360                 365
Ala Leu Arg Thr Cys Ser Gln Lys Gly Gly Leu Leu Arg Ile
370                 375                 380

<210> SEQ ID NO 4
<211> LENGTH: 282
<212> TYPE: PRT
<213> ORGANISM: Bacillus cereus

<400> SEQUENCE: 4

Met Phe Lys Lys Ile Gly Ile Val Gly Ala Gly Thr Met Gly Ile Gly
 1               5                  10                  15
Met Ala Val Asp Leu Val Leu His Gly Leu Glu Thr Val Leu Ile Asp
             20                  25                  30
Val Thr Glu Glu Gln Leu Glu Lys Ala Glu Glu Lys Ile Leu Glu Thr
         35                  40                  45
```

```
Val Arg Phe Ala Pro Leu Ile Asn Lys Ala Phe Pro Arg Met His Lys
    50                  55                  60

Glu Glu Val Leu Ser Leu Ile Ser Ser Ser Thr Asn Leu Asp Glu Val
65                  70                  75                  80

Ala Glu Cys Asp Tyr Ile Val Glu Asn Val Pro Glu Asn Trp Gln Ile
                85                  90                  95

Lys Glu Pro Ile Tyr Arg Arg Leu Asp Glu Ile Cys Lys Lys Asp Thr
            100                 105                 110

Ile Phe Gly Val Asn Thr Ser Cys Ile Ser Ile Thr Lys Val Gly Gly
        115                 120                 125

Val Thr Lys Arg Pro Asp Lys Ile Ile Gly Met His Phe Met Asn Pro
    130                 135                 140

Val Tyr Met Lys Pro Ser Ile Glu Val Ile Arg Gly His Leu Thr Ser
145                 150                 155                 160

Asp Glu Thr Val Glu Lys Ala Gln Ser Phe Leu Lys Gln Leu Asp Lys
                165                 170                 175

Asp Ala Ile Val Val Asn Asp Gln Thr Gly Phe Val Ser Asn Arg Ile
            180                 185                 190

Ser His Leu Phe Met Asn Glu Ser Ala Trp Val Val Met Asp Gly Val
        195                 200                 205

Ala Thr Pro Lys Gln Val Asp Asp Ile Phe Lys Lys Cys Phe Gly His
    210                 215                 220

Thr Met Gly Pro Leu Glu Thr Ala Asp Leu Ile Gly Leu Asp Thr Val
225                 230                 235                 240

Leu His Ser Leu Asn Val Leu Tyr Glu Glu Tyr Gln Asp Pro Lys Phe
                245                 250                 255

Arg Cys Cys Pro Leu Leu Lys Lys Met Val Asp Ala Gly Glu Cys Gly
            260                 265                 270

Arg Lys Ser Gly Lys Gly Phe Tyr Ala Tyr
        275                 280

<210> SEQ ID NO 5
<211> LENGTH: 3336
<212> TYPE: PRT
<213> ORGANISM: Bacillus cereus

<400> SEQUENCE: 5

Met Lys His Gln Asp Asp Ser Lys Thr Gly Leu Glu Ile Ala Ile Ile
1               5                   10                  15

Gly Met Ala Gly Lys Phe Pro Gly Ala Asn Glu Ile Asn Gln Phe Trp
            20                  25                  30

Asp Asn Leu Lys Asn Gly Val Asp Ser Ile Ser Thr Phe Thr Glu Asp
        35                  40                  45

Glu Leu Ile Lys Glu Gly Val Asn Leu Asp Val Leu Gln His Pro Asn
    50                  55                  60

Phe Val Lys Ala Lys Gly Tyr Leu Glu Glu Val Glu Tyr Phe Asp Glu
65                  70                  75                  80

Ser Phe Phe Ala Tyr Thr Pro Arg Glu Ala Lys Ile Met Asp Pro Gln
                85                  90                  95

Ile Arg Met Leu Gln Glu Thr Thr Trp Glu Ala Leu Glu Met Ala Gly
            100                 105                 110

Tyr Asn Pro Phe Asp Tyr Glu Gly Leu Ile Gly Leu Tyr Val Gly Ala
        115                 120                 125

Ser Thr Asn Phe Asn Trp Met Lys His Thr Pro Leu Leu Asn Ser Asp
```

```
              130                 135                 140
Ser Val Val Glu Phe Ser Glu Ala Gly Thr Leu Ser Tyr Lys Asp Ala
145                 150                 155                 160

Ile Ser Thr Leu Thr Ser Tyr Lys Leu Gly Leu Lys Gly Pro Ser Phe
                    165                 170                 175

Thr Leu Tyr Thr Ala Cys Ser Thr Ser Leu Leu Ser Ile His Leu Ala
                180                 185                 190

Cys Arg Ser Leu Leu Thr Gly Glu Cys Ser Ile Ala Ala Ala Gly Gly
                    195                 200                 205

Val Ser Ile Thr Tyr Pro Lys Lys Asn Gly Tyr Lys Tyr His Glu Gly
                210                 215                 220

Met Thr Ser Ser Pro Asp Gly Lys Val Arg Thr Phe Asp Ala Glu Ala
225                 230                 235                 240

Gln Gly Ala Val Phe Ser Asp Gly Val Gly Met Val Ile Leu Lys Arg
                    245                 250                 255

Leu Glu Asp Ala Ile Ala Asp Gly Asp Thr Ile Tyr Gly Val Ile Lys
                260                 265                 270

Gly Ser Ala Ala Asn Asn Asp Gly Gly Arg Lys Val Gly Tyr Thr Ala
                    275                 280                 285

Pro Ser Val Glu Gly Gln Ala Glu Val Ile Gln Ala Ala His Ser Phe
    290                 295                 300

Ala Glu Val Asp Pro Ser Thr Ile Ser Tyr Val Glu Thr His Gly Thr
305                 310                 315                 320

Ala Thr Pro Leu Gly Asp Ser Ile Glu Val Glu Ala Leu Lys Arg Ala
                    325                 330                 335

Phe Gln Asp Val Asp Lys Lys Ser Phe Cys Ala Ile Gly Ser Val Lys
                340                 345                 350

Ser Asn Val Gly His Leu Asp Thr Ala Ala Gly Val Thr Gly Leu Ile
                    355                 360                 365

Lys Thr Val Leu Ser Met Arg His Lys Gln Leu Pro Pro Thr Leu Asn
    370                 375                 380

Val Lys Arg Pro Asn Ser Lys Ile Asp Phe Ile Asp Ser Pro Phe Tyr
385                 390                 395                 400

Ile Asn Thr Asp Leu Val Asn Trp Gln Ser Asp Asp Asn Asp Leu Leu
                    405                 410                 415

Arg Ala Gly Val Ser Ala Phe Gly Tyr Gly Gly Thr Asn Val His Ile
                420                 425                 430

Val Leu Glu Glu Ala Pro Lys Val Lys Ser Ser Ala Ser Thr Arg Glu
                    435                 440                 445

Lys Lys Leu Met Val Leu Ser Ala Arg Ser Lys Glu Ala Leu Asn Asn
    450                 455                 460

Ala Thr Val Asn Met Val Gln Tyr Leu Glu Ser Asn Lys Asp Val Glu
465                 470                 475                 480

Leu Ala Asp Val Ala Tyr Thr Leu Gln Thr Gly Arg Arg Pro Phe Pro
                    485                 490                 495

Tyr Arg Arg Ala Val Leu Cys Met Asp Ile Asp Ser Ala Ile Asp Asn
                500                 505                 510

Leu Lys Thr Val Lys Asp Phe His Val Lys Thr Gln Glu Asn Pro Asp
                    515                 520                 525

Leu Val Phe Val Leu Pro Ser Glu Tyr Ser Ser Ile Ile Glu Asn Val
    530                 535                 540

Lys Glu Leu Tyr Gln Lys Glu Pro Leu Phe Leu Lys Val Phe Glu Arg
545                 550                 555                 560
```

-continued

```
Asn Met Thr Asp Ala Gln Met Tyr Thr Gly Lys Ala Leu Lys Glu Ala
            565                 570                 575
Phe Phe Lys Gly Thr Asp Ser Leu Val Glu Asp Leu Thr Phe Phe
        580                 585                 590
Val Cys Leu Gln Ser Ile Ile Asp Val Leu Ile Glu Cys Asp Val Arg
            595                 600                 605
Pro Ser Asn Ile Ile Gly Thr Gly Leu Ala Gly Met Val Ser Asp Ile
        610                 615                 620
Tyr Asn Lys Ser Leu Lys Pro Glu Asp Val Leu Asn Gln Leu Val Glu
625                 630                 635                 640
Asn Tyr Thr Glu Leu Gln Thr Glu Trp Thr His Gly Glu Lys Val Glu
            645                 650                 655
Leu Leu Thr Gln Val Lys Asp Val Asp Pro Asn Ser Val Ile Val His
            660                 665                 670
Ile Gly Glu Leu Leu Asn Ser Glu Ile Asn Asn Gln Ile Ile Leu
            675                 680                 685
Gln Asn Asp Leu Leu Glu Val Leu Gly Gln Ala Trp Glu Leu Gly Val
        690                 695                 700
Glu Ile Asn Trp Ser Lys Leu Tyr Glu Glu Tyr Arg Leu Arg Ile
705                 710                 715                 720
Ala Leu Pro Thr Tyr Pro Phe Glu Lys Lys Arg Tyr Trp Ile Asp Pro
            725                 730                 735
Ala Glu Gln Gln Asn Ile Thr Asn Asn Glu Glu Thr Ser Ile Lys Lys
        740                 745                 750
Arg Ser Asn Ile Ala Glu Trp Phe Tyr Thr Pro Gly Trp Met Glu Lys
        755                 760                 765
Glu Ile Val Asp Val Thr Lys Glu Ser Thr Lys Ser Trp Leu Leu Phe
770                 775                 780
Leu Asp Asn Glu His Ile Gly Leu Ala Leu Lys Glu Lys Leu Glu Arg
785                 790                 795                 800
Asp Gly His Arg Val Ile Thr Val Gly Val Gly Pro Ser Tyr Lys Lys
            805                 810                 815
Ile Ser Leu Asn Glu Phe Thr Ile Cys Pro Thr Glu Gln Glu Asp Tyr
        820                 825                 830
Tyr Gln Leu Phe Asn Glu Leu Gln Lys Gln Glu Cys Leu Pro Glu Glu
        835                 840                 845
Ile Val His Leu Trp Asn Val Asp Asn Lys Asp Leu Gly Ile Lys Thr
        850                 855                 860
Leu Asp Thr Gly Phe Tyr Ser Leu Ile Ser Leu Ala Lys Thr Ile Ser
865                 870                 875                 880
Lys Phe Asn Leu Leu Tyr Pro Ile Asn Ile Asn Val Met Thr Asn Asn
                    885                 890                 895
Met Gln Lys Val Val Gly Asp Glu Ser Ile Ile Ala Glu Lys Ser Thr
            900                 905                 910
Leu Leu Ala Pro Ile Lys Val Phe Pro Gln Glu Tyr Pro Asn Ile Arg
        915                 920                 925
Cys Arg Ser Val Asp Phe Met Leu Ser Asp Asn Glu Glu Ala Leu Ile
        930                 935                 940
Ser Asn Leu Tyr Ser Glu Ile Gln Thr Asp Ile Ile Asp Thr Val Ile
945                 950                 955                 960
Ala Ile Arg Asn Asn Thr Arg Tyr Ile Arg Ile Tyr Glu Pro Ile Pro
            965                 970                 975
```

-continued

Asp Glu Lys Val Ser Glu Met Leu Val Ile Asn Glu Asn Glu Leu Ala
                980                 985                 990

Ser Lys Ile Pro Asn Ile Arg Ser Lys Gly Val Tyr Leu Ile Thr Gly
        995                 1000                1005

Gly Met Gly Gly Val Gly Leu Lys Leu Ala Glu Tyr Leu Ala Arg
    1010                1015                1020

Thr Val Lys Ala Lys Leu Ile Leu Val Ser Arg Thr Ala Leu Pro
    1025                1030                1035

Asp Arg Glu Glu Trp Asp Glu Ile Leu Gln Ser Gln Ile Glu Asn
    1040                1045                1050

Glu Gln Leu Cys Gln Arg Ile Asn His Ile Gln Lys Leu Glu Ser
    1055                1060                1065

Leu Gly Ala Lys Val Met Thr Ala Val Ala Asp Val Ala Asp Glu
    1070                1075                1080

Glu Gln Met Arg Asn Val Ile His Gln Ala Glu Ala Asn Phe Gly
    1085                1090                1095

His Ile Asn Gly Val Ile His Ala Ala Gly Val Leu Arg Val Lys
    1100                1105                1110

Ser Ala Gln Cys Pro Met Glu Lys Ile Ser Arg Ile Glu Cys Glu
    1115                1120                1125

Glu Gln Phe Leu Pro Lys Val His Gly Val Leu Val Leu Asp Lys
    1130                1135                1140

Leu Leu Ser Asn Tyr Asp Leu Asp Phe Cys Tyr Leu Val Ser Ser
    1145                1150                1155

Leu Ser Pro Ile Leu Gly Gly Leu Gly Phe Val Ala Tyr Ser Ala
    1160                1165                1170

Ala Asn Leu Tyr Leu Asp Ser Phe Ser Asp Lys Val Ser Asn Thr
    1175                1180                1185

Ser Asn Asn Arg Trp Thr Ser Ile Asn Trp Gly Asp Trp Gln Tyr
    1190                1195                1200

Thr Gly Ala Gln Gln Val Asn Lys Ile Phe Asn Ala Gln Ser Ile
    1205                1210                1215

Glu Ala Leu Glu Met Thr Ser Glu Glu Gly Gln Lys Thr Phe Gln
    1220                1225                1230

Cys Val Leu Gly Leu Ser Gly Leu Asn Gln Val Ile Ile Ser Ser
    1235                1240                1245

Gly Asp Leu Asn Lys Arg Phe Asp Gln Trp Ile Asn Leu Asn Ser
    1250                1255                1260

Arg Lys Arg Ile Ser Glu Leu Glu Thr Gln Thr Lys Thr Gly Asp
    1265                1270                1275

Lys Phe Arg Asn Gln Asp Glu Val Glu Glu Ile Ile Gly Ile
    1280                1285                1290

Trp Lys Glu Phe Tyr Ser Val Asp Thr Val Asn Val Asn Glu Asn
    1295                1300                1305

Phe Phe Asp Leu Gly Ala Thr Ser Leu His Ile Ile Gln Ile His
    1310                1315                1320

Glu Arg Leu Ile Asn Arg Leu Glu Lys Gln Ile Ser Ile Gly Val
    1325                1330                1335

Met Phe Glu Tyr Pro Ser Ile Arg Ser Leu Ala Arg Tyr Leu Ser
    1340                1345                1350

Gly Asp Lys Gln Lys Asn Gln Val Lys His Thr Lys Arg Phe Asn
    1355                1360                1365

Arg Lys Thr Lys Glu Asp Asn Asp Ile Ala Ile Ile Gly Ile Asp

-continued

```
         1370              1375              1380
Gly Arg Phe Pro Gly Ala Gln Asn Val Asn Glu Phe Trp Asn Asn
         1385              1390              1395
Ile Lys Ser Gly Thr Glu Ser Ile Gln Phe Phe Thr Asp Glu Glu
         1400              1405              1410
Leu Ile Glu Ser Gly Val Asn Pro Met Glu Val Lys Ser Pro Asn
         1415              1420              1425
Tyr Val Lys Ala Lys Gly Tyr Leu Glu Gly Thr Asp Asn Phe Asp
         1430              1435              1440
Ala Pro Phe Phe Asp Tyr Thr Pro Gln Asp Ala Ser Leu Met Asp
         1445              1450              1455
Pro Gln Leu Arg Val Phe His Glu Cys Ala Trp Ser Ala Leu Glu
         1460              1465              1470
His Ala Gly Tyr Asn Ile Glu Thr Tyr Pro Gly Leu Ile Gly Val
         1475              1480              1485
Tyr Ser Gly Ala Ser Pro Asn Leu Tyr Trp Gln Val Leu Ser Thr
         1490              1495              1500
Leu Ser Glu Ala Asn Glu Pro Ala Gly Gln Phe Leu Ile Ser Leu
         1505              1510              1515
Leu Asn Asp Lys Asp Ser Leu Ser Thr Gln Ile Ser Tyr Lys Phe
         1520              1525              1530
Asn Leu Lys Gly Pro Ser Met Asn Ile Phe Thr Gly Cys Ser Thr
         1535              1540              1545
Ser Leu Val Ala Ile His Asn Ala Cys Gln Ala Leu Leu Gln Gly
         1550              1555              1560
His Cys Asp Ile Ala Ile Ala Gly Gly Ile Thr Leu Thr Gln Pro
         1565              1570              1575
Glu Lys Ala Gly Tyr Thr Tyr Gln Glu Gly Met Leu Phe Ser Ser
         1580              1585              1590
Asp Gly His Cys Arg Pro Phe Asp Glu Asn Ala Asn Gly Met Leu
         1595              1600              1605
Phe Gly Asp Gly Val Gly Ile Val Val Leu Lys Pro Leu Gln Glu
         1610              1615              1620
Ala Ile Asn Asp Gly Asp Thr Ile His Ala Val Ile Lys Gly Thr
         1625              1630              1635
Ala Ile Asn Asn Asp Gly Asn Arg Lys Ile Gly Tyr Thr Ala Pro
         1640              1645              1650
Ser Val Glu Gly Gln Val Glu Val Ile Lys Met Ala Gln His Glu
         1655              1660              1665
Ala Asn Val Glu Pro Glu Ser Ile Ser Tyr Ile Glu Thr His Gly
         1670              1675              1680
Thr Ala Thr Lys Leu Gly Asp Thr Ile Glu Ile Lys Ala Leu Ser
         1685              1690              1695
Glu Val Phe Asn Ser Asn Glu Lys Gln Ser Val Pro Ile Gly Ser
         1700              1705              1710
Val Lys Ala Asn Val Gly His Leu Asn Ala Ala Ser Gly Val Ala
         1715              1720              1725
Gly Leu Ile Lys Thr Val Phe Ala Met Lys Asp Gln Val Leu Pro
         1730              1735              1740
Pro Ser Val Asn Phe Thr Lys Pro Asn Thr Gln Ile Gly Phe Glu
         1745              1750              1755
Lys Thr Pro Phe Tyr Val Asn Gln Gln Leu Asn Glu Trp Lys Glu
         1760              1765              1770
```

-continued

Asp Asn Lys Pro Leu Arg Ala Gly Val Ser Ser Phe Gly Ile Gly
1775                1780                1785

Gly Thr Asn Ala His Ile Ile Leu Glu Glu Ala Pro Lys Leu Glu
1790                1795                1800

Ala Thr Ser Asn Ser Arg Pro Tyr Gln Met Leu Met Ile Ser Ala
1805                1810                1815

Lys Ser Lys Asp Ala Leu Asp Arg Met Thr Leu Asn Leu Gly Asn
1820                1825                1830

His Leu Glu Gln Asn Pro His Val Asn Leu Ala Asp Ala Ser Tyr
1835                1840                1845

Thr Leu Gln Ile Gly Arg Lys Glu Phe Lys His Arg Arg Ala Leu
1850                1855                1860

Val Cys Ser Ser Thr Gln Glu Gly Ile Glu Gln Leu Asn Gln Pro
1865                1870                1875

Asp Gly Arg Arg Val Gln Tyr Ala Asn Val Lys Glu Glu His Pro
1880                1885                1890

Lys Ile His Phe Leu Phe Ser Gly Asn Gly Ser Gln Tyr Val Asn
1895                1900                1905

Met Gly Leu Glu Leu Tyr Glu Gln Glu Ala Ile Phe Arg Glu Ala
1910                1915                1920

Met Asp Glu Cys Phe Ala Ile Leu Gln Ser Phe Thr Asn Val Asn
1925                1930                1935

Met Lys Glu Val Leu Tyr Pro Thr Thr Phe Ser Ile Asn Glu Ala
1940                1945                1950

Thr Glu Lys Leu Lys Arg Met Glu Phe Ser Gln Pro Ile Leu Phe
1955                1960                1965

Ala Phe Glu Tyr Ala Val Ala Lys Leu Leu Met Gly Trp Gly Ile
1970                1975                1980

Lys Pro Glu Ala Met Ile Gly Tyr Ser Phe Gly Glu Tyr Val Ala
1985                1990                1995

Ala Cys Leu Ala Glu Val Phe Thr Leu Glu Asp Ala Leu Lys Leu
2000                2005                2010

Val Val Lys Arg Gly Gln Leu Met Ser Ser Leu Pro Ala Gly Val
2015                2020                2025

Met Leu Ser Val Pro Leu Pro Glu Glu Glu Leu Ile His Leu Ile
2030                2035                2040

Asn Ser Phe Glu Lys Glu Tyr Gln His Thr Ile Ser Leu Ala Val
2045                2050                2055

Val Asn Gly Pro Ala Cys Ile Val Ser Gly Thr Glu Glu Ala Ile
2060                2065                2070

Val Asp Phe Glu Asn Glu Leu Lys Lys Gln Arg Leu Met Cys Met
2075                2080                2085

Arg Val Thr Ile Glu Gly Ala Ala His Ser His Glu Leu Asp Ser
2090                2095                2100

Ile Leu Asp Glu Tyr Ala Ser Tyr Val Ser Thr Leu Thr Leu Arg
2105                2110                2115

Glu Pro Lys Ile Pro Tyr Leu Ser Asn Leu Thr Gly Thr Trp Ile
2120                2125                2130

Arg Pro Glu Glu Ala Thr Asn Pro Val Tyr Trp Val Lys His Met
2135                2140                2145

Arg Gly Thr Val Arg Phe Ser Asp Gly Ile Gln Glu Leu Asn Arg
2150                2155                2160

```
Asp Asn Thr Ser Leu Phe Ile Glu Ile Gly Pro Gly Asn Asp Leu
    2165                2170                2175

Ser Arg Leu Thr Ser Arg Leu Leu Asp Tyr Glu Asn Gly Asn Glu
    2180                2185                2190

Arg Ile Phe Asn Thr Val Arg Ser Val Gln Gln Asp Val Ser Asp
    2195                2200                2205

Met Tyr Phe Leu Phe Ser His Ile Thr Arg Met Trp Val Thr Gly
    2210                2215                2220

Ile Ser Val Asp Trp Glu Gln Phe Tyr Lys Asp Glu Lys Arg Arg
    2225                2230                2235

Arg Ile Pro Leu Pro Met Tyr Ser Phe Asn Lys Ile Ser Tyr Lys
    2240                2245                2250

Leu Gln Gly Asn Pro Tyr Asp Leu Gly Gln Lys Leu Asn Ser Lys
    2255                2260                2265

Gln Ser Lys Ile Ser Lys Asn Asn Ile Ser Glu Trp Phe Tyr
    2270                2275                2280

Thr Pro Gln Trp Lys Ser Ser Thr Leu Phe Glu Pro Asn His Asp
    2285                2290                2295

Val Asn Glu Thr Trp Ile Val Phe Val Asp Gln Glu Gly Leu Gly
    2300                2305                2310

Asn Glu Leu Val Lys Asp Leu Leu Asn Lys Gly Gln Arg Val Val
    2315                2320                2325

Thr Val Glu Pro Gly Phe Ala Phe Asn Lys Glu Asn Asn Asp Arg
    2330                2335                2340

Phe Ile Ile Asn Pro Glu Glu Arg Thr Asp Tyr Val Lys Leu Leu
    2345                2350                2355

Asp Glu Val Gln Glu Ile Tyr Gly Leu Pro Thr Arg Ile Ile His
    2360                2365                2370

Met Trp Gly Ile Thr Asn Glu Glu Arg Gln Ala Ser Ile Glu Tyr
    2375                2380                2385

Val Asn Cys Lys Gln Asn Leu Gly Phe Tyr Ser Met Phe Tyr Leu
    2390                2395                2400

Thr Gln Ala Leu Gly Asp Lys Asn Ile Ser Asp Ser Ile Ser Ile
    2405                2410                2415

Arg Ile Ile Thr Asn Gly Val Gln Gln Val Ile Gly Asp Glu Glu
    2420                2425                2430

Leu Ile Pro Glu Lys Ser Thr Val Leu Gly Thr Ser Leu Val Val
    2435                2440                2445

Pro Gln Glu Tyr Ser Tyr Leu Ser Cys Ser Ser Val Asp Val Val
    2450                2455                2460

Leu Pro Leu Lys Lys Glu Trp Lys Asn Arg Leu Ile Asn Gln Leu
    2465                2470                2475

Val Glu Glu Cys Leu Ser Asn Thr Asn Asp Lys Met Ile Ala Tyr
    2480                2485                2490

Arg Gly Asn Lys Arg Phe Val Gln Thr Tyr Glu Pro Leu Gln Leu
    2495                2500                2505

Glu Gln Pro Ala Lys Glu Lys Leu Pro Leu Arg Lys Asn Gly Val
    2510                2515                2520

Tyr Leu Ile Thr Gly Gly Leu Gly Gly Ile Gly Thr Ile Leu Ala
    2525                2530                2535

Lys His Leu Ala Gln Thr Val Gln Ala Asn Leu Val Leu Leu Thr
    2540                2545                2550

Arg Thr Gly Leu Pro Asn Arg Asp Glu Trp Asp Met His Leu Lys
```

```
              2555                2560                2565

Glu Asn Thr Met Tyr Ser Asp Arg Ile Arg Lys Val Leu Glu Ile
    2570                2575                2580

Glu Glu Thr Gly Ser Lys Val Tyr Val Leu Ala Ala Asp Val Thr
    2585                2590                2595

Asp Gln Ser Gln Leu Tyr Glu Ala Ile His Lys Ala Glu Gln Lys
    2600                2605                2610

Phe Gly Lys Ile Asn Gly Val Ile His Gly Ala Gly Ile Leu Gly
    2615                2620                2625

Gly Lys Thr Phe Asn Leu Ile Gln Glu Leu Glu Lys Glu Asp Cys
    2630                2635                2640

Glu Glu Gln Phe Ser Ala Lys Ile Tyr Gly Leu Leu Asn Leu Glu
    2645                2650                2655

Glu Cys Leu Arg Asn Lys Asp Leu Asp Phe Cys Val Leu Met Ser
    2660                2665                2670

Ser Ile Ser Ala Val Leu Gly Gly Leu Gly Tyr Val Ser Tyr Ala
    2675                2680                2685

Ala Ser Asn Ile Tyr Met Asp Val Phe Ala Gln Tyr Ile Asn Arg
    2690                2695                2700

Tyr Ser Lys Leu Pro Trp Ile Ser Val Asn Trp Ser Asp Trp Lys
    2705                2710                2715

Tyr Trp Glu Asp Glu Lys Asp Met Gln Ile Gly Ala Ser Val
    2720                2725                2730

His Glu Leu Ser Met Thr Pro Glu Glu Gly Val Gln Ala Phe Asn
    2735                2740                2745

Ile Ala Leu Ser Trp Lys Gln Gly Glu Val Leu Ile His Ser Pro
    2750                2755                2760

Gly Glu Leu Gln Ala Arg Ile Asp Gln Trp Val Leu Leu Asn Ser
    2765                2770                2775

Phe Asn Asp Glu Lys Glu Glu Leu Asp Ser Thr Leu Tyr His
    2780                2785                2790

Ser Arg Pro Gln Leu Leu Thr Glu Tyr Val Ala Pro Arg Asn Glu
    2795                2800                2805

Val Glu Glu Lys Leu Ser Lys Ile Trp Arg Asn Ile Phe Lys Val
    2810                2815                2820

Ser Glu Val Gly Val His Asp Asp Leu Leu Glu Leu Gly Gly Asp
    2825                2830                2835

Ser Leu Lys Ala Ile Thr Ile Val Ser Lys Ile His Lys Glu Phe
    2840                2845                2850

Asn Val Glu Val Pro Ile Lys Glu Leu Phe Thr Leu Ser Asn Ile
    2855                2860                2865

Glu Lys Leu Ala Asn Tyr Ile Ser Arg Ala Asp Lys Ser Glu Phe
    2870                2875                2880

Asp Val Ile Val Pro Ala Glu Pro Lys Ser His Tyr Gln Leu Ser
    2885                2890                2895

Ser Ala Gln Lys Arg Phe Tyr Val Leu His Arg Leu Tyr Pro Glu
    2900                2905                2910

Ser Thr Ala Tyr Asn Asp Thr Ser Val Ile Leu Leu Asn Gly Lys
    2915                2920                2925

Leu Asn Ile Glu Arg Leu Glu Lys Ala Phe Thr Gln Leu Ile Lys
    2930                2935                2940

Arg His Glu Ile Phe Arg Thr Thr Ile Glu Met Lys Asn Asp Lys
    2945                2950                2955
```

```
Pro Val Gln Ile Ile His Asp His Ala Asp Phe His Ile Thr Gln
    2960            2965                2970

Ile Glu Gly Phe Glu Ser Glu Val Glu Gln Ile Ile Asn Glu Phe
    2975            2980                2985

Ile Arg Pro Phe Asn Phe Asn Asn Ala Pro Tyr Phe Arg Val Gly
    2990            2995                3000

Leu Ile Arg Leu Glu Glu Gln Lys His Ile Leu Ile Ile Asp Leu
    3005            3010                3015

His His Ile Val Thr Asp Gly Val Ser Tyr Asp Ile Phe Val Arg
    3020            3025                3030

Asp Leu Phe Ala Leu Tyr Ser Gly Glu Lys Leu Pro Asn Leu Lys
    3035            3040                3045

Ile Gln Tyr Lys Asp Tyr Ser Glu Trp Gln Gln Ser Glu Lys Glu
    3050            3055                3060

Lys Glu Ile Ala Leu Lys His Glu Gln Tyr Trp Leu Glu Gln Phe
    3065            3070                3075

Lys Asp Gly Val Pro Val Leu Asn Met Pro Thr Asp Tyr Thr Arg
    3080            3085                3090

Pro Glu Ile Ile Asp Leu Lys Gly Ser Lys Ile Ser Phe Thr Ile
    3095            3100                3105

Asp Ser Asn Val Thr Lys Lys Ile Lys Arg Leu Leu Ala Lys Glu
    3110            3115                3120

Glu Thr Thr Leu Tyr Thr Leu Met Leu Ser Val Tyr Asn Ile Leu
    3125            3130                3135

Leu Gly Lys Tyr Thr Gly Gln Glu Asp Val Val Ile Gly Ser Pro
    3140            3145                3150

Ile Thr Gly Arg Pro His Ala Asp Leu Gln Asp Ile Ile Gly Val
    3155            3160                3165

Phe Val Asn Met Leu Gly Ile Arg Asn Tyr Pro Arg Ala Glu Gln
    3170            3175                3180

Arg Phe Thr Gln Phe Leu Phe Glu Val Lys Glu Gln Val Leu Gln
    3185            3190                3195

Ala Phe Glu His Gln Lys Cys Gln Tyr Glu Asp Leu Val Asn Lys
    3200            3205                3210

Leu Gly Leu Gln Gly Thr Tyr Asn Arg Asn Pro Leu Phe Asp Val
    3215            3220                3225

Ser Phe Val Met Gln Asn Met Asp Ala Asp His Met Phe Ile Asp
    3230            3235                3240

Gly Leu Glu Leu Arg Thr Tyr Asp His Asp Phe Lys Arg Ala Gln
    3245            3250                3255

Met Asp Leu Leu Leu Arg Val Val Glu Leu Glu Asp Thr Ile Glu
    3260            3265                3270

Leu Thr Met Glu Tyr Ala Thr Ser Leu Tyr Thr Arg Asp Thr Val
    3275            3280                3285

Gln Lys Leu Cys Glu Arg Tyr Val Glu Ile Phe Glu Gln Ile Val
    3290            3295                3300

Asp His Pro Glu Ile Leu Leu Lys Asp Ile Ser Phe Lys Gln Glu
    3305            3310                3315

Ile Gln Glu Leu Gln Pro Val Lys Val Ser Val Asp Phe Gly Asp
    3320            3325                3330

Phe Asn Phe
    3335
```

-continued

<210> SEQ ID NO 6
<211> LENGTH: 405
<212> TYPE: PRT
<213> ORGANISM: Bacillus cereus

<400> SEQUENCE: 6

```
Met Asn Ile Val Phe Met Phe Pro Gly Val Gly Ser His Tyr Ser Gly
1               5                   10                  15

Met Gly Lys Tyr Leu Tyr Glu Asn Phe Pro Val Ala Arg Glu Ile Phe
            20                  25                  30

Glu Glu Ala Ser Asp Thr Leu Lys Ile Asp Met Ala Ser Leu Cys Met
        35                  40                  45

Glu Lys Ile Tyr Lys Ala Asp Leu Glu Lys Leu Gln Asn Ser Gln Thr
    50                  55                  60

Ala Leu Val Thr Thr Ser Met Ala Ala Phe Arg Val Phe Glu Gln Glu
65                  70                  75                  80

Ile Gly Asn Lys Pro Glu Ala Met Ile Gly Tyr Ser Leu Gly Glu Tyr
                85                  90                  95

Thr Ala Leu Cys Ala Ser Gly Ala Ile Ala Phe Ser Asp Thr Leu Lys
            100                 105                 110

Leu Val Gln Glu Arg Ser Thr Ile Leu Ser Ser Tyr Ala Leu Thr Ile
        115                 120                 125

Asp Gly Thr Met Ala Trp Val Asn Asn Leu Ala Pro Glu Ile Val Glu
    130                 135                 140

Gly Ile Cys Ser Glu Leu Leu Thr Lys Gly Gln Glu Val Tyr Ile Ser
145                 150                 155                 160

Ala Tyr Asp Thr Pro Asn Lys Thr Ser Ile Ser Gly Thr Asn Ser Ala
                165                 170                 175

Val Gln Leu Ala Cys Glu Met Val Val Glu His Gly Gly Ile Ala Ile
            180                 185                 190

Pro Leu Lys Leu Ser Gly Pro Phe His Ser Pro Met Met Gln Pro Ala
        195                 200                 205

Ala Glu Lys Tyr Lys Ser Val Leu Glu Asn Ile Asp Met Lys Gln Pro
    210                 215                 220

Leu Val Pro Val Ile Ala Asn His Asp Ser Ser Met Tyr Lys Gly Val
225                 230                 235                 240

Glu Asn Ile Arg Glu Asn Leu Tyr Leu Gln Leu Ile Lys Pro Val Lys
                245                 250                 255

Trp Leu Asp Met Ile His Tyr Leu Met Asn Gln Gly Ser Met Lys Ala
            260                 265                 270

Ile Glu Met Gly Pro Lys Glu Val Leu Lys Tyr Leu Leu Gln Ala Ile
        275                 280                 285

Asn Pro Ala Ile Ser Thr Cys Asn Tyr Glu Arg Glu Lys Asp Ile Leu
    290                 295                 300

Asn Thr Lys Asn Ser Phe Thr Leu Gln Glu Ser Asp Tyr Glu Glu Val
305                 310                 315                 320

Ile Ser Gly Cys Leu Thr Val Val Val Ser Thr Lys Asn Tyr Asn Thr
                325                 330                 335

Asp Leu Ser Glu Tyr Gln Lys Lys Val Val Arg Pro Phe Gln Lys Val
            340                 345                 350

Gln Ser Gln Phe Glu Glu Lys Ile Asn Ser Gly Tyr Ser Val Glu Lys
        355                 360                 365

Ser Asp Val Glu Glu Ala Ile Gln Met Met Lys Thr Ala Leu Thr Glu
    370                 375                 380
```

```
Lys Gln Ile Lys Glu Arg Glu Gln Lys Arg Tyr Leu Gln Arg Val Leu
385                 390                 395                 400

Gln Cys Lys Ser Phe
                405

<210> SEQ ID NO 7
<211> LENGTH: 438
<212> TYPE: PRT
<213> ORGANISM: Bacillus cereus

<400> SEQUENCE: 7

Met Lys His Gln Asp Asp Ser Lys Thr Gly Leu Glu Ile Ala Ile Ile
1               5                   10                  15

Gly Met Ala Gly Lys Phe Pro Gly Ala Asn Glu Ile Asn Gln Phe Trp
            20                  25                  30

Asp Asn Leu Lys Asn Gly Val Asp Ser Ile Ser Thr Phe Thr Glu Asp
        35                  40                  45

Glu Leu Ile Lys Glu Gly Val Asn Leu Asp Val Leu Gln His Pro Asn
    50                  55                  60

Phe Val Lys Ala Lys Gly Tyr Leu Glu Glu Val Glu Tyr Phe Asp Glu
65                  70                  75                  80

Ser Phe Phe Ala Tyr Thr Pro Arg Glu Ala Lys Ile Met Asp Pro Gln
                85                  90                  95

Ile Arg Met Leu Gln Glu Thr Thr Trp Glu Ala Leu Glu Met Ala Gly
            100                 105                 110

Tyr Asn Pro Phe Asp Tyr Glu Gly Leu Ile Gly Leu Tyr Val Gly Ala
        115                 120                 125

Ser Thr Asn Phe Asn Trp Met Lys His Thr Pro Leu Leu Asn Ser Asp
    130                 135                 140

Ser Val Val Glu Phe Ser Glu Ala Gly Thr Leu Ser Tyr Lys Asp Ala
145                 150                 155                 160

Ile Ser Thr Leu Thr Ser Tyr Lys Leu Gly Leu Lys Gly Pro Ser Phe
                165                 170                 175

Thr Leu Tyr Thr Ala Cys Ser Thr Ser Leu Leu Ser Ile His Leu Ala
            180                 185                 190

Cys Arg Ser Leu Leu Thr Gly Glu Cys Ser Ile Ala Ala Ala Gly Gly
        195                 200                 205

Val Ser Ile Thr Tyr Pro Lys Lys Asn Gly Tyr Lys Tyr His Glu Gly
    210                 215                 220

Met Thr Ser Ser Pro Asp Gly Lys Val Arg Thr Phe Asp Ala Glu Ala
225                 230                 235                 240

Gln Gly Ala Val Phe Ser Asp Gly Val Gly Met Val Ile Leu Lys Arg
                245                 250                 255

Leu Glu Asp Ala Ile Ala Asp Gly Asp Thr Ile Tyr Gly Val Ile Lys
            260                 265                 270

Gly Ser Ala Ala Asn Asn Asp Gly Gly Arg Lys Val Gly Tyr Thr Ala
        275                 280                 285

Pro Ser Val Glu Gly Gln Ala Glu Val Ile Gln Ala Ala His Ser Phe
    290                 295                 300

Ala Glu Val Asp Pro Ser Thr Ile Ser Tyr Val Glu Thr His Gly Thr
305                 310                 315                 320

Ala Thr Pro Leu Gly Asp Ser Ile Glu Val Glu Ala Leu Lys Arg Ala
                325                 330                 335

Phe Gln Asp Val Asp Lys Lys Ser Phe Cys Ala Ile Gly Ser Val Lys
```

-continued 340                 345                 350

Ser Asn Val Gly His Leu Asp Thr Ala Ala Gly Val Thr Gly Leu Ile
        355                 360                 365

Lys Thr Val Leu Ser Met Arg His Lys Gln Leu Pro Pro Thr Leu Asn
    370                 375                 380

Val Lys Arg Pro Asn Ser Lys Ile Asp Phe Ile Asp Ser Pro Phe Tyr
385                 390                 395                 400

Ile Asn Thr Asp Leu Val Asn Trp Gln Ser Asp Asp Asn Asp Leu Leu
                405                 410                 415

Arg Ala Gly Val Ser Ala Phe Gly Tyr Gly Gly Thr Asn Val His Ile
            420                 425                 430

Val Leu Glu Glu Ala Pro
        435

<210> SEQ ID NO 8
<211> LENGTH: 202
<212> TYPE: PRT
<213> ORGANISM: Bacillus cereus

<400> SEQUENCE: 8

Gly Val Tyr Leu Ile Thr Gly Gly Met Gly Gly Val Gly Leu Lys Leu
1               5                   10                  15

Ala Glu Tyr Leu Ala Arg Thr Val Lys Ala Lys Leu Ile Leu Val Ser
            20                  25                  30

Arg Thr Ala Leu Pro Asp Arg Glu Glu Trp Asp Glu Ile Leu Gln Ser
        35                  40                  45

Gln Ile Glu Asn Glu Gln Leu Cys Gln Arg Ile Asn His Ile Gln Lys
    50                  55                  60

Leu Glu Ser Leu Gly Ala Lys Val Met Thr Ala Val Ala Asp Val Ala
65                  70                  75                  80

Asp Glu Glu Gln Met Arg Asn Val Ile His Gln Ala Glu Ala Asn Phe
                85                  90                  95

Gly His Ile Asn Gly Val Ile His Ala Ala Gly Val Leu Arg Val Lys
            100                 105                 110

Ser Ala Gln Cys Pro Met Glu Lys Ile Ser Arg Ile Glu Cys Glu Glu
        115                 120                 125

Gln Phe Leu Pro Lys Val His Gly Val Leu Val Leu Asp Lys Leu Leu
    130                 135                 140

Ser Asn Tyr Asp Leu Asp Phe Cys Tyr Leu Val Ser Ser Leu Ser Pro
145                 150                 155                 160

Ile Leu Gly Gly Leu Gly Phe Val Ala Tyr Ser Ala Ala Asn Leu Tyr
                165                 170                 175

Leu Asp Ser Phe Ser Asp Lys Val Ser Asn Thr Ser Asn Asn Arg Trp
            180                 185                 190

Thr Ser Ile Asn Trp Gly Asp Trp Gln Tyr
        195                 200

<210> SEQ ID NO 9
<211> LENGTH: 65
<212> TYPE: PRT
<213> ORGANISM: Bacillus cereus

<400> SEQUENCE: 9

Glu Ile Ile Ile Gly Ile Trp Lys Glu Phe Tyr Ser Val Asp Thr Val
1               5                   10                  15

Asn Val Asn Glu Asn Phe Phe Asp Leu Gly Ala Thr Ser Leu His Ile

```
            20                  25                  30

Ile Gln Ile His Glu Arg Leu Ile Asn Arg Leu Glu Lys Gln Ile Ser
        35                  40                  45

Ile Gly Val Met Phe Glu Tyr Pro Ser Ile Arg Ser Leu Ala Arg Tyr
    50                  55                  60

Leu
65

<210> SEQ ID NO 10
<211> LENGTH: 426
<212> TYPE: PRT
<213> ORGANISM: Bacillus cereus

<400> SEQUENCE: 10

Asn Asp Ile Ala Ile Ile Gly Ile Asp Gly Arg Phe Pro Gly Ala Gln
1               5                   10                  15

Asn Val Asn Glu Phe Trp Asn Asn Ile Lys Ser Gly Thr Glu Ser Ile
            20                  25                  30

Gln Phe Phe Thr Asp Glu Glu Leu Ile Glu Ser Gly Val Asn Pro Met
        35                  40                  45

Glu Val Lys Ser Pro Asn Tyr Val Lys Ala Lys Gly Tyr Leu Glu Gly
    50                  55                  60

Thr Asp Asn Phe Asp Ala Pro Phe Phe Asp Tyr Thr Pro Gln Asp Ala
65                  70                  75                  80

Ser Leu Met Asp Pro Gln Leu Arg Val Phe His Glu Cys Ala Trp Ser
                85                  90                  95

Ala Leu Glu His Ala Gly Tyr Asn Ile Glu Thr Tyr Pro Gly Leu Ile
            100                 105                 110

Gly Val Tyr Ser Gly Ala Ser Pro Asn Leu Tyr Trp Gln Val Leu Ser
        115                 120                 125

Thr Leu Ser Glu Ala Asn Glu Pro Ala Gly Gln Phe Leu Ile Ser Leu
    130                 135                 140

Leu Asn Asp Lys Asp Ser Leu Ser Thr Gln Ile Ser Tyr Lys Phe Asn
145                 150                 155                 160

Leu Lys Gly Pro Ser Met Asn Ile Phe Thr Gly Cys Ser Thr Ser Leu
                165                 170                 175

Val Ala Ile His Asn Ala Cys Gln Ala Leu Leu Gln Gly His Cys Asp
            180                 185                 190

Ile Ala Ile Ala Gly Gly Ile Thr Leu Thr Gln Pro Glu Lys Ala Gly
        195                 200                 205

Tyr Thr Tyr Gln Glu Gly Met Leu Phe Ser Ser Asp Gly His Cys Arg
    210                 215                 220

Pro Phe Asp Glu Asn Ala Asn Gly Met Leu Phe Gly Asp Gly Val Gly
225                 230                 235                 240

Ile Val Val Leu Lys Pro Leu Gln Glu Ala Ile Asn Asp Gly Asp Thr
                245                 250                 255

Ile His Ala Val Ile Lys Gly Thr Ala Ile Asn Asn Asp Gly Asn Arg
            260                 265                 270

Lys Ile Gly Tyr Thr Ala Pro Ser Val Glu Gly Gln Val Glu Val Ile
        275                 280                 285

Lys Met Ala Gln His Glu Ala Asn Val Glu Pro Glu Ser Ile Ser Tyr
    290                 295                 300

Ile Glu Thr His Gly Thr Ala Thr Lys Leu Gly Asp Thr Ile Glu Ile
305                 310                 315                 320
```

```
Lys Ala Leu Ser Glu Val Phe Asn Ser Asn Glu Lys Gln Ser Val Pro
                325                 330                 335

Ile Gly Ser Val Lys Ala Asn Val Gly His Leu Asn Ala Ala Ser Gly
            340                 345                 350

Val Ala Gly Leu Ile Lys Thr Val Phe Ala Met Lys Asp Gln Val Leu
        355                 360                 365

Pro Pro Ser Val Asn Phe Thr Lys Pro Asn Thr Gln Ile Gly Phe Glu
    370                 375                 380

Lys Thr Pro Phe Tyr Val Asn Gln Gln Leu Asn Glu Trp Lys Glu Asp
385                 390                 395                 400

Asn Lys Pro Leu Arg Ala Gly Val Ser Ser Phe Gly Ile Gly Gly Thr
                405                 410                 415

Asn Ala His Ile Ile Leu Glu Glu Ala Pro
            420                 425

<210> SEQ ID NO 11
<211> LENGTH: 308
<212> TYPE: PRT
<213> ORGANISM: Bacillus cereus

<400> SEQUENCE: 11

Leu Phe Ser Gly Asn Gly Ser Gln Tyr Val Asn Met Gly Leu Glu Leu
1               5                   10                  15

Tyr Glu Gln Glu Ala Ile Phe Arg Glu Ala Met Asp Glu Cys Phe Ala
            20                  25                  30

Ile Leu Gln Ser Phe Thr Asn Val Asn Met Lys Glu Val Leu Tyr Pro
        35                  40                  45

Thr Thr Phe Ser Ile Asn Glu Ala Thr Glu Lys Leu Lys Arg Met Glu
    50                  55                  60

Phe Ser Gln Pro Ile Leu Phe Ala Phe Glu Tyr Ala Val Ala Lys Leu
65                  70                  75                  80

Leu Met Gly Trp Gly Ile Lys Pro Glu Ala Met Ile Gly Tyr Ser Phe
                85                  90                  95

Gly Glu Tyr Val Ala Ala Cys Leu Ala Glu Val Phe Thr Leu Glu Asp
            100                 105                 110

Ala Leu Lys Leu Val Val Lys Arg Gly Gln Leu Met Ser Ser Leu Pro
        115                 120                 125

Ala Gly Val Met Leu Ser Val Pro Leu Pro Glu Glu Leu Ile His
    130                 135                 140

Leu Ile Asn Ser Phe Glu Lys Glu Tyr Gln His Thr Ile Ser Leu Ala
145                 150                 155                 160

Val Val Asn Gly Pro Ala Cys Ile Val Ser Gly Thr Glu Glu Ala Ile
                165                 170                 175

Val Asp Phe Glu Asn Glu Leu Lys Lys Gln Arg Leu Met Cys Met Arg
            180                 185                 190

Val Thr Ile Glu Gly Ala Ala His Ser His Glu Leu Asp Ser Ile Leu
        195                 200                 205

Asp Glu Tyr Ala Ser Tyr Val Ser Thr Leu Thr Leu Arg Glu Pro Lys
    210                 215                 220

Ile Pro Tyr Leu Ser Asn Leu Thr Gly Thr Trp Ile Arg Pro Glu Glu
225                 230                 235                 240

Ala Thr Asn Pro Val Tyr Trp Val Lys His Met Arg Gly Thr Val Arg
                245                 250                 255

Phe Ser Asp Gly Ile Gln Glu Leu Asn Arg Asp Asn Thr Ser Leu Phe
            260                 265                 270
```

```
Ile Glu Ile Gly Pro Gly Asn Asp Leu Ser Arg Leu Thr Ser Arg Leu
        275                 280                 285

Leu Asp Tyr Glu Asn Gly Asn Glu Arg Ile Phe Asn Thr Val Arg Ser
        290                 295                 300

Val Gln Gln Asp
305

<210> SEQ ID NO 12
<211> LENGTH: 198
<212> TYPE: PRT
<213> ORGANISM: Bacillus cereus

<400> SEQUENCE: 12

Gly Val Tyr Leu Ile Thr Gly Leu Gly Gly Ile Gly Thr Ile Leu
1               5                   10                  15

Ala Lys His Leu Ala Gln Thr Val Gln Ala Asn Leu Val Leu Leu Thr
            20                  25                  30

Arg Thr Gly Leu Pro Asn Arg Asp Glu Trp Asp Met His Leu Lys Glu
        35                  40                  45

Asn Thr Met Tyr Ser Asp Arg Ile Arg Lys Val Leu Glu Ile Glu Glu
    50                  55                  60

Thr Gly Ser Lys Val Tyr Val Leu Ala Ala Asp Val Thr Asp Gln Ser
65                  70                  75                  80

Gln Leu Tyr Glu Ala Ile His Lys Ala Glu Gln Lys Phe Gly Lys Ile
                85                  90                  95

Asn Gly Val Ile His Gly Ala Gly Ile Leu Gly Gly Lys Thr Phe Asn
            100                 105                 110

Leu Ile Gln Glu Leu Glu Lys Glu Asp Cys Glu Glu Gln Phe Ser Ala
        115                 120                 125

Lys Ile Tyr Gly Leu Leu Asn Leu Glu Glu Cys Leu Arg Asn Lys Asp
    130                 135                 140

Leu Asp Phe Cys Val Leu Met Ser Ser Ile Ser Ala Val Leu Gly Gly
145                 150                 155                 160

Leu Gly Tyr Val Ser Tyr Ala Ala Ser Asn Ile Tyr Met Asp Val Phe
                165                 170                 175

Ala Gln Tyr Ile Asn Arg Tyr Ser Lys Leu Pro Trp Ile Ser Val Asn
            180                 185                 190

Trp Ser Asp Trp Lys Tyr
        195

<210> SEQ ID NO 13
<211> LENGTH: 65
<212> TYPE: PRT
<213> ORGANISM: Bacillus cereus

<400> SEQUENCE: 13

Glu Lys Leu Ser Lys Ile Trp Arg Asn Ile Phe Lys Val Ser Glu Val
1               5                   10                  15

Gly Val His Asp Asp Leu Leu Glu Leu Gly Gly Asp Ser Leu Lys Ala
            20                  25                  30

Ile Thr Ile Val Ser Lys Ile His Lys Glu Phe Asn Val Glu Val Pro
        35                  40                  45

Ile Lys Glu Leu Phe Thr Leu Ser Asn Ile Glu Lys Leu Ala Asn Tyr
    50                  55                  60

Ile
65
```

```
<210> SEQ ID NO 14
<211> LENGTH: 5
<212> TYPE: PRT
<213> ORGANISM: Bacillus cereus

<400> SEQUENCE: 14

Gly Leu Val Asn Ser
1               5
```

TYPE I POLYKETIDE SYNTHASE EXTENDER UNITS

CROSS-REFERENCE TO RELATED APPLICATIONS

This invention claims priority to U.S. Provisional Patent Application Ser. No. 60/923,105, filed Apr. 12, 2007, which is herein incorporated by reference.

GOVERNMENT INTERESTS

This invention was made with United States government support under grant No. A1065850 awarded by the NIH. The United States government has certain rights in this invention.

FIELD OF THE INVENTION

The present invention is related to the field of polyketide synthases (PKSs) and extender units used in the synthesis of polyketide molecules. The present invention is also related to the field of PKS molecules capable of recognizing and incorporating particular PKS extender units into polyketide molecules.

BACKGROUND OF THE INVENTION

Polyketides are a class of compounds synthesized by the enzymatic polymerization of acetyl, proprionyl, butyryl and methoxyacetyl moieties (extender units) into a polyketide backbone through a series of decarboxylative condensation and reduction reactions and subsequent modifications. Polyketide natural products biosynthesized by polyketide synthases have diverse biological activities such as antibacterial, antifungal, anticancer, and immunosuppressant activities. Many of these products play important roles in the treatment of a variety of human diseases.

The Type I polyketide synthases are highly modular proteins. Each Type I PKS module consists of several domains with defined functions, separated by short spacer regions. Type I PKSs catalyze the biosynthesis of complex polyketides such as erythromycin and avermectin. These "modular" PKSs include assemblies of several large multifunctional proteins carrying, between them, a set of separate active sites for each step of carbon chain assembly and modification (Donadio et al., 1991, *Science* 252: 675-679; Mac-Neil et al., 1992, *Gene* 115: 119-125). The active sites required for one cycle of condensation and reduction are typically clustered as "modules". For example, 6-deoxy-erythronolide B synthase (DEBS) consists of the three multifunctional proteins, DEBS 1, DEBS 2, and DEBS 3, each of which possesses two modules that incorporate an extender unit into a polyketide chain (Caffrey et al., 1992, *FEBS Lett.* 304: 225-228).

The diverse activities of polyketides are partly due to their extensive structural diversity available via Type I PKS enzymology (FIG. 1). However, their use for medicinal purposes is being challenged by the development of resistance to these molecules by microorganisms and by cancer cells. Additionally, use of a particular polyketide for the treatment of a patient can be inhibited by unwanted side effects caused by the molecule, or the failure of the molecule to have the desired level of activity. To combat these issues, new derivatives of polyketides are needed. One approach to generate new derivatives is to modify known polyketides through synthetic or semisynthetic chemistry. While successful in many cases, the more complicated the polyketide structure, the less efficient a synthetic or semisynthetic approach is. A complementary approach is to use metabolic engineering of the polyketide biosynthetic pathway to generate new structural derivatives. Although this approach has been successful in generating new polyketides, one of the restrictions in its use has been the limited number of precursors, or extender units, which can be incorporated into a polyketide backbone by the Type I PKSs.

The flexibility of Type I PKSs has been exploited for the generation of metabolically engineered "natural" products through combinatorial biosynthesis. One example is to replace a catalytic domain from one Type I PKS with an alternative domain from a different Type I PKS, resulting in a hybrid enzyme that generates a hybrid product. This approach was shown to generate a library of nearly 60 erythromycin derivatives by exchanging catalytic domains from the erythromycin Type I PKS with catalytic domains from other Type I PKSs (McDaniel et al., 1999, *Proc. Natl. Acad. Sci. USA* 96: 1846-1851). Thus, combinatorial biosynthesis complements the more traditional approaches of using total or semisynthetic chemistry to generate structural diversity.

Changing the extender unit(s) incorporated into a polyketide can be used to vary the moiety that extends away from the backbone of the polyketide, which can have effects on its interaction with its biological target. Changes available using this approach are limited because of the limited number of known Type I PKS extender units—only four: malonyl-CoA, methylmalonyl-CoA, ethylmalonyl-CoA, and methoxymalonyl (MM)-ACP (FIG. 2). These extender units result in the incorporation of acetyl, propionyl, butyryl, or methoxyacetyl moieties into the polyketide backbone, respectively. The chemical attributes of these extender units are similar, with the exception of the potential hydrogen bonding interactions by the oxygen of the methoxy moiety. However, for all of these extender units, the moieties on the α-carbons lack simple chemical reactivity for further downstream modification by semisynthetic chemistry. Due to these limitations, there is an interest in identifying or generating new extender units with different chemical attributes to enhance structural diversification by combinatorial biosynthesis and increase the opportunities for downstream modification by semisynthetic chemistry.

The inventors of the present patent application previously published a paper proposing the existence of previously unknown hydroxymalonyl-ACP (HM-ACP), and aminomalonyl-ACP (AM-ACP) extender units (Emmert et al., 2004, *Appl. Environ. Microbiol.* 70: 104-113). In that paper, the mechanism of AM-ACP formation was proposed and has been subsequently confirmed. Although Emmert et al. proposed a mechanism for HM-ACP formation, the proposed mechanism has since been determined to be incorrect. The precursor is not glycerate, a glyceryl-CoA intermediate is not formed, and Orf2 (ZmaF) does not play a role in HM-ACP formation. Emmert et al. further proposed the minimal biosynthetic machinery for zwittermicin A assembly involving the incorporation of AM-ACP and HM-ACP, shown in FIG. 4; however, the identity of the necessary acyltransferase (AT) domains for incorporation of these extender units was not disclosed. These AT domains are the essential components needed for AM-ACP and HM-ACP recognition and incorporation. At the time, there were many potential mechanisms for AM-ACP and HM-ACP incorporation, but it was not known which mechanism was correct. In accordance with the present invention, novel enzymes responsible for the biosynthesis of zwittermicin A have been discovered.

BRIEF SUMMARY

Methods and compositions for the synthesis of polyketide synthase (PKS) enzymes are provides. Also provided are methods and compositions for the synthesis of extender units incorporated into polyketide molecules.

Isolated polynucleotides encoding polypeptides comprising amino acid sequences selected from the group consisting of: a) an amino acid sequence of SEQ ID NO:1 (i.e., Zma N), b) an amino acid sequence that is at least 90% identical to SEQ ID NO:1, and c) an amino acid sequence of a) or b) having 1 to 30 conservative amino acid substitutions, are provided. The polypeptides have phosphatase and acyltransferase activity. The polypeptides are involved in converting 1,3-bisphosphoglycerate to glyceryl-acyl carrier protein. Further provided are expression vectors that include the isolated polynucleotides. Also provided are host cells that include the expression vectors which comprise these polynucleotides. The above expression vectors may further include polynucleotides encoding polypeptides comprising the sequences of SEQ ID NO:2 (i.e., Zma D), SEQ ID NO:3 (i.e., Zma E), and SEQ ID NO:4 (i.e., Zma G). Provided are host cells that include these expression vectors. Alternatively, the expression vectors may include polynucleotides encoding polypeptides comprising sequences that are at least 90% identical to SEQ ID NO:1, SEQ ID NO:2, SEQ ID NO:3, and SEQ ID NO:4. One or more of the sequences that are at least 90% identical to SEQ ID NO:1, SEQ ID NO:2, SEQ ID NO:3 and SEQ ID NO:4 may operably be connected to separate promoters. Also provided are host cells that include these expression vectors.

Host cells are provided, which include polynucleotides encoding polypeptides comprising amino acid sequences selected from the group consisting of: a) an amino acid sequence of SEQ ID NO:1 (i.e., Zma N), b) an amino acid sequence that is at least 90% identical to SEQ ID NO:1, and c) an amino acid sequence of a) or b) having 1 to 30 conservative amino acid substitutions where the polypeptides have phosphatase and acyltransferase activity. The host cells further include expression vectors that include polynucleotides encoding polypeptides comprising the amino acids sequences of SEQ ID NO:1, SEQ ID NO:2, SEQ ID NO:3, and SEQ ID NO:4. One or more of these polynucleotides may operably be connected to separate promoters.

Isolated polypeptides comprising amino acid sequences selected from the group consisting of: a) an amino acid sequence of SEQ ID NO:1 (i.e., Zma N), b) an amino acid sequence that is at least 90% identical to SEQ ID NO:1, and c) an amino acid sequence of a) or b) having 1 to 30 conservative amino acid substitutions, are provided. The polypeptides have phosphatase and acyltransferase activity. Host cells comprising these polypeptides are also provided.

Methods are provided that include expressing, in host cells, expression vectors that comprise polynucleotides encoding polypeptides comprising amino acid sequences selected from the group consisting of: a) an amino acid sequence of SEQ ID NO:1 (i.e., Zma N), b) an amino acid sequence that is at least 90% identical to SEQ ID NO:1, and c) an amino acid sequence of a) or b) having 1 to 30 conservative amino acid substitutions, where the polypeptides have phosphatase and acyltransferase activity. In the practice of the methods, these expression vectors may express in the presence of 3-phosphoglyceric acid. The methods may further include expressing, in host cells, expression vectors that include polynucleotides encoding polypeptides comprising sequences that are at least 90% identical to SEQ ID NO:2, SEQ ID NO:3, and SEQ ID NO:4. One or more of these polynucleotides may be located on separate expression vectors. As well, each of these polynucleotides may be located on a separate expression vector.

Alternatively, the methods of the present invention may include expressing, in host cells: 1) expression vectors that comprise polynucleotides encoding polypeptides comprising amino acid sequences selected from the group consisting of: a) an amino acid sequence of SEQ ID NO:1 (i.e., Zma N), b) an amino acid sequence that is at least 90% identical to SEQ ID NO:1, and c) an amino acid sequence of a) or b) having 1 to 30 conservative amino acid substitutions, where the polypeptides have phosphatase and acyltransferase activity, and 2) expression vectors that include polynucleotides encoding polypeptides having the amino acid sequences of SEQ ID NO:2, SEQ ID NO:3, and SEQ ID NO:4. One or more of these polynucleotides may be located on separate expression vectors. As well, each of these polynucleotides may be located on a separate expression vector.

Isolated polynucleotides are provided, which encode polypeptides comprising: a) an amino acid sequence of SEQ ID NO:7 (i.e., the KS1 domain of Zma A), an amino acid sequence that is at least 90% identical to SEQ ID NO:7, or an amino acid sequence of SEQ ID NO:7 having 1-40 conservative amino acid substitutions, b) an amino acid sequence of SEQ ID NO:8 (i.e., the KR1 domain of Zma A), an amino acid sequence that is at least 90% identical to SEQ ID NO:8, or an amino acid sequence of SEQ ID NO:8 having 1-20 conservative amino acid substitutions, and c) an amino acid sequence of SEQ ID NO:9 (i.e., the ACP1 domain of Zma A), an amino acid sequence that is at least 90% identical to SEQ ID NO:9, or an amino acid sequence of SEQ ID NO:9 having 1-6 conservative amino acid substitutions, where the polypeptides have the biological activity of recognition, activation, and condensation of AM-ACP into a polyketide backbone. The present invention also provides expression vectors comprising these polynucleotides. The present invention also provides host cells that include the expression vectors comprising these polynucleotides. The host cells may further include polynucleotides encoding polypeptides comprising the amino acid sequence of SEQ ID NO:6 (i.e., Zma F), an amino acid sequence that is at least 90% identical to SEQ ID NO:6, or an amino acid sequence of SEQ ID NO:6 having 1-40 conservative amino acid substitutions, where the polypeptides have the biological activity of catalyzing the incorporation of ethanolamine subunits from AM-ACP into polyketides.

Isolated polynucleotides are provided, which encode polypeptides comprising the amino acid sequence of SEQ ID NO:5 (i.e., Zma A), an amino acid sequence that is at least 90% identical to SEQ ID NO:5, or an amino acid sequence of SEQ ID NO:5 having 1-300 conservative amino acid substitutions, where the polypeptides have the biological activity of catalyzing the incorporation of an ethanolamine subunit from AM-ACP into a polyketide. Also provided are expression vectors that include these isolated polynucleotides. Host cells are provided that include these expression vectors. The host cells may further include expression vectors comprising polynucleotides that encode polypeptides comprising the amino acid sequence of SEQ ID NO:6 (i.e., Zma F), an amino acid sequence that is at least 90% identical to SEQ ID NO:6, or an amino acid sequence of SEQ ID NO:6 having 1-40 conservative amino acid substitutions, where the polypeptides have the biological activity of catalyzing the incorporation of an ethanolamine subunit from AM-ACP into a polyketide.

Isolated polynucleotides are provided, which encode polypeptides that include: a) an amino acid sequence of SEQ ID NO:10 (i.e., the KS2 domain of Zma A), an amino acid sequence that is at least 90% identical to SEQ ID NO:10, or an amino acid sequence of SEQ ID NO:10 having 1-40 conservative amino acid substitutions, b) an amino acid sequence of SEQ ID NO:11 (i.e., the AT domain of Zma A), an amino acid sequence that is at least 90% identical to SEQ ID NO:11, or an amino acid sequence of SEQ ID NO:11 having 1-30 conservative amino acid substitutions, c) an amino acid sequence of SEQ ID NO:12 (i.e., the KR2 domain of Zma A), an amino acid sequence that is at least 90% identical to SEQ ID NO:12, or an amino acid sequence of SEQ ID NO:12 having 1-20 conservative amino acid substitutions, and d) an amino acid sequence of SEQ ID NO:13 (i.e., the ACP2 domain of Zma A), an amino acid sequence that is at least 90% identical to SEQ ID NO:13, or an amino acid sequence of SEQ ID NO:13 having 1-6 conservative amino acid substitutions. The polypeptides have the biological activity of recognition, activation, and condensation of glycolyl subunits from HM-ACP into polyketides. Further provided are expression vectors that include these polynucleotides. Also provided are host cell that include these expression vectors.

Provided are isolated polynucleotides that encode polypeptides comprising the amino acid sequence of SEQ ID NO:5, an amino acid sequence that is at least 90% identical to SEQ ID NO:5, or an amino acid sequence of SEQ ID NO:5 having 1-300 conservative amino acid substitutions, where the polypeptides have the biological activity of catalyzing the incorporation of glycolyl subunits from HM-ACP into polyketides. Provided are expression vectors that comprise these polynucleotides. Also provided are host cells comprising these expression vectors.

Methods for incorporating AM-ACP extender units into polyketide molecules are provided. The methods include reacting: 1) polypeptides comprising: a) an amino acid sequence of SEQ ID NO:7 (i.e., the KS1 domain of Zma A), an amino acid sequence that is at least 90% identical to SEQ ID NO:7, or an amino acid sequence of SEQ ID NO:7 having 1-40 conservative amino acid substitutions, b) an amino acid sequence of SEQ ID NO:8 (i.e., the KR1 domain of Zma A), an amino acid sequence that is at least 90% identical to SEQ ID NO:8, or an amino acid sequence of SEQ ID NO:8 having 1-20 conservative amino acid substitutions, and c) an amino acid sequence of SEQ ID NO:9 (i.e., the ACP1 domain of Zma A), an amino acid sequence that is at least 90% identical to SEQ ID NO:9, or an amino acid sequence of SEQ ID NO:9 having 1-6 conservative amino acid substitutions, and 2) polypeptides comprising the amino acid sequence of SEQ ID NO:6 (i.e., Zma F), an amino acid sequence that is at least 90% identical to SEQ ID NO:6, or an amino acid sequence of SEQ ID NO:6 having 1-40 conservative amino acid substitutions, with AM-ACP, where the polypeptides incorporate the AM-ACP extender units into the polyketide molecules. The methods may further include expressing polynucleotides that encode the above polypeptides in host cells. Alternatively, the methods for incorporating AM-ACP extender units into polyketide molecules may include reacting: 1) polypeptides comprising the amino acid sequence of SEQ ID NO:6 (i.e., Zma F), an amino acid sequence that is at least 90% identical to SEQ ID NO:6, or an amino acid sequence of SEQ ID NO:6 having 1-40 conservative amino acid substitutions, and 2) polypeptides comprising the amino acid sequence of SEQ ID NO:5, an amino acid sequence that is at least 90% identical to SEQ ID NO:5, or an amino acid sequence of SEQ ID NO:5 having 1-300 conservative amino acid substitutions, with AM-ACP, where the polypeptides incorporate the AM-ACP extender unit into the polyketide molecules. The methods may further include expressing polynucleotides that encode the above polypeptides in host cells.

Methods for incorporating HM-ACP extender units into polyketide molecules are provided. The methods include reacting polypeptides that comprise: a) an amino acid sequence of SEQ ID NO:10 (i.e., the KS2 domain of Zma A), an amino acid sequence that is at least 90% identical to SEQ ID NO:10, oran amino acid sequence of SEQ ID NO:10 having 1-40 conservative amino acid substitutions, b) an amino acid sequence of SEQ ID NO:11 (i.e., the AT domain of Zma A), an amino acid sequence that is at least 90% identical to SEQ ID NO:11, or an amino acid sequence of SEQ ID NO:11 having 1-30 conservative amino acid substitutions, c) an amino acid sequence of SEQ ID NO:12 (i.e., the KR2 domain of Zma A), an amino acid sequence that is at least 90% identical to SEQ ID NO:12, or an amino acid sequence of SEQ ID NO:12 having 1-20 conservative amino acid substitutions, and d) an amino acid sequence of SEQ ID NO:13 (i.e., the ACP2 domain of Zma A), an amino acid sequence that is at least 90% identical to SEQ ID NO:13, or an amino acid sequence of SEQ ID NO:13 having 1-6 conservative amino acid substitutions, with HM-ACP, where the polypeptides incorporate the HM-ACP extender units into polyketides. The methods may further include expressing polynucleotides that encode the above polypeptides in host cells.

Alternatively, the methods for incorporating HM-ACP extender units into polyketide molecules include reacting polypeptides comprising: a) the amino acid sequence of SEQ ID NO:5, b) an amino acid sequence that is at least 90% identical to SEQ ID NO:5, or c) an amino acid sequence of SEQ ID NO:5 having 1-300 conservative amino acid substitutions, with HM-ACP, where the polypeptides incorporate the HM-ACP extender units into polyketides. The methods may further include expressing polynucleotides that encode the above polypeptides in host cells.

Polyketide molecules that include one or more noncognate glycolyl subunits are provided; these polyketide molecules may be modified erythromycin PKSs. Also provided are polyketide molecules that include one or more noncognate ethanolamine subunits; these polyketide molecules may be modified erythromycin PKSs.

Host cells comprising heterologous polyketide molecules comprising one or more noncognate glycolyl subunits are provided. Also provided are host cells that include heterologous polyketide molecules comprising one or more noncognate ethanolamine subunits.

DETAILED DESCRIPTION OF THE DRAWINGS AND THE PRESENTLY PREFERRED EMBODIMENTS

Figure 1:
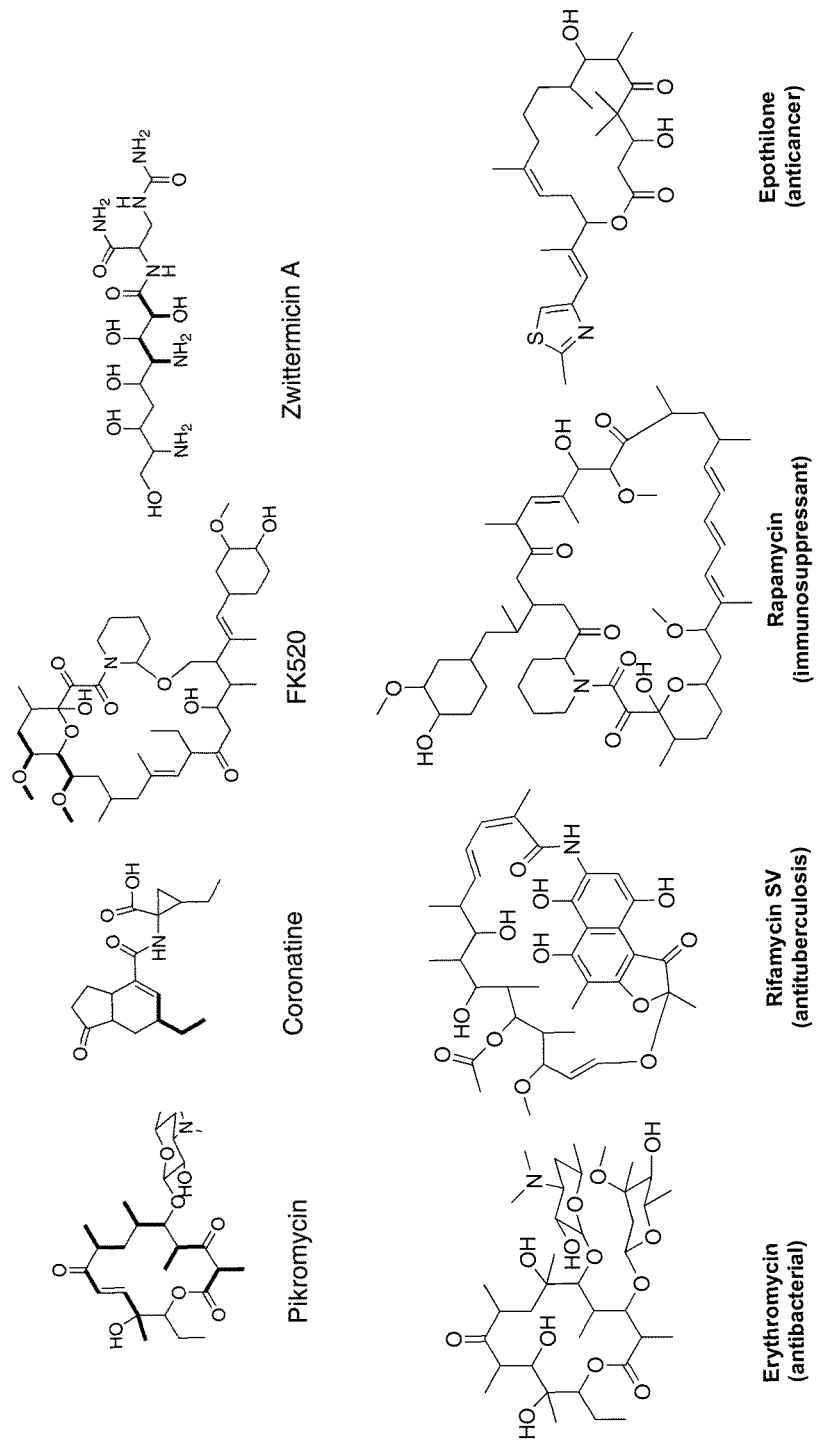
FIG. 1 shows the chemical structures of representative natural products synthesized wholly or in part by Type I PKSs.

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other organic chemistry techniques are generally performed according to Sambrook et al., 1989, Molecular Cloning—A Laboratory Manual, Cold Spring Harbor Laboratory, Cold Spring Harbor, N.Y.; Ausubel et al., 1993, *Current Protocols in Molecular Biology*, Volumes 1-3, John Wiley & Sons, Inc.; Kriegler, 1990, *Gene Transfer and Expression: A Laboratory Manual*, Stockton Press, New York; Overman, 2005, *Organic Reactions*, Wiley; and March, 1992, *Advanced Organic Chemistry: Reactions, Mechanisms and Structure*, 4th Ed., Wiley-Interscience, New York, each of which is incorporated herein by reference in its entirety.

The term "isolated polynucleotide," as used herein, means a polynucleotide of genomic, cDNA, or synthetic origin or some combination thereof, which by virtue of its origin (1) is not associated with all or a portion of a polynucleotide in which the isolated polynucleotide is found in nature, (2) is linked to a polynucleotide to which it is not linked in nature, or (3) does not occur in nature as part of a larger sequence. The term "isolated protein" or "isolated polypeptide," as used herein, means that a subject protein (1) is free of at least some other proteins with which it would typically be found in nature, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a protein with which the "isolated protein" is associated in nature, (6) is operably associated (by covalent or noncovalent interaction) with a polypeptide with which it is not associated in nature, or (7) does not occur in nature. Such an isolated protein can be encoded by genomic DNA, cDNA, mRNA or other RNA, of synthetic origin, or any combination thereof. Preferably, the isolated protein is substantially free from proteins or polypeptides or other contaminants that are found in its natural environment that would interfere with its use (therapeutic, diagnostic, prophylactic, research or otherwise). Alternatively, the isolated protein is sufficiently free from proteins or polypeptides or other contaminants that are found in its natural environment that the isolated protein is capable of being used (for therapeutic, diagnostic, prophylactic, research or other applications) in a manner that it could not be used in its natural environment.

In general, a polypeptide homolog includes any homolog in which residues at a particular position in the sequence have been substituted by other amino acids, and further includes the possibility of inserting an additional residue or residues between two residues of the parent protein as well as the possibility of deleting one or more residues from the parent sequence. Any amino acid substitution, insertion, or deletion is encompassed by the invention. In some embodiments, the amino acid substitution is a conservative substitution. Conservative substitutions whereby an amino acid of one class is replaced with another amino acid of the same type fall within the scope of the invention so long as the substitution does not materially alter the biological activity of the compound. For example, a homolog of SEQ ID NO:1 shares the same amino acid sequence as SEQ ID NO:1 except for a few amino acid differences, e.g., substitutions, insertions, or deletions. When expressed in vitro, both SEQ ID NO:1 and its homolog are expected to exhibit essentially similar function.

A single "module" of a modular PKS extender gene cluster or a modular polyketide synthase refers to sufficient portions of the extender gene cluster to encode, or sufficient portions of the polyketide synthase to include, at least the activities required to effect the condensation of a single extender unit onto a starter unit or a growing polyketide chain. At least one module for the effective synthesis of a polyketide must contain an additional AT and ACP in order to effect the initial condensation. In addition, and optionally, the module may include a ketoreductase activity (KR), a cyclase, a dehydratase (DH), an enoyl reductase (ER), and/or a thioesterase (TE).

In native forms of aromatic polyketide synthases, portions of the required activities may occur on different proteins. In the case of aromatic polyketide synthases, a ketosynthase (KS), an acyl transferase (AT) and an acyl carrier protein (ACP) must be present to effect the condensation of a single extender unit onto a starter unit or a growing polyketide. Various activities associated with reduction, cyclization, aromatization and further derivatization may also be present. There must also be at least one chain-length limiting factor (CLF).

The phrases "PKS extender gene cluster", "PKS extender unit gene cluster" and "PKS extender gene set" are used interchangeably to mean any set of PKS genes capable of producing a PKS extender unit that forms a precursor that feeds into a PKS to generate a polyketide when under the direction of one or more compatible control elements in a host cell. A functional PKS is one which catalyzes the condensation of at least one extender unit onto a growing polyketide, i.e., has at least one functional module, or extension function either in vivo or in vitro. A "PKS extender gene cluster" thus need not include all of the genes found in the corresponding cluster in nature. Furthermore, the cluster can include PKS extender unit genes derived from a single species, or may be hybrid in nature with, e.g., a coding sequence derived from a cluster for the synthesis of a particular polyketide replaced with a corresponding coding sequence from a cluster for the synthesis of another polyketide. Hybrid clusters can include genes derived from either or both modular and aromatic PKSs. The genes included in the extender unit gene cluster need not be the native genes, but can be mutants or analogs thereof. Mutants or analogs may be prepared by the deletion, insertion or substitution of one or more nucleotides of the coding sequence, by site-directed mutagenesis, or other techniques known in the art.

A "PKS extender gene cluster" may also contain genes coding for modifications to the core polyketide produced by the PKS, including, for example, genes encoding postpolyketide synthesis enzymes derived from natural products pathways such as O-methyltransferases and glycosyltransferases. A "PKS extender gene cluster" may further include genes encoding hydroxylases, methylases or other alkylases, oxidases, reductases, glycotransferases, lyases, ester or amide syntheses, and various hydrolases such as esterases and amidases. The genes included in the PKS extender gene cluster need not be on the same plasmid or, if present on the same plasmid, can be controlled by the same or different control sequences.

The cloning, analysis, and recombinant DNA technology of genes that encode PKS enzymes allow one to manipulate a known PKS extender gene cluster either to produce the polyketide synthesized by that PKS at higher levels than occur in nature or in hosts that otherwise do not produce the polyketide. The technology also allows one to produce molecules that are structurally related to, but distinct from, the polyketides produced from known PKS extender gene clusters; see, e.g., PCT publication Nos. WO 93/13663; 95/08548; 96/40968; 97/02358; 98/27203; and 98/49315; U.S. Pat. Nos. 4,874,748; 5,063,155; 5,098,837; 5,149,639; 5,672,491; 5,712,146; 5,830,750; 5,843,718; 6,274,560; 6,531,299; 6,551,802; 6,660,862; 6,750,040; 6,753,173; 6,939,691; and 7,101,684; Fu et al., 1994, Biochemistry 33: 9321-9326; McDaniel et al., 1993, *Science* 262: 1546-550; Rohr, 1995, *Angew. Chem. Int. Ed. Engl.* 34: 881-888, each of which is incorporated herein by reference.

A "host cell" is a cell and the progeny and cultures thereof derived from a prokaryotic microorganism or a eukaryotic cell line cultured as a unicellular entity, which can be, or has been, used as a recipient for recombinant vectors bearing the PKS extender gene clusters of the invention. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired PKS, are included in the definition, and are covered by the above terms. A "host cell" is a naturally occurring cell or a transformed cell that contains an isolated expression vector and supports the replication or expression of the expression vector. Host cells may be cultured cells, explants, cells in vivo, and the like. A host cell can be homologous with respect to the polypeptide that is expressed using the isolated expression vector. Alternatively, a host cell can be heterologous with respect to the polypeptide that is expressed using the expression vector. Host cells may be prokaryotic cells such as *E. Coli*, or eukaryotic cells such as yeast, insect, amphibian, or mammalian cells such as CHO, HeLa, and the like.

A "noncognate" molecule or subunit of a molecule is one that has been introduced by means of metabolic engineering and that does not exist in its native form. A noncognate subunit of a polyketide is a subunit that has been introduced into a polyketide via genetic engineering, metabolic engineering, or both. For example, a PKS enzyme may be modified so that it incorporates the noncognate subunit into a polyketide molecule.

"Metabolic engineering" refers to genetic engineering that is used to modify one or more metabolic pathways. For example, a PKS molecule can be genetically engineered to incorporate one or more noncognate subunits into a polyketide molecule, thereby synthesizing a metabolically engineered polyketide molecule.

A "functional homolog" or "functional equivalent" or "functional fragment" of a polypeptide of the present invention is a polypeptide that is homologous to the specified polypeptide but has one or more amino acid differences from the specified polypeptide. A functional fragment or equivalent of a polypeptide retains at least some, if not all, of the activity of the specified polypeptide.

In general, a PKS polypeptide functional homolog that preserves PKS polypeptide-like function includes any homolog in which residues at a particular position in the sequence have been substituted by other amino acids, and further includes the possibility of inserting an additional residue or residues between two residues of the parent protein as well as the possibility of deleting one or more residues from the parent sequence. Any amino acid substitution, insertion, or deletion is encompassed by the invention. In some embodiments, the amino acid substitution is a conservative substitution. Conservative substitutions whereby an amino acid of one class is replaced with another amino acid of the same type fall within the scope of the invention so long as the substitution does not materially alter the biological activity of the compound. For example, a functional equivalent of SEQ ID NO:1 shares the same amino acid sequence as SEQ ID NO:5 except for a few amino acid differences, e.g., substitutions, insertions, or deletions. When expressed in a cell, both SEQ ID NO:5 and its functional homolog are expected to catalyze incorporation of a glycolyl subunit into a polyketide.

A "coding sequence" or a sequence that "encodes" a protein or peptide is a nucleic acid sequence which is transcribed into mRNA (in the case of DNA) or translated into a polypeptide (in the case of mRNA) in vitro or in vivo when placed under the control of appropriate regulatory sequences.

"Control sequences" refers collectively to polynucleotide sequences that can affect expression (including transcription and translation), processing or intracellular localization of coding sequences to which they are ligated, such as, for example, promoter sequences, ribosome binding sites, polyadenylation signals, transcription termination sequences, upstream regulatory domains, enhancers, and the like. Not all of these control sequences need always be present in a recombinant vector so long as the desired gene is capable of being expressed and processed.

"Operably linked" means that the components to which the term is applied are in a relationship or configuration that allows them to carry out their usual functions under suitable conditions. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

A "library" or "combinatorial library" of polyketides is intended to mean a collection of a multiplicity of different polyketides. The differences in the members of the library may result from their being produced by different PKS systems that contain any combination of native, homolog or mutant genes from aromatic, modular or fungal PKSs. The differences in the members of the library may also result from the use of different starter units, extender units and conditions. The PKSs in the systems used to generate the library may be derived from a single system, such as act, fren, gra, tcm, whie, gris, ery, or the like, and may optionally include genes encoding tailoring enzymes which are capable of catalyzing the further modification of a polyketide. Alternatively, the combination of synthase activities can be rationally or stochastically derived from an assortment of synthases, e.g., a synthase system can be constructed to contain the KS/AT component from an act PKS, the CLF component from a gra PKS and an ACP component from a fren PKS. The synthase can optionally include other enzymatic activities as well.

The term "incorporating," as used in the context of a PKS enzyme "incorporating" an extender unit into a polyketide molecule, means that the PKS enzyme incorporates a subunit of the extender unit into the polyketide molecule. The PKS enzyme may incorporate a subunit of the extender unit into the polyketide molecule, for example, by condensation of the extender unit with a starter unit or with a previously incorporated extender unit. For example, a glycolyl subunit is incorporated into the polyketide molecule from the HM-ACP extender unit. As well, an ethanolamine subunit is incorporated into the polyketide molecule from the AM-ACP unit. The incorporation of an HM-ACP extender unit into a polyketide molecule thus refers to the incorporation of a glycolyl subunit from the HM-ACP extender unit into the polyketide molecule. As well, the incorporation of an AM-ACP extender unit into a polyketide molecule thus refers to the incorporation of an ethanolamine subunit from the AM-ACP extender unit into the polyketide molecule.

"Optional" or "optionally" means that the subsequently described event or circumstance may or may not occur, and that the description includes instances where said event or circumstance occurs and instances where it does not. For example, the phrase "optionally further purified" means that further purification may or may not be performed and that the description includes both the performance and the lack of performance of such further purification.

As used in this specification and the appended claims, the singular forms "a," "an" and "the" include plural references unless the content clearly dictates otherwise. Thus, reference to "a polyketide synthase" includes mixtures of polyketide synthases; reference to "an extender unit" includes mixtures of such extender units, and the like.

FIG. 1 shows structures of representative natural products synthesized wholly or in part by Type I PKSs. Bold carbons and bonds in the structures denote selected components derived from different extender units: (i) pikromycin, malonyl-CoA and methylmalonyl-CoA; (ii) coronatine, ethylmalonyl-CoA; (iii) FK520, methoxymalonyl-acyl carrier protein (MM-ACP); and (iv) zwittermicin.

Figure 2:
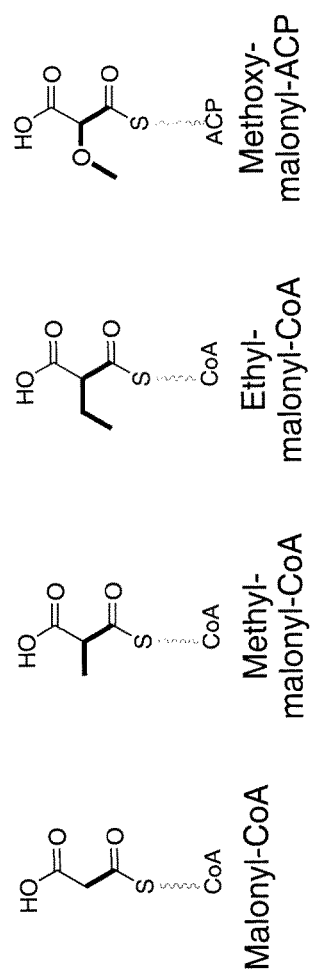
FIG. 2 illustrates the chemical structures of known Type I PKS extender units.
Figure 3:
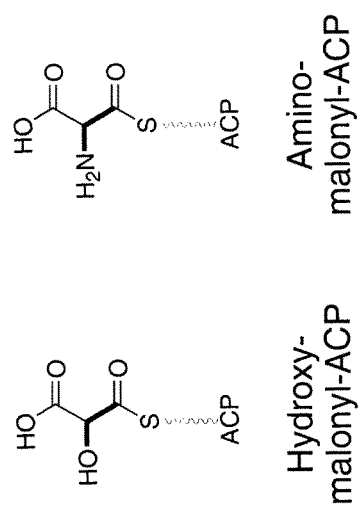
FIG. 3 illustrates the chemical structures of two novel Type I polyketide synthase extender units of this invention, hydroxymalonyl-ACP (HM-ACP), and aminomalonyl-ACP (AM-ACP).

FIG. 2 illustrates the chemical structures of known Type I PKS extender units. The SH-CoA squiggle bond illustrates coenzyme A; the SH-ACP squiggle bond illustrates 4'-phosphopantetheinyl-ACP. Two novel extender units for Type I polyketide synthases are provided: (1) hydroxymalonyl-acyl carrier protein (hydroxymalonyl-ACP; HM-ACP), and (2) aminomalonyl-acyl carrier protein (aminomalonyl-ACP, AM-ACP (FIG. 3; see also Chan et al., 2006, Proc. Natl. Acad. Sci. U.S.A. 103: 14349-14354). These extender units have chemical attributes that are unique compared to those extender units that were previously known for the synthesis of polyketides. Provided herein is biochemical and mass spectral evidence for the existence of two novel Type I PKS extender units, HM-ACP and AM-ACP. This is the first empirical evidence for the formation of ACP-linked Type I PKS extender units. Additionally, in one embodiment this invention provides that 1,3-bPG is the likely in vivo precursor for the formation of HM-ACP and MM-ACP.

In one embodiment, this invention provides for the introduction of HM-ACP, AM-ACP extender units, or both, into a desired polyketide. Any one of these Type I polyketide synthase extender units may be incorporated into any polyketide for the purpose of generating new structural derivatives. For example, these may be derivatives of medically or agriculturally important polyketide-containing natural products. In one aspect, this invention provides the enzymes for achieving the introduction of HM-ACP and/or AM-ACP extender units into polyketides.

It is also possible to use the extender units of this invention for metabolic engineering of a portion of the erythromycin Type I PKS. The erythromycin Type I PKS can be engineered to incorporate HM-ACP or AM-ACP extender units. In one example of this invention, in vivo or in vitro erythromycin derivatives are produced, which incorporate HM-ACP and AM-ACP extender units into the polyketide backbone of this important antibiotic.

Provided also is the ability to introduce hydroxyl or amino group functionality into the polyketide backbone of a Type I polyketide-based product. Thus, in one aspect this invention expands the metabolic engineering potential of Type I PKSs, thereby introducing unprecedented structural diversity into the polyketide products, natural or synthetic.

In one embodiment, this invention provides a gene, zmaN, coding for a homolog of an FkbH protein. The newly isolated gene zmaN encodes a protein ZmaN. The amino acid sequence of ZmaN is shown as SEQ ID NO:1. This sequence has been deposited on Jun. 28, 2006 in the GenBank under accession number DQ830808. An identified function of zmaN is to convert 1,3-bisphosphoglycerate to glyceryl-acyl carrier protein. ZmaN functions as a phosphatase and acyltransferase, and is involved in hydroxymalonyl-acyl carrier protein formation.

The incorporation of AM-ACP and HM-ACP into a desired polyketide backbone requires not only the enzymology needed to form these unusual extender units, but also the enzymology for recognition, activation, and condensation of these extender units into the growing polyketide backbone. The enzymes that catalyze these steps are polyketide synthases (PKSs). The PKS that incorporates AM-ACP and HM-ACP is contained on two polypeptides, ZmaA (SEQ ID NO:5) and ZmaF (SEQ ID NO:6), obtained from Bacillus cereus. Thus, in one embodiment, this invention provides a gene, zmaA, coding for the protein ZmaA. The amino acid sequence of ZmaA is shown as SEQ ID NO:5. ZmaA is an eight-domain protein, which, in combination with ZmaF, is involved in the recognition, activation and condensation of AM-ACP into the polyketide backbone. The domains of the ZmaA protein are, in the following order: ketosynthase (KS1) (SEQ ID NO:7), consisting of amino acids 1-438; linker, consisting of amino acids 439-1001; ketoreductase (KR1) (SEQ ID NO:8), consisting of amino acids 1002-1203; linker, consisting of amino acids 1204-1287; acyl carrier protein (ACP1) (SEQ ID NO:9), consisting of amino acids 1288-1352; linker, consisting of amino acids 1353-1374; ketosynthase (KS2) (SEQ ID NO:10), consisting of amino acids 1375-1800; linker, consisting of amino acids 1801-1897; acyltransferase (AT) (SEQ ID NO:11), consisting of amino acids 1898-2205; linker, consisting of amino acids 2206-2521; ketoreductase (KR2) (SEQ ID NO:12), consisting of amino acids 2522-2719; linker, consisting of amino acids 2720-2810; acyl carrier protein (ACP2) (SEQ ID NO:13), consisting of amino acids 2811-2875; linker, consisting of amino acids 2876-2891; condensation (C) domain, consisting of amino acids 2892-3336 (end). The linker domains are typically considered as being the sites of domain fusions. The linker domains are typically not drawn when representing PKS systems.

The following three domains are required for incorporation of AM-ACP into a polyketide: (i) ketosynthase (KS1), consisting of amino acids 1-438 (SEQ ID NO:7); (ii) ketoreductase (KR1) (SEQ ID NO:8), consisting of amino acids 1002-

1203; and (iii) acyl carrier protein (ACP1), consisting of amino acids 1288-1352 (SEQ ID NO:9). Incorporation of AM-ACP into a polyketide also requires the presence of ZmaF, in combination with the above KS1, KR1, and ACP1 domains of ZmaA.

ZmaA is involved in the recognition, activation, and condensation of HM-ACP into the polyketide backbone. The following four domains are required for incorporation of HM-ACP into a polyketide: (i) ketosynthase (KS2), consisting of amino acids 1375-1800 (SEQ ID NO:10); (ii) acyltransferase (AT), consisting of amino acids 1898-2205 (SEQ ID NO:11); (iii) ketoreductase (KR2), consisting of amino acids 2522-2719 (SEQ ID NO:12); and (iv) acyl carrier protein (ACP2), consisting of amino acids 2811-2875 (SEQ ID NO:13).

ZmaF is an acyltransferase. The amino acid sequence of ZmaF is shown as SEQ ID NO:6.

ZmaA and ZmaF are unique in being the only known PKS for incorporation of AM-ACP and HM-ACP into polyketides. The AT domains from ZmaF and ZmaA are unique and give insights into how to adjust a PKS system to incorporate AM-ACP or HM-ACP components.

In the case of recombinantly expressed polynucleotides of the present invention, the polynucleotides sequences can be expresses using one expression vector. When one expression vector is used, one or more polynucleotide sequences can be expressed using one or more regulatory sequences, such as promoters. For example, one promoter can regulate the expression of one or more polynucleotide sequences. As well, individual promoters can separately regulate the expression of polynucleotide sequences of the present invention. For example, if a vector includes three polynucleotide sequences, the expression of each of the three polynucleotide sequences can be independently regulated using a separate promoter. The promoters can be identical. Alternatively, the promoters can be different, and, in the example above, the expression of each of the three polynucleotide sequences can be regulated by completely differing promoters. Combinations of these approaches can be used as well.

Alternatively, the sequences of the recombinantly expressed polynucleotides can be expressed using multiple expression vectors. Thus, for practicing the present invention, two or more vectors, where each vector expresses different nucleotides, can be designed. Each of these vectors can express one or more polypeptides of the present invention. Each of these vectors can include one or more regulatory sequences, e.g. promoters, which are operably connected to the polynucleotide sequences of the present invention.

In the case of recombinantly expressed polypeptides, various embodiments are contemplated. In some embodiments, the present invention contemplates recombinant expression of the entire sequences of the polypeptides of this invention, such as ZmaN, ZmaD, ZmaE, ZmaG, ZmaA, and ZmaF, or variations thereof. In other embodiments, the present invention contemplates recombinant expression of the amino acid sequences of individual domains of the polypeptides of the present invention, or variations thereof. For example, one or more expression vectors can be used to recombinantly express individually, or in any desirable groups, polynucleotide sequences encoding the amino acid domain sequences of ZmaA. Thus, in one embodiment, a skilled artisan can express each of the KS1, KR1, ACP1, KS2, AT, KR2, ACP2 domains of ZmaA individually, or in any desired combination. Such domains can be expressed from one expression vector, or from multiple expression vectors. The same is also true for variants of these domains.

Host cells can be transformed or transfected using one or more expression vectors, which can express a variety of the polypeptides of this invention. Thus, a host cell can be engineered to express: (i) one or more of the ZmaF domains, or variants thereof; (ii) one or more polypeptides ZmaN, ZmaD, ZmaE, ZmaG, ZmaA, and ZmaF, or variations thereof; (iii) or any combinations thereof. To practice the methods of the present invention, it is also contemplated that one or more isolated polypeptides of the present invention can be introduced into a host cell, where the polypeptide(s) can react with other molecules, enzymes, and/or substrates.

In the case of recombinant polynucleotides of the present invention, the sequence of the recombinant polynucleotide need not be exactly identical to the corresponding isolated sequence. The introduced recombinant polynucleotide sequence will typically be substantially identical to the corresponding isolated sequence.

Two nucleic acid sequences or polypeptides are said to be "identical" if the sequence of nucleotides or amino acid residues in the two sequences is the same when aligned for maximum correspondence as described below. The term "complementary to" is used herein to mean that the sequence is complementary to all or a portion of a reference polynucleotide sequence.

Optimal alignment of sequences for comparison may be conducted by methods commonly known in the art, e.g., the local homology algorithm (Smith and Waterman, 1981, *Adv. Appl. Math.* 2:482-489), by the search for similarity method (Pearson and Lipman, 1988, *Proc. Natl. Acad. Sci. USA*. 85: 2444-2448), by computerized implementations of these algorithms (GAP, BESTFIT, BLAST, FASTA, and TFASTA in the Wisconsin Genetics Software Package, Genetics Computer Group (GCG), Madison, Wis.), or by inspection. Protein and nucleic acid sequence identities may be evaluated using the Basic Local Alignment Search Tool ("BLAST") which is well known in the art (Karlin and Altschul, 1990, *Proc. Natl. Acad. Sci. USA* 87: 2267-2268; Altschul et al., 1997, *Nucl. Acids Res.* 25: 3389-3402) the disclosures of which are incorporated by reference in their entireties. The BLAST programs identify homologous sequences by identifying similar segments, which are referred to herein as "high-scoring segment pairs," between a query amino or nucleic acid sequence and a test sequence which is preferably obtained from a protein or nucleic acid sequence database. The statistical significance of a high-scoring segment pair can be evaluated using the statistical significance formula (Karlin and Altschul, 1990), the disclosure of which is incorporated by reference in its entirety. The BLAST programs can be used with the default parameters or with modified parameters provided by the user.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 25% sequence identity. Alternatively, percent identity can be any integer from 25% to 100%. More preferred embodiments include at least: 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98% or 99% identity compared to a reference sequence using the programs described herein; preferably BLAST using standard parameters, as described. One of skill will recognize that these values can be appropriately adjusted to determine corresponding identity of proteins encoded by two nucleotide sequences by taking into account codon degeneracy, amino acid similarity, reading frame positioning and the like.

Substantial identity of amino acid sequences for these purposes normally means sequence identity of at least 40%. Preferred percent identity of polypeptides can be any integer from 40% to 100%. More preferred embodiments include at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% identity compared to a reference sequence using the programs described herein; preferably BLAST using standard parameters, as described. Polypeptides that are "substantially similar" share sequences as noted above except that residue positions which are not identical may differ by conservative amino acid changes.

Conservative amino acid substitutions refer to the interchangeability of residues having similar side chains and preferably have similar physical/chemical properties. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine. Accordingly, polynucleotides of the present invention encoding a polypeptide of the present invention include nucleic acid sequences that encode polypeptides with one or more conservative amino acid substitutions.

The number of conservative amino acid substitutions is any integer from 1 to 1000. For example, with respect to SEQ ID NO:1, which has 359 amino acids, the number of conservative amino acid substitutions is 1 to 30 conservative amino acid substitutions, e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, substitutions. In another example, with respect to SEQ ID NO:6, which has 3336 amino acids, the number of conservative amino acid substitutions is 1 to 300 conservative amino acid substitutions, e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 110, 120, 130, 140, 150, 160, 170, 180, 190, 200, 210, 220, 230, 240, 250, 260, 270, 280, 290, 300 substitutions. Polypeptides or proteins of the present invention thus include amino acid sequences that have substantial identity to the amino acid sequences of the present invention.

In one embodiment, the invention also relates to nucleic acids that selectively hybridize to the exemplified sequences, including hybridizing to the exact complements of these sequences. The specificity of single stranded DNA to hybridize complementary fragments is determined by the "stringency" of the reaction conditions. Hybridization stringency increases as the propensity to form DNA duplexes decreases.

In nucleic acid hybridization reactions, the stringency can be chosen to favor specific hybridizations (high stringency), which can be used to identify, for example, full-length clones from a library. Less-specific hybridizations (low stringency) can be used to identify related, but not exact, DNA molecules (homologous, but not identical) or DNA segments.

DNA duplexes are stabilized by: (1) the number of complementary base pairs, (2) the type of base pairs, (3) salt concentration (ionic strength) of the reaction mixture, (4) the temperature of the reaction, and (5) the presence of certain organic solvents, such as formamide, which decreases DNA duplex stability. In general, the longer the probe, the higher the temperature required for proper annealing. A common approach is to vary the temperature: higher relative temperatures result in more stringent reaction conditions. Ausubel et al. (1993) provide an excellent explanation of the stringency of hybridization reactions.

To hybridize under "stringent conditions" describes hybridization protocols in which nucleotide sequences at least 60% homologous to each other remain hybridized. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium.

"Stringent hybridization conditions" are conditions that enable a probe, primer or oligonucleotide to hybridize only to its target sequence. Stringent conditions are sequence-dependent and will differ. Stringent conditions comprise: (1) low ionic strength and high temperature washes (e.g. 15 mM sodium chloride, 1.5 mM sodium citrate, 0.1% sodium dodecyl sulfate at 50° C.); (2) a denaturing agent during hybridization (e.g. 50% (v/v) formamide, 0.1% bovine serum albumin, 0.1% Ficoll, 0.1% polyvinylpyrrolidone, 50 mM sodium phosphate buffer (pH 6.5; 750 mM sodium chloride, 75 mM sodium citrate at 42° C.); or (3) 50% formamide. Washes typically also comprise 5×SSC (0.75 M NaCl, 75 mM sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. Preferably, the conditions are such that sequences at least about 65%, 70%, 75%, 85%, 90%, 95%, 98%, or 99% homologous to each other typically remain hybridized to each other. These conditions are presented as examples and are not meant to be limiting.

"Moderately stringent conditions" use washing solutions and hybridization conditions that are less stringent (Sambrook et al, 1989), such that a polynucleotide will hybridize to the entire, fragments, derivatives, or analogs of that polynucleotide. One example comprises hybridization in 6×SSC, 5×Denhardt's solution, 0.5% SDS and 100 mg/ml denatured salmon sperm DNA at 55° C., followed by one or more washes in 1×SSC, 0.1% SDS at 37° C. The temperature, ionic strength, and other conditions can be adjusted to accommodate experimental factors such as probe length. Other moderate stringency conditions have been described (Ausubel et al., 1993; Kriegler, 1990).

"Low stringent conditions" use washing solutions and hybridization conditions that are less stringent than those for moderate stringency (Sambrook et al., 1989), such that a polynucleotide will hybridize to the entire, fragments, derivatives, or analogs of that polynucleotide. A non-limiting example of low stringency hybridization conditions includes hybridization in 35% formamide, 5×SSC, 50 mM Tris HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris HCl (pH 7.4), 5 mM EDTA, and 0.1% SDS at 50° C. Other conditions of low stringency, such as those for cross species hybridizations are well-described (Ausubel et al., 1993; Kriegler, 1990).

The extender units of this invention can be used for combinatorial biosynthesis of Type I polyketide synthases (PKSs). Thus, in one example, this invention provides a method for the generation of new structural derivatives of polyketide-containing natural products. Changing one or more of the extender units incorporated into a polyketide backbone can alter the structure and activity of a natural product such as a polyketide. The polyketide products may be further modified, typically by hydroxylation, oxidation and/or glycosylation, in order to exhibit desired functionality, e.g. antibiotic activity. Methods for glycosylating polyketides are generally known in the art; the glycosylation may be effected intracellularly by providing the appropriate glycosylation enzymes or may be effected in vitro using chemical synthetic means.

The two novel extender units of the present invention are utilized by *Bacillus cereus* for the biosynthesis of zwittermicin A (ZMA). Thus, in one example of the present invention, these extender units can be used for in vitro biosynthesis of zwittermicin A.

These extender units are of significant interest because they introduce unique hydrogen-bonding characteristics and chemical reactivity to the moiety tethered to the C2 of the extender unit. These extender units offer unique possibilities for combinatorial biosynthesis and semisynthetic chemistry due to the introduction of free hydroxyl and amino moieties into a polyketide structure. Harnessing the biosynthetic potential of these two Type I PKS extender units substantially increases the ability to introduce new structural diversity into polyketides.

Biochemical and mass spectral evidence for the formation of these extender units is also provided. This is the first direct evidence for the formation of ACP-linked extender units for polyketide synthesis. Interestingly, aminomalonyl-ACP formation involves enzymology typically found in nonribosomal peptide synthesis. The AM-ACP pathway uses NRPS enzymology (an adenylation and carrier protein pair) for the formation of a Type I PKS extender unit. Thus, AM-ACP can function as an NRPS extender unit in other enzyme systems. For example, the antibiotic GE23077 is a cyclic nonribosomal peptide that contains an aminomalonate residue. Therefore, AM-ACP has the potential to function as a Type I PKS or an NRPS extender unit.

In one embodiment, this invention provides for metabolic engineering of rifamycin production using the extender units of this invention. Rifamycin is an essential first-line drug against *M. tuberculosis* infections and new derivatives of this PKS-synthesized antibiotic are needed.

In another embodiment, this invention provides for metabolic engineering of Type I PKSs by changing the extender unit incorporated by a particular Type I PKS module. This approach involves replacing the catalytic domain that controls extender unit recognition and incorporation by a particular PKS module with the corresponding catalytic domain that recognizes a different extender unit. This domain is called the acyltransferase (AT) domain. Thus, to introduce an alternative PKS extender unit into a target Type I PKS, an AT domain that recognizes and incorporates the alternative extender unit must be identified. Type I PKS involved in ZMA biosynthesis may contain AT domains that recognize and incorporate HM-ACP and AM-ACP extender units (FIG. 7). To harness this metabolic engineering potential, the portability of these domains can be used into alternative Type I PKSs to generate novel hybrid molecules.

FIG. 7 shows ESI-FT-ICR-MS spectra of the intermediates in HM-ZmaD formation. The top of FIG. 7 depicts ZmaD intermediates of interest (from left to right: apo-, holo-[+340 Da], glycolyl-[+398 Da], glyceryl-[+428 Da], and HM-ZmaD [+442 Da]) and alignment to the representative peaks in the mass spectra as indicated by vertical dashed lines. Shown are the loading and corresponding mass shifts (1015-1070 m/z, +12 ions converted to mass scale) of (A) apo-ZmaD; (B) holo-ZmaD; (C) glyceryl-ZmaD; (D) HM-ZmaD; asterisks indicate signals arising from artifactual adduction: sodium (+22 Da), potassium (+38 Da), phosphate (+98 Da), and oxidation of Met/Cys residues (+16 Da). Insets show mass spectra and structures of 4'-Ppant (phosphopantetheinyl) elimination product.

It is to be understood that this invention is not limited to the particular methodology, protocols, subjects, or reagents described, and as such may vary. It is also to be understood that the terminology used herein is for the purpose of describing particular embodiments only, and is not intended to limit the scope of the present invention, which is limited only by the claims. The following examples are offered to illustrate, but not to limit the claimed invention.

EXAMPLES

Cloning of Biosynthetic Genes

Standard PCR-based cloning was used to introduce zmaD, zmaE, zmaG, zmaH, zmaI, zmaJ, and zmaN into the *Escherichia coli* overexpression vector pET28b (Novagen, Madison, Wis.). All expression vector clones result in the production of a protein with an N-terminal histidine tag. All clones were verified by sequencing at the University of Wisconsin Biotechnology Sequencing Center.

Heterologous Overproduction of Proteins

All expression constructs were introduced into *E. coli* BL21 (λDE3). For overproduction of ZmaD, ZmaG, ZmaH, ZmaJ, and ZmaN, cells were grown at 25° C. in LB medium containing 50 μg/ml of kanamycin. At an $OD_{600}$ of 0.4-0.6, the temperature was reduced to 15° C., and cells were grown for 1.5-2.5 hours. Isopropyl-D-thiogalactopyranoside (IPTG) was then added to 60 μM, and the cells were grown an additional 16 hours at 15° C. For overproduction of ZmaE and ZmaI, cells were grown at 25° C. for 24 hours in LB medium containing 50 μg/ml of kanamycin without IPTG addition. Cells were harvested by centrifugation.

Purification of Proteins

Cells were resuspended in histidine-tag purification buffer (20 mM Tris pH 8, 300 mM NaCl, 10% [v/v] glycerol; for ZmaG: 20 mM Tris pH 8, 300 mM NaCl, 10% [w/v] sucrose). Cells were broken by sonication, and cell debris was removed by centrifugation. Imidazole was added to the cell-free extract to 5 mM, and the mixture was incubated with 1-2 ml of Ni-NTA agarose resin (Qiagen, Valencia, Calif.) for 1-2 hours at 4° C. with gentle rocking. The resin was collected by centrifugation and loaded into a column. The resin was washed with histidine-tag buffer containing 5 mM imidazole, and stepwise elutions were performed with buffer containing increasing imidazole concentrations (20, 40, 60, 100, 250 mM).

Fractions containing purified protein based on SDS-PAGE/Coomassie blue staining were pooled and dialyzed at 4° C. in dialysis buffer (50 mM Tris pH 8, 100 mM NaCl, and 10% [v/v] glycerol; for ZmaG: 50 mM Tris pH 8, 100 mM NaCl, and 10% [w/v] sucrose; for ZmaI: 50 mM Tris pH 8, 300 mM NaCl, and 10% [v/v] glycerol). ZmaE was dialyzed further in high salt buffer (50 mM Tris pH 8, 300 mM NaCl, and 10% [v/v] glycerol) and ZmaI was dialyzed in high salt buffer containing 100 µM FAD for 5 hours and then in high salt buffer lacking FAD. All proteins were concentrated, flash frozen with liquid nitrogen, and stored at −80° C. Protein concentrations were determined by the calculated molar extinction coefficients (ZmaD, 2,560 $M^{-1}$ $cm^{-1}$; ZmaE, 44,410 $M^{-1}$ $cm^{-1}$; ZmaG, 21,180 $M^{-1}$ $cm^{-1}$; ZmaH, 2,560 $M^{-1}$ $cm^{-1}$; ZmaI, 44,770 $M^{-1}$ $cm^{-1}$; ZmaJ, 46760 $M^{-1}$ $cm^{-1}$; ZmaN, 41,070 $M^{-1}$ $cm^{-1}$).

Phosphopantetheinylation of ZmaD and ZmaH

Sfp from *Bacillus subtilis* was used for apo- to holo-ACP conversion as previously described (Quadri et al., 1998, *Biochemistry* 37: 1585-1595). Each reaction mixture contained 12.5 µM apo-ACP, 75 mM Tris pH 7.5, 10 mM $MgCl_2$, 1 mM tris(2-carboxyethylphosphine) (TCEP), 50 or 500 µM CoA, and 1 µM Sfp, and was incubated at 22° C. for 1 hour.

Formation of Glyceryl-ZmaD

Reactions with 3-PG (130 or 260 µl) contained: 10 µM holo-ZmaD, 58 mM Tris pH 7.5, 8 mM $MgCl_2$, 0.8 mM TCEP, 385 µM CoA, 0.8 µM Sfp, 250 µM D(−)$_3$—PG (Sigma, St. Louis, Mo.), 5 mM ATP, and 1 µM ZmaN, and were run for 40 min at 22° C. Control reactions were run without ZmaN, ATP, or with 2 U of 3-PGPK (Sigma). A time course comparing reactions with and without 3-PGPK contained 50 µM 3-PG, and the reactions were run for 0.5, 2.0, 5.0, and 10 min.

Reactions containing glyceraldehyde-3-phosphate (150 µl final volume) contained: 12.5 µM holo-ZmaD, 75 mM Tris pH 7.5, 10 mM $MgCl_2$, 1 mM TCEP, 100 mM NaCl, 500 µM CoA, 1 µM Sfp, 250 µM DL-glyceraldehyde-3-phosphate (Sigma), 1 U GAPDH (Sigma), and 1 µM ZmaN were run for 40 min at 22° C. Control reactions without GAPDH, DL-glyceraldehyde-3-phosphate, Sfp, or ZmaN were run, as well as control reactions in which holo-ZmaH replaced holo-ZmaD.

Formation of Seryl-ZmaH

Reaction mixtures (130 or 260 µl) contained: 10 µM holo-ZmaH, 58 mM Tris pH 7.5, 8 mM $MgCl_2$, 0.8 mM TCEP, 385 µM CoA, 0.8 µM Sfp, 250 µM L-serine, 5 mM ATP, and 1 µM ZmaJ. The reaction mixtures were incubated at 22° C. for 1 hour. To test whether seryl-ZmaD could be formed, 10 µM holo-ZmaD replaced the 10 µM holo-ZmaH in a 130 µL reaction mixture.

Formation of AM-ZmaH

Reaction mixtures (130 or 260 µL) contained the following components: 10 µM ZmaD, 58 mM Tris pH 7.5, 8 mM $MgCl_2$, 0.8 mM TCEP, 385 µM CoA, 0.8 µM Sfp, 250 µM L-serine, 5 mM ATP, 1 µM ZmaJ, 1 µM ZmaG, 200 µM $NAD^+$, 1 µM ZmaI, and 100 µM FAD. The reaction mixtures were run for 5 or 40 min at 22° C. Reactions were repeated without ZmaG, ZmaI, or replacing ZmaI with 1 µM ZmaE.

High-Performance Liquid Chromatography (HPLC) Analysis of ZmaD and ZmaH Reaction Products HPLC analysis of enzymatic reaction products was performed with a Vydac C18 peptide column (250×4.6 mm; Grace Vydac, Deerfield, Ill.). In this experiment, 100-200 µl of apo- or holo-ZmaD or 130-200 µl of acylated ZmaD reactions were injected, and products were separated using a 20-80% acetonitrile, 0.1% TFA gradient over 20 min at a flow rate of 1 ml/min; elution was monitored at A220. In this experiment, 100-200 µl of apo- or holo-ZmaH or 130-200 µl of aminoacylated ZmaH reaction products was injected, and products were separated using the same method as above.

Matrix-Assisted Laser Desorption Time-of-Flight Mass Spectrometry (MALDI-TOF MS) Analysis of ZmaD and ZmaH Reaction Products The enzymatic reaction products were collected as they eluted from the HPLC, flash frozen with $CO_2$(s)/ethanol (95%), and lyophilized overnight. Lyophilized samples were resuspended in dd$H_2O$ and added to 1 µL of the sinipinic acid matrix (10 mg/ml in 50% acetonitrile, 0.05% TFA). MALDI-TOF MS analysis was performed using a Voyager™ Biospectrometry™ Workstation (DE Pro) in linear mode (Applied Biosystems, Foster City, Calif.). Calibration was performed using apomyoglobin, bovine insulin, and cytochrome C (Sigma).

ATP-PPi Exchange Assays for ZmaJ

ZmaJ used in these assays was purified by an additional anion exchange chromatography step, which had no effect on seryl-ZmaH formation. ATP-PPi exchange assays were performed as previously described (Thomas et al., 2002, *Chem. Biol.* 9: 171-184). Reactions for amino acid specificity contained 70 nM ZmaJ and 1 mM of the following amino acids: L-Ser, L-2,3-diaminopropionate, L-Thr, Gly, and L-Cys. To determine the kinetic parameters of ZmaJ activation of L-Ser, 100 µL reactions containing 70 nM ZmaJ, 3.5 mM ATP, and varying concentrations of L-Ser (0.35 to 10 mM), in triplicate, were incubated for 10 min prior to stopping the reactions. The reactions were in the linear range for enzyme concentration and less than 10% substrate-to-product conversion.

Analysis of Samples by Electrospray Ionization-Fourier Transform Ion Cyclotron Resonance Mass Spectrometry (ESI-FT-ICR-MS)

Mass analysis was performed on a custom-built 8.5 T Quadrupole-enhanced Fourier Transform Ion Cyclotron Resonance Mass Spectrometer (Q-FTMS) of the Marshall design. In general, a sample of interest was introduced to the mass spectrometer using a NanoMate 100 for automated nanospray (Advion Biosciences, Ithaca, N.Y.). Targeted species were externally accumulated in an octopole ion trap and either transferred to the ion cyclotron resonance (ICR) cell, isolated by Stored Waveform Inverse Fourier Transform (SWIFT), and fragmented by Infrared Multiphoton Dissociation (IRMPD) or fragmented in the trap (OCAD) and then transferred to the ICR cell for mass measurement. Collected data were analyzed using THRASH and/or manually interpreted, producing sets of intact mass data and fragment ion peak lists, which were uploaded onto the ProSightP™ (Taylor et al., 2003, *Anal. Chem.* 75: 4081-4086) web server for analysis in single protein mode. The protocol for 4'-Ppant elimination is described in (Dorrestein et al., 2006, *Biochemistry* 45: 12756-12766). All ESI-FT-ICR-MS experiments for glyceryl-ZmaD and HM-ZmaD used 3-PG as the starting substrate.

Bioinformatics Analysis and Protein Purification

A set of five proteins is predicted to be involved in the formation of MM-ACP, an extender unit needed for the biosynthesis of FK520 (Wu et al., 2000, *Gene* 251: 81-90) (FIGS. 1B, 5A). This proposal is based on bioinformatics analysis of the FK520 biosynthetic gene cluster as well as biosynthetic gene clusters for other methoxyacetyl-containing natural products.

Figure 5:
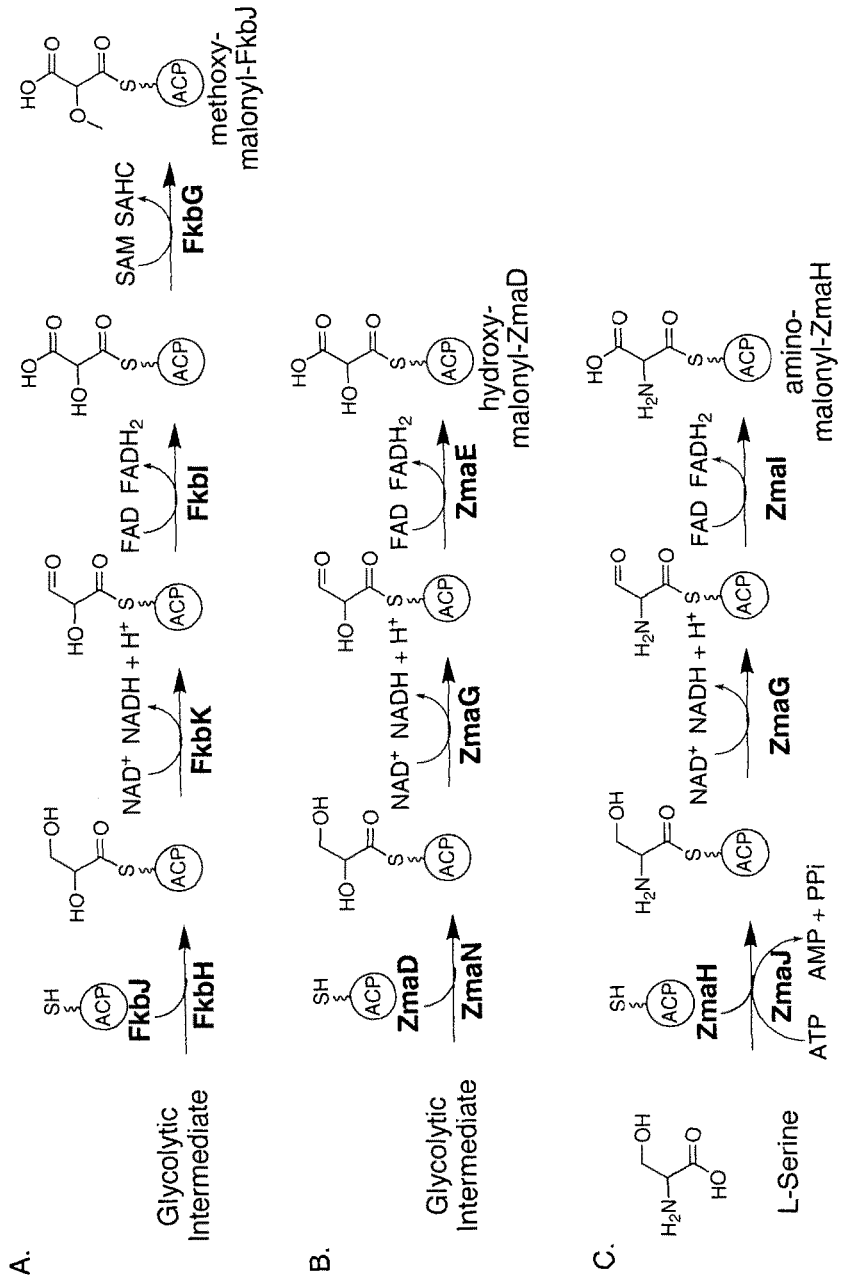
FIG. 5 illustrates possible pathways for ACP-linked PKS extender units.

FIG. 5 illustrates proposed pathways for ACP-linked PKS extender units. FIG. 5A illustrates MM-ACP formation during FK520 biosynthesis. FIG. 5B illustrates HM-ACP formation during ZMA biosynthesis. FIG. 5C illustrates AM-ACP formation during ZMA biosynthesis. The squiggles in the chemical structures shown in FIG. 5 denote the 4'-Ppant prosthetic groups of the ACPs. For correlating previous Orf names (Emmert et al., 2004, *Appl. Environ. Microbiol.* 70: 104-113) to those shown above, the nomenclature is: ZmaD, Orf3; ZmaE, Orf1; ZmaG, Orf4; ZmaH, Orf5; ZmaI, Orf6; ZmaJ, Orf7.

The proposed MM-ACP pathway is as follows (using FK520 protein nomenclature) (FIG. 5A): 1) FkbH binds to a glycolytic intermediate and dephosphorylates it while tethering it to an ACP, FkbJ, forming glyceryl-ACP; 2) FkbK catalyzes the oxidation of the glyceryl-ACP to 2-hydroxy-3-oxopropionyl-ACP (or 2,3,3-trihydroxypropionyl-ACP); 3) FkbI converts the FkbK product to HM-ACP; and 4) FkbG catalyzes the O-methylation to form MM-ACP. During ansamitosin biosynthesis O-methylation occurs prior to incorporation by the PKS, therefore MM-ACP is the in vivo extender unit, and not HM-ACP (Carroll et al., 2002, *J. Am. Chem. Soc.* 124: 4176-4177). While genetic experiments support the hypothesis that these enzymes are involved in the incorporation of a MM-ACP extender unit, and a crystal structure of FkbI has been determined, biochemical evidence for MM-ACP has yet to be provided.

A part of the ZMA biosynthetic pathway was analyzed, and five genes were identified, which were coding for homologs of the MM-ACP pathway from FK520 (Emmert et al., 2004, *Appl. Environ. Microbiol.* 70: 104-113). Through sequencing of the ZMA biosynthetic gene cluster a gene, zmaN, coding for a homolog of FkbH, was identified. Thus, the ZMA biosynthetic gene cluster codes for one homolog of both FkbH and FkbK, and two homologs of FkbJ and FkbI. An FkbG homolog is not coded within the biosynthetic gene cluster. The presence of two homologs of the ACP that is proposed to carry the methoxymalonyl moiety for the MM-ACP extender unit points to the existence of two ACP-linked Type I PKS extender units for ZMA production.

One of these extender units, HM-ACP, can be generated in a similar manner to that proposed for MM-ACP, but lack of an FkbG homolog results in the formation of HM-ACP (FIG. 5B). The second, aminomalonyl-ACP pathway, possibly involves an enzyme showing sequence similarity to adenylation domains of nonribosomal peptide synthetases (NRPSs); this enzyme, ZmaJ, contains an amino acid specificity code for the activation of L-serine (L-Ser). Not wanting to be bound by the following theory, it is possible that ZmaJ tethers L-Ser to ZmaH, and the seryl-ACP is then oxidized to AM-ACP (FIG. 5C). There is only one homolog of FkbK, the enzyme that catalyzes the first oxidation of glyceryl-ACP, suggesting that ZmaG catalyzes the first oxidation step in both pathways (FIG. 5B, C).

Figure 10:
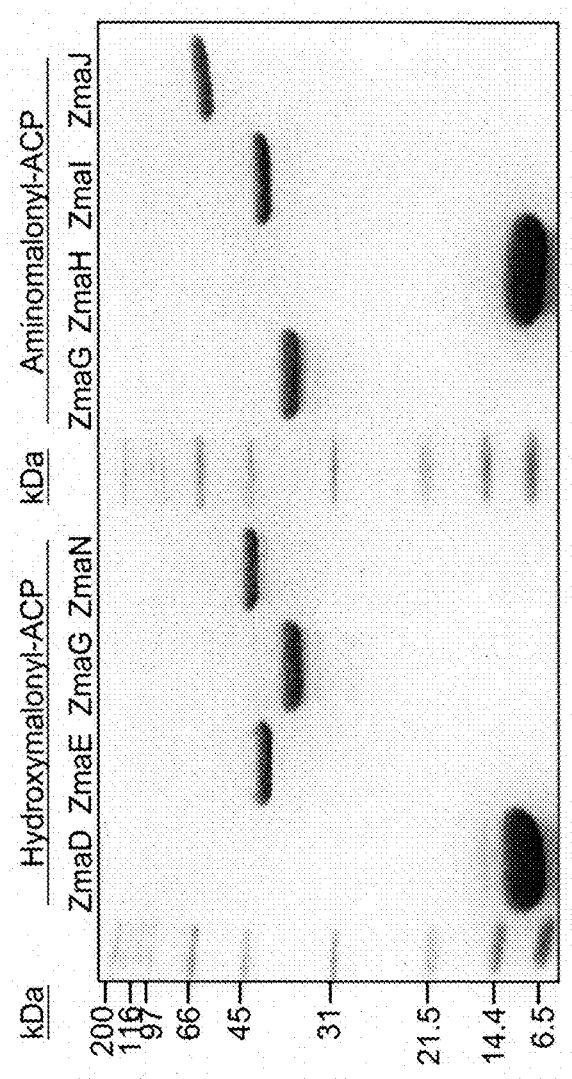
FIG. 10 is an image showing analysis of purified proteins by SDS-PAGE (12%) followed by Coomassie blue staining.

Biochemical and mass spectral approach were used to investigate whether HM-ACP and AM-ACP formation could be reconstituted in vitro. For this analysis, each protein was overproduced in *E. coli* as an N-terminally histidine-tagged protein and purified to near homogeneity using nickel-chelate chromatography (FIG. 10). Using these purified proteins, each pathway was tested for in vitro reconstitution. FIG. 10 is an image showing analysis of purified proteins by SDS-PAGE (12%) followed by Coomassie blue staining. The amount of protein loaded in each lane was as follows: 25 μg ZmaD and ZmaH; 4 μg ZmaE, ZmaG, and ZmaI; 2 μg ZmaN; 3 μg ZmaJ. The same molecular weight markers were loaded in the first and sixth lanes, with the kDa of each protein marker noted on the left. ZmaG is shown twice due to its proposed involvement in both HM-ACP and AM-ACP formation.

Formation of HM-ACP

Reaction mixtures (130 or 260 μl) contained the following components: 10 μM glyceryl-ZmaD, 58 mM Tris pH 7.5, 8 mM $MgCl_2$, 0.8 mM TCEP, 385 μM CoA, 0.8 μM Sfp, 250 μM D(-)$_3$—PG, 5 mM ATP, 1 μM ZmaN, 1 μM ZmaG, 200 μM $NAD^+$, 1 μM ZmaE, and 100 μM FAD. The reaction mixture was incubated at 22° C. for 1 hour prior to injection onto an HPLC. Reactions were repeated without ZmaG, ZmaE, or replacing ZmaE with 1 μM ZmaI.

The proposed pathway for HM-ACP formation involves tethering a substrate to the 4'-phosphopantetheinyl (4'-Ppant) prosthetic group of the ACP ZmaD, followed by modification of the tethered intermediate (FIG. 5B). Using HPLC and MALDI-TOF MS analysis, it was determined that the ZmaD purified from *E. coli* lacked the required prosthetic group (FIG. 6; Table 1).

Figure 6:
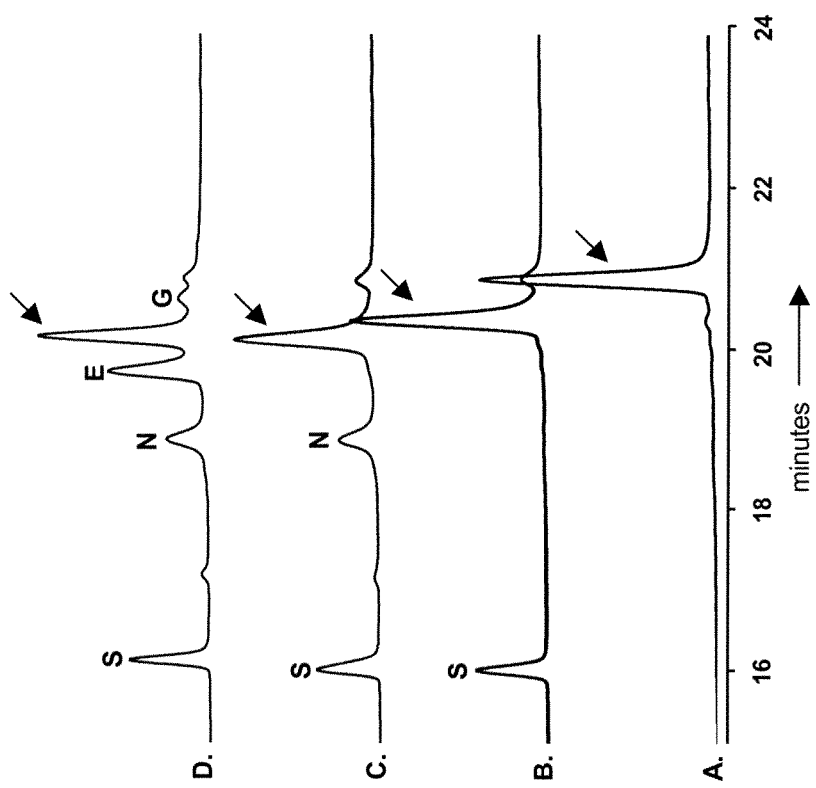
FIG. 6 is a graph showing HPLC analysis of ZmaD.

FIG. 6 illustrates HPLC analysis of ZmaD. Representative HPLC traces of reaction mixtures containing (A) apo-ZmaD; (B) apo-ZmaD, Sfp; (C) apo-ZmaD, Sfp, ZmaN; and (D) apo-ZmaD, Sfp, ZmaN, ZmaG, ZmaE, are shown. Protein elution was monitored at 220 nm. Arrows identify the peak associated with ZmaD derivatives, which were collected and analyzed by MS. The letters above absorbance peaks identify the elution of a protein from the reaction mixture: S, Sfp; N, ZmaN; E, ZmaE; G, ZmaG.

To generate holo-ZmaD, in vitro phosphopantetheinylation was performed using the 4'-Ppant transferase Sfp. HPLC and MALDI-TOF MS analysis determined that Sfp converted most of the apo-ZmaD to holo-ZmaD (FIG. 6; Table 1).

Not wanting to be bound by the following theory, FkbH is proposed to recognize a glycolytic intermediate, dephosphorylate it, and tether it to its partner ACP to form glyceryl-ACP (FIG. 5A). The most likely substrate for FkbH is 1,3-bisphosphoglycerate (1,3-bPG). It was thus determined whether ZmaN would catalyze the formation of glyceryl-ZmaD in the presence of 1,3-bPG. In this example, the formation of glyceryl-ZmaD can be detected by a change in the elution time of holo-ZmaD from the HPLC and a change in its mass as detected by MALDI-TOF MS. Although there is no commercial source of 1,3-bPG, enzymatic synthesis can be achieved using 3-phosphoglycerate (3-PG), ATP, and 3-PG phosphokinase (PK). Incubation of these components with ZmaN and holo-ZmaD did result in a shift in holo-ZmaD elution time; however, this shift did not require the addition of 3-PGPK (FIG. 6). This suggested either the substrate for ZmaN is 3-PG, or the reaction mixtures were contaminated with an unidentified source of 3-PGPK and the substrate was the resulting 1,3-bPG. Consistent with the latter hypothesis, the rate of holo-ZmaD modification was enhanced when the 3-PGPK was added to the reaction (1.44 nmol min-1 with 3-PGPK, 0.08 nmol min-1 without 3-PGPK). Furthermore, the equivalent change in elution time of holo-ZmaD was observed when glyceraldehyde-3-phosphate dehydrogenase (GAPDH) was used to convert glyceraldehyde-3-phosphate to 1,3-bPG. Based on these observations, 1,3-bPG is the substrate for ZmaN-catalyzed modification of holo-ZmaD.

To determine whether the modified holo-ZmaD was glyceryl-ZmaD, the purified ZmaD derivatives from the reactions containing the contaminating kinase and the GAPDH were analyzed by MALDI-TOF MS. The mass of holo-ZmaD had shifted to be consistent with the formation of glyceryl-ZmaD (Table 1). Importantly, holo-ZmaH was not a substrate for ZmaN-catalyzed formation of glyceryl-ACP, suggesting ZmaN specifically recognizes holo-ZmaD.

A mass consistent with 3-phosphoglyceryl-ZmaD was not detected, suggesting the phosphatase activity of ZmaN occurs prior to the acylation of holo-ZmaD. The 3-phosphoryl group may be extraneous since it plays no obvious role in the HM-ACP pathway. Its presence is likely because 1,3-bPG is the most readily available glyceryl primary metabolite containing an activated acid, thereby requiring the removal of the 3-phosphoryl group prior to downstream reactions. ZmaN may coordinate this phosphatase activity with its acyltransferase activity. ZmaN and its homologs contain the DXDX (T/V) motif of the phosphatase members of the haloacid dehalogenase superfamily of hydrolases. During catalysis, these enzymes remove the phosphate from the substrate by first forming a phosphoaspartyl intermediate, then hydrolyzing the phosphate from the enzyme. Structural analyses of members of this enzyme superfamily suggest the phosphoaspartyl formation is associated with a conformation change of the enzyme. The phosphoaspartyl intermediate in ZmaN catalysis may alter the conformation of ZmaN to enhance its interactions with holo-ZmaD once the 3-phosphoryl group is removed from the substrate, thereby coordinating the phosphatase and acyltransferase activities.

ZmaG and ZmaE are predicted to catalyze the oxidation of glyceryl-ZmaD to HM-ZmaD (FIG. 5B). These enzymes were incubated independently or together with their appropriate coenzymes along with glyceryl-ZmaD. A subtle change in elution time of glyceryl-ZmaD was observed (FIG. 6); this change required both ZmaG and ZmaE. Independently, neither enzyme was found to modify the glyceryl-ZmaD intermediate. Replacement of ZmaE with ZmaI also resulted in a change in elution time and mass, suggesting that either FkbI homolog may be involved in HM-ACP formation.

Analysis of the purified ZmaD-tethered product from the ZmaG/ZmaE reaction by MALDI-TOF MS detected a mass consistent with the decarboxylated form of HM-ZmaD, glycolyl-ZmaD (Table 1). This decarboxylation could be the result of the instability of the product under the assay conditions or due to the sample preparation and ionization process for MALDI-TOF MS. However, the detection of glycolyl-ZmaD is indicative of the formation of HM-ZmaD.

Figure 7:
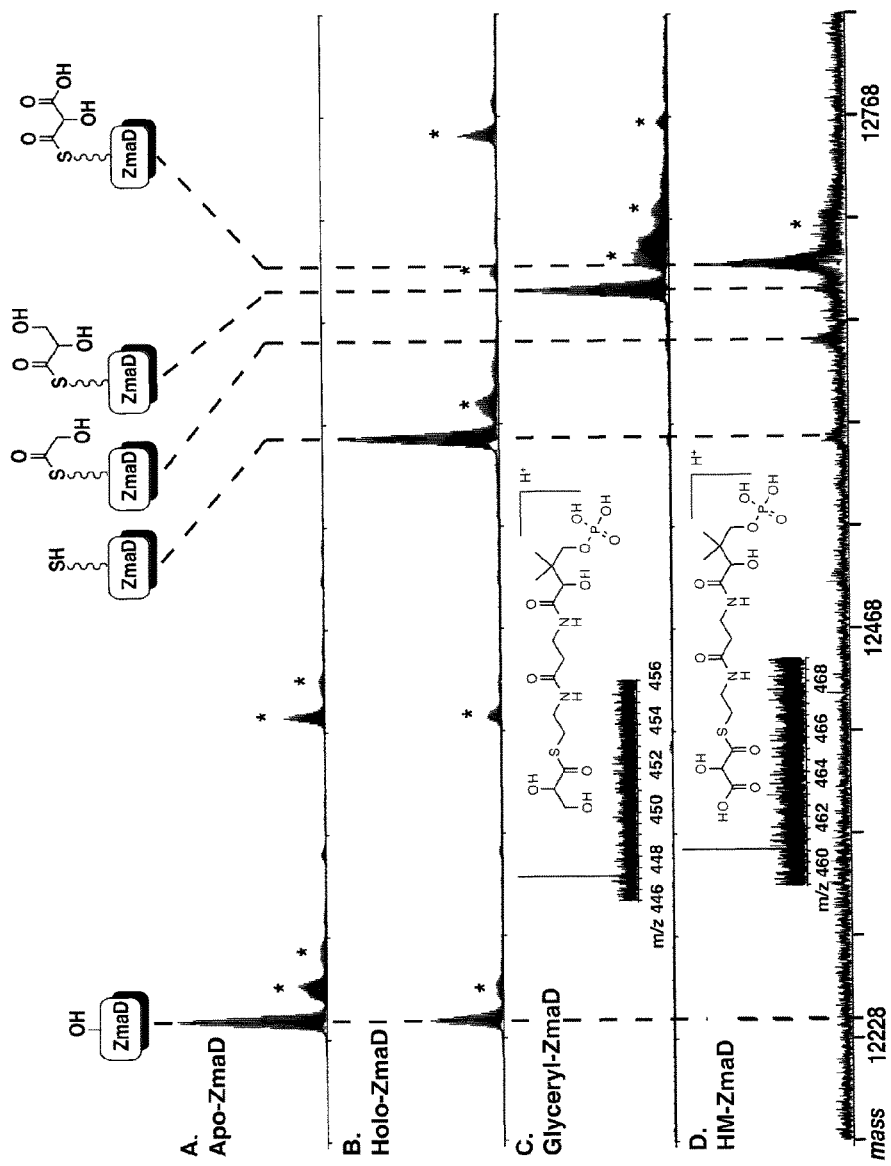
FIG. 7 shows ESI-FT-ICR-MS spectra of the intermediates in HM-ZmaD formation.

To more directly identify the ZmaD product of each reaction and to investigate whether an alternative MS technique could detect the HM-ZmaD final product, ESI-FT-ICR-MS was used to analyze the ZmaD products. The intact mass spectra collected showed mass shifts consistent with the formation of holo-ZmaD (+340 Da), glyceryl-ZmaD (+426 Da), HM-ZmaD (+442 Da), and glycolyl-ZmaD (+398 Da) (FIG. 7). MS/MS data localized the active site to the sequence G Y V N S, where the S is the site of 4'-Ppant, and mass shifts were confirmed through measurement of the 4'-Ppant elimination product (Insets FIG. 7). Importantly, ESI-FT-ICR-MS enabled detection and mass spectral analysis of HM-ZmaD.

These data are consistent with the in vitro reconstitution of HM-ACP formation and present direct evidence for the existence of ACP-linked Type I PKS extender units. The data suggest that the substrate for both HM-ACP and MM-ACP formation is 1,3-bPG.

Formation of AM-ACP

Not wanting to be bound by the following theory, the inventors proposed that the extender unit AM-ACP accounts for the ethanolamine unit in ZMA (FIG. 1). ZmaJ, a homolog of adenylation domains of NRPSs, is proposed to recognize L-Ser and tether it onto the ACP homolog ZmaH. The seryl moiety is subsequently oxidized in two steps to AM-ACP, analogous to the conversion of glyceryl-ACP to HM-ACP (FIG. 5).

Analysis of the amino acid substrate specificity of ZmaJ by standard ATP/PPi exchange assays using L-Ser and structurally related amino acids (L-2,3-diaminopropionate, L-Thr, Gly, and L-Cys) determined ZmaJ activated only L-Ser.

Determination of the kinetic parameters of ZmaJ for L-Ser activation yielded values expected for adenylation domains of NRPSs ($K_m$=1.8±0.2 mM; $k_{cat}$=42±2 min$^{-1}$). To test whether ZmaJ tethers L-Ser to ZmaH, holo-ZmaH was needed.

Figure 8:
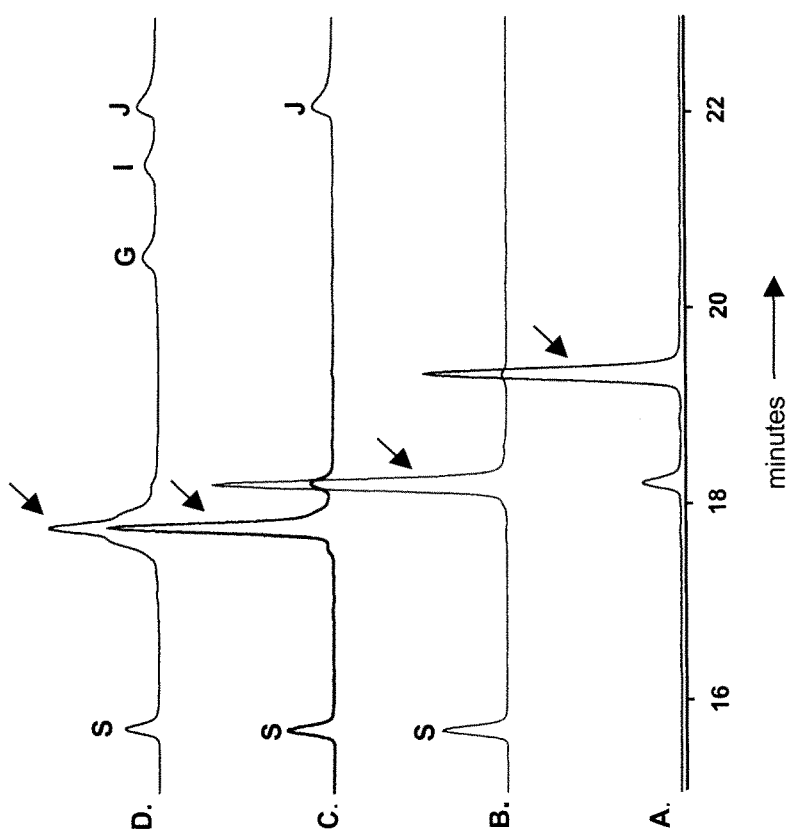
FIG. 8 is a graph showing HPLC analysis of ZmaH.

FIG. 8 illustrates HPLC analysis of ZmaH. Representative HPLC traces of reaction mixtures containing (A) apo-ZmaH; (B) apo-ZmaH, Sfp; (C) apo-ZmaH, Sfp, ZmaJ; (D) apo-ZmaH, Sfp, ZmaJ, ZmaG, ZmaI. Each reaction also contained the required cofactors and substrates.

Protein elution was monitored at 220 nm. Arrows identify the peak associated with ZmaH derivatives, which were collected and analyzed by MS. The letters above peaks identify the elution of a protein in the reaction mixture: S, Sfp; G, ZmaG; I, ZmaI; J, ZmaJ.

Following the same protocol for the conversion of apo-ZmaD to holo-ZmaD, it was determined that a majority of ZmaH is purified from E. coli in its apo form, and apo-ZmaH is efficiently converted to holo-ZmaH by Sfp (FIG. 8; Table 1). Incubation of holo-ZmaH with ZmaJ, L-Ser, and ATP resulted in a change in the holo-ZmaH elution time from the HPLC, and the mass of the purified product was consistent with the formation of seryl-ZmaH (Table 1). Importantly, ZmaJ was not able to aminoacylate holo-ZmaD, highlighting the specificity of ZmaJ for holo-ZmaH.

To test for AM-ZmaH formation, ZmaG and ZmaI were added independently or together with seryl-ZmaH. Only when ZmaG and ZmaI were added together, along with NAD$^+$ and FAD, was a change in the seryl-ZmaH elution profile observed, as indicated by a broadening of the seryl-ZmaH peak (FIG. 8). ZmaE, the homolog of ZmaI from the HM-ZmaD pathway, could not replace ZmaI. These data suggest ZmaI is specific for AM-ZmaH formation while ZmaE is involved in HM-ZmaD formation. Analysis of the ZmaG/ZmaI-modified seryl-ZmaH derivative by MALDI-TOF MS was consistent with the formation of glycyl-ZmaH, the product expected if AM-ZmaH becomes decarboxylated, along with unreacted seryl-ZmaH (Table 1). Longer incubation of the reaction resulted in nearly complete conversion of seryl-ZmaH to glycyl-ZmaH.

The observed decarboxylation product could be due to the instability of the AM-ZmaH or to the decarboxylation caused by the MALDI-TOF MS analysis as discussed above with HM-ZmaD. To identify more directly the ZmaH-tethered products of each reaction, ESI-FT-ICR-MS analysis was performed on ZmaH purified from each reaction mixture.

Figure 9:
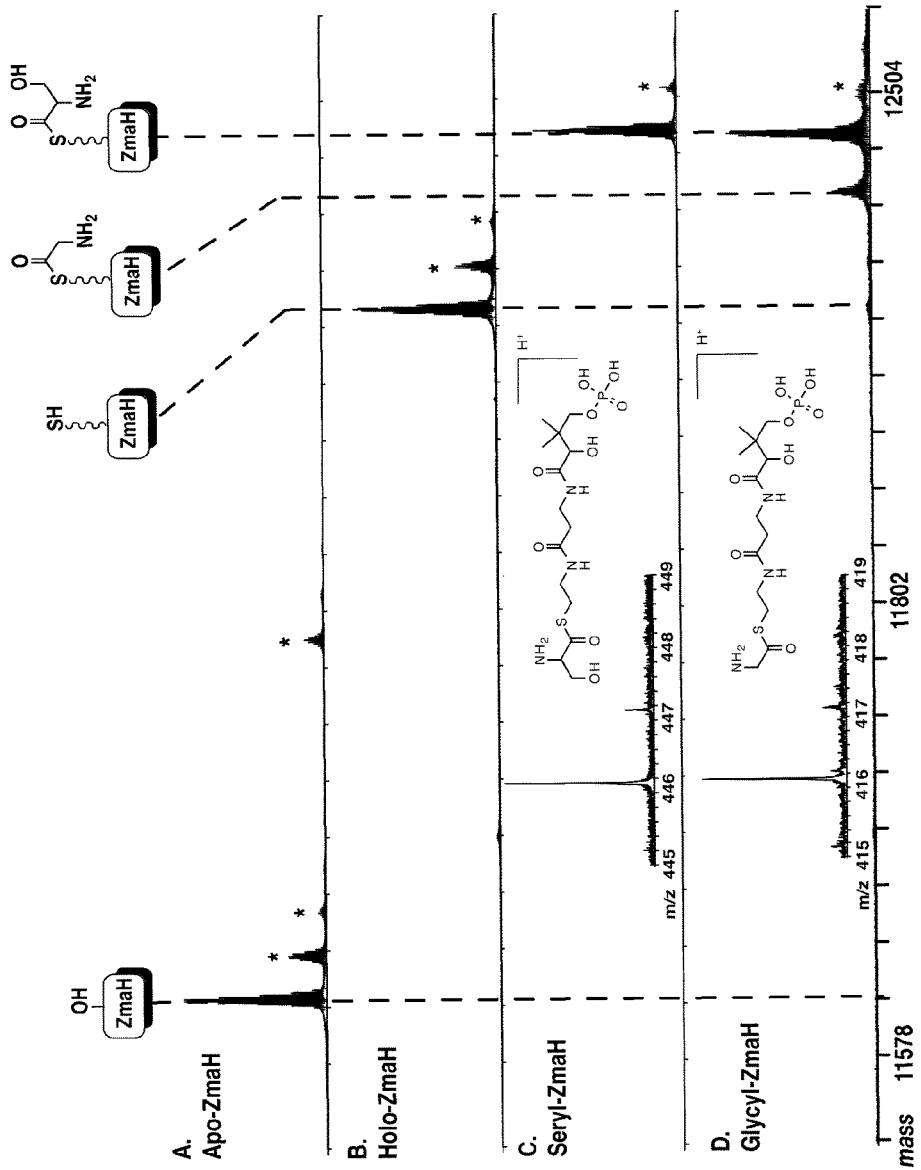
FIG. 9 shows ESI-FT-ICR-MS spectra of the intermediates in AM-ZmaH formation.

FIG. 9 is an ESI-FT-ICR-MS spectra of the intermediates in AM-ZmaH formation. Top of FIG. 9 depicts ZmaH intermediates of interest (from left to right: apo-, holo-[+340 Da], glycyl-[+397 Da], seryl-ZmaH [+427 Da] and alignment to the representative peaks in the mass spectra as indicated by vertical dashed lines. Shown in FIG. 9 are the loading and corresponding mass shifts (825-865 m/z, +14 ions converted to mass scale) of: (A) apo-ZmaH; (B) holo-ZmaH; (C) seryl-ZmaH; (D) glycyl-ZmaH; asterisks indicate signals arising from artifactual adduction: sodium (+22 Da), potassium (+38 Da), phosphate (+98 Da), and oxidation of Met/Cys residues (+16 Da). Insets show mass spectra and structures of 4'-Ppant elimination product.

The intact mass spectra collected showed mass shifts consistent with the formation of holo-ZmaH (+340 Da), seryl-ZmaH (+427 Da), and glycyl-ZmaH (+397 Da) (FIG. 9). MS/MS data localized the active site to the sequence GLVNS (SEQ ID NO:14), where the S is the site of 4'-Ppant, and mass shifts were confirmed through measurement of the 4'-Ppant elimination product (see inset in FIG. 9). To address the lack of observable AM-ZmaH and lack of conversion of all of the seryl-ZmaH, the seryl-ZmaH was incubated for 5 or 40 min with ZmaG and ZmaI. After 40 min, the seryl-ZmaH was almost completely converted to glycyl-ZmaH (FIG. 11).

Figure 11:
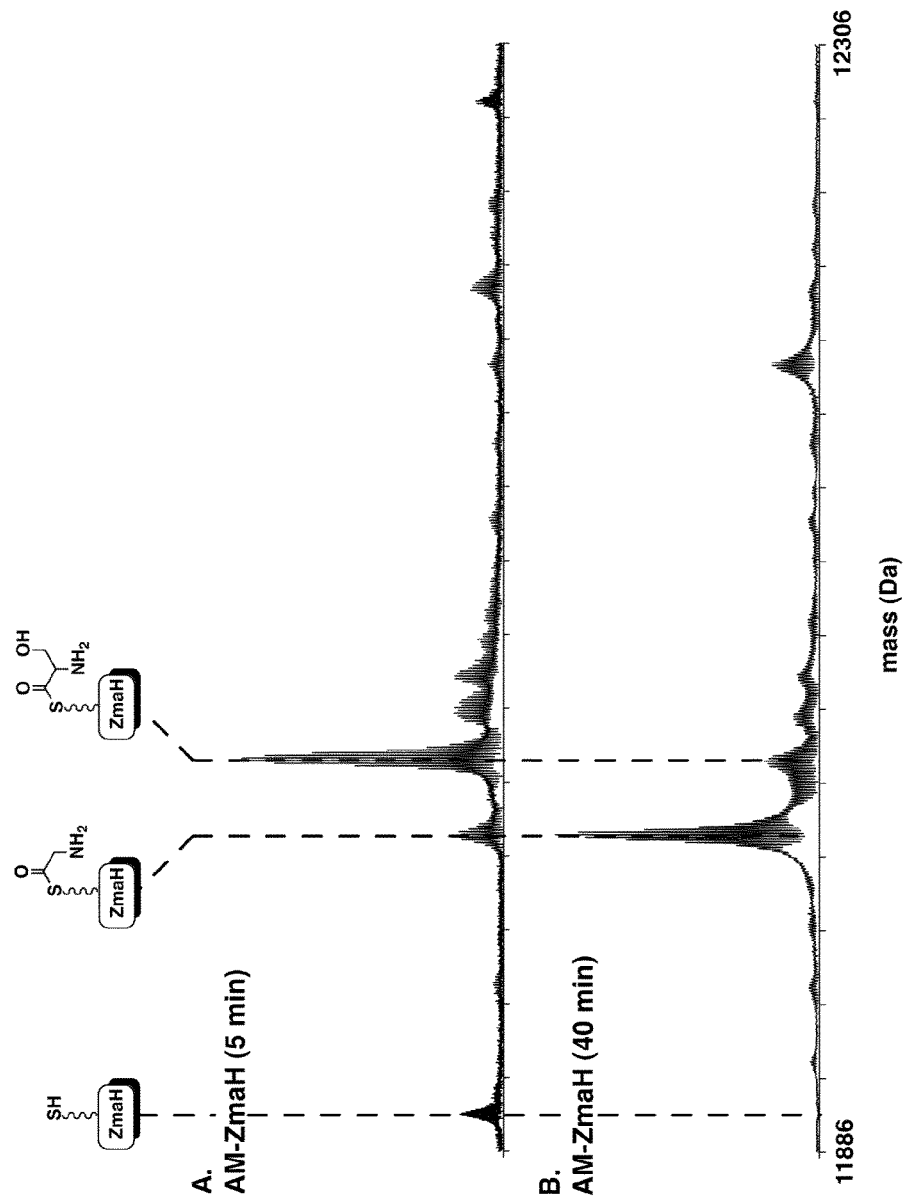
FIG. 11 shows ESI-FT-ICR-MS spectra of AM-ZmaH reactions.

FIG. 11 is ESI-FT-ICR-MS analysis of AM-ZmaH reactions. The top of FIG. 11 depicts ZmaH intermediates of interest (from left to right: holo-[+340], glycyl-[+397 Da], seryl-ZmaH [+427 Da]) and alignment to the representative peaks in the mass spectra as indicated by vertical dashed lines. Shown are the loading and corresponding mass shifts (825-865 m/z, +14 ions) of 5 min reaction (FIG. 11A), and of 40 min reaction (FIG. 11B). AM-ZmaH, however, was not detected.

Figure 12:
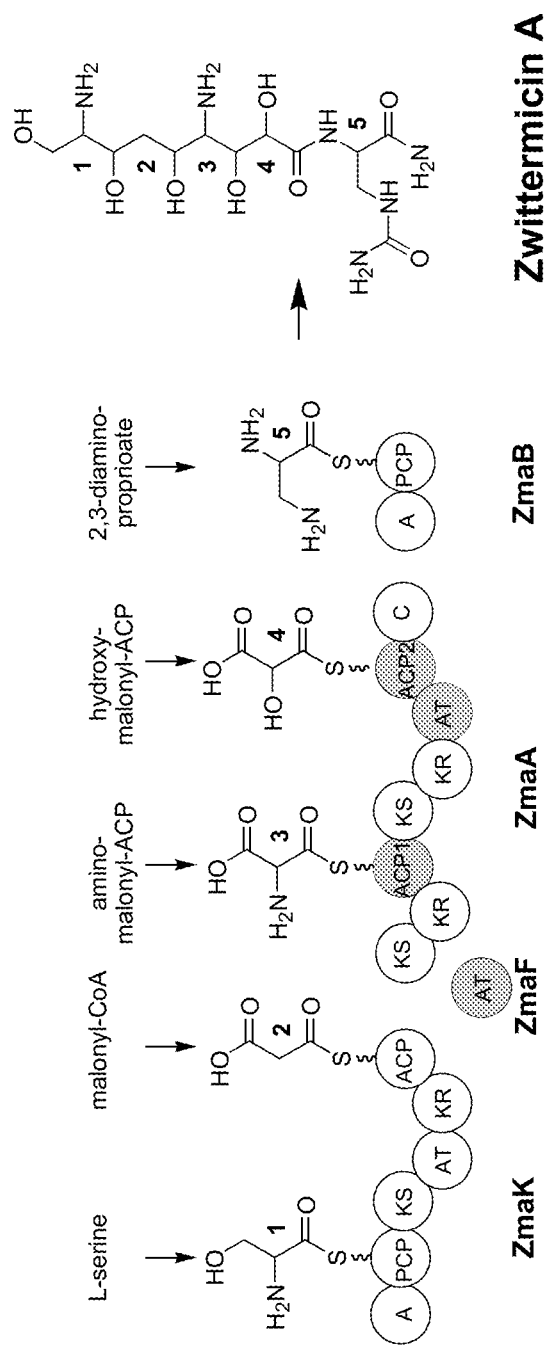
FIG. 12 is a schematic representation of the portion of the ZMA nonribosomal peptide synthetase (NRPS) and a Type I PKS that can be generated according to this invention.

The finding of glycyl-ZmaH using both MS approaches suggests assay conditions cause the decarboxylation of AM-ZmaH. This finding is not surprising based on the high level of spontaneous decarboxylation that occurs with aminomalonate. Under acidic conditions this decarboxylation is very rapid. The HPLC assays conditions included 0.1% TFA in the solvents to function as an ion-pairing agent to enhance the resolution of proteins eluting from the HPLC. The presence of TFA in the solvents reduces the pH of the solvents to 2.0 and would likely expedite the decarboxylation of AM-ACP to glyceryl-ACP. Analysis of reaction mixtures directly by MS without prior HPLC separation also detected a mass consistent with glycyl-ZmaH. The presence of glycyl-ZmaH is indicative of AM-ZmaH formation.

the polyketide. FIG. 12 is a schematic representation of the portion of the ZMA nonribosomal peptide synthetase (NRPS) and Type I PKS. Each circle represents a catalytic domain, with the NRPS or PKS extender unit tethered to the cognate peptidyl carrier protein (PCP) or ACP domain and identified above it. The grey circles represent the AT and ACP domains of interest. Numbering identifies the extender unit for better correlation to the final ZMA structure. Abbreviations for domains: A, adenylation; PCP, peptidyl carrier protein; KS, ketosynthase; KR, ketoreductase; C, condensation.

To test this possibility in vitro characterization of ZmaF and four different derivatives of ZmaA can be used. The four derivatives of ZmaA include the wild-type enzyme along with three derivatives containing mutations that disrupt the function of ACP1 (ZmaA-ACP1$^M$), ACP2 (ZmaA-ACP2$^M$), and the AT (ZmaA-AT$^M$). These ZmaA derivatives can be used in combination with ZmaF, [$^{14}$C]-HM-ACP, and [$^{14}$C]-AM-ACP extender units to identify which AT domain recognizes each extender unit, and to which ACP domain each extender unit is tethered. This can be determined by identifying the enzymes and domains required for the tethering of [$^{14}$C]-HM and [$^{14}$C]-AM onto ZmaA.

FIG. 12 is a schematic representation of the portion of the ZMA nonribosomal peptide synthetase (NRPS) and Type I PKS. Each circle represents a catalytic domain, with the

TABLE 1

MS analysis of purified apo- and holo-proteins

| Protein[a] | MALDI-MS | | ESI-FT-ICR-MS | | Phosphopantetheinyl Elimination | | |
|---|---|---|---|---|---|---|---|
| | Theo. [M + H]+ | Exp. [M + H]+ | Theo. Ave. Mass | Exp. Ave. Mass | | Theo. [M + H]+ | Exp. [M + H]+ |
| ZmaD | | | | | | | |
| apo-ZmaD | 12,239 | 12,239 | 12,238.7 | 12,238.3 | | | |
| holo-ZmaD | 12,579 | 12,579 | 12,579.0 | 12,579.3 | | | |
| glyceryl-ZmaD | 12,667 | 12,668[b] 12,670[c] | 12,667.1 | 12,667.4 | glyceryl | 447.120 | 447.121 |
| HM-ZmaD | 12,681 | ND[d] | 12,681.1 | 12,681.3 | HM | 461.099 | 461.099 |
| glycolyl-ZmaD | 12,637 | 12,636 | 12,637.1 | 12,637.4 | glycolyl | 417.109 | 417.110 |
| ZmaH | | | | | | | |
| apo-ZmaH | 11,609 | 11,605 | 11,609.1 | 11,608.8 | | | |
| holo-ZmaH | 11,949 | 11,946 | 11,949.4 | 11,949.1 | | | |
| seryl-ZmaH | 12,037 | 12,038[e] 12,036[f] | 12,036.5 | 12,036.8 | seryl | 446.136 | 446.136 |
| AM-ZmaH | 12,051 | ND | | | | | |
| glycyl-ZmaH | 12,007 | 12,007 | 12,006.5 | 12,006.8 | glycyl | 416.125 | 416.124 |

[a]The mass of ZmaD and ZmaH derivatives is calculated after removal of the first methionine.
[b]The mass of glyceryl-ZmaD detected when 3-phosphoglycerate was the starting substrate.
[c]The mass of glyceryl-ZmaD detected when 3-phosphoglyceraldehyde was the starting substrate.
[d]ND = not detected
[e]The mass of seryl-ZmaH detected in the ZmaJ, holo-ZmaH reaction.
[f]The mass of seryl-ZmaH detected in the ZmaJ, holo-ZmaH, ZmaG, and ZmaI reaction.

The data presented here are consistent with the formation of the AM-ACP extender unit. The enzyme that catalyzes the first oxidation of both glyceryl-ZmaD and seryl-ZmaH has no selectivity between the two intermediates; however, the second oxidation is catalyzed by a pathway-specific dehydrogenase. The formation of AM-ACP is the first known example of an amino acid being converted to a PKS extender unit.

Identification of AT Domains that Recognize and Incorporate the HM-ACP and AM-ACP Extender Units During ZMA Biosynthesis ZmaA and ZmaF contain the enzymatic domains for the incorporation of HM-ACP and AM-ACP extender units into NRPS or PKS extender unit tethered to the cognate peptidyl carrier protein (PCP) or ACP domain and identified above it. The grey circles represent the AT and ACP domains of interest for this proposal. Numbering identifies the extender unit for better correlation to the final ZMA structure. Abbreviations for domains: A, adenylation; PCP, peptidyl carrier protein; KS, ketosynthase; KR, ketoreductase; C, condensation.

ZmaF and the ZmaA derivatives containing affinity tags can be overproduced, for example in *Escherichia coli*. These enzymes can be purified using nickel-chelate chromatography. The mutant ZmaA proteins can be generated using standard site-directed mutagenesis techniques on zmaA. [$^{14}$C]-

Figure 4:
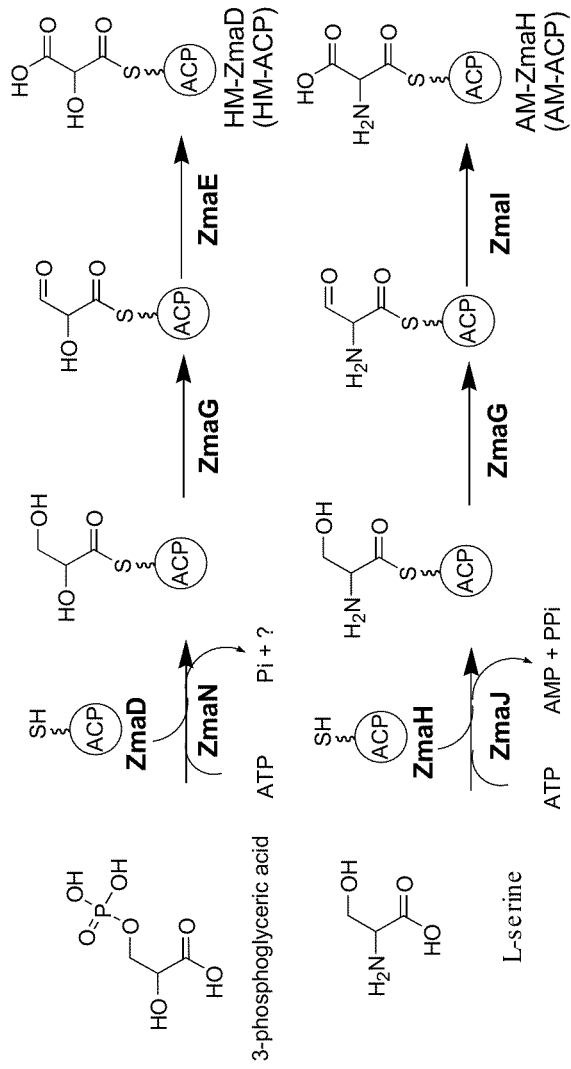
FIG. 4 is a schematic representation of the HM-ACP biosynthetic pathway (top) and the AM-ACP biosynthetic pathway (bottom) used by *Bacillus cereus* for zwittermicin A (ZMA) production.

HM-ACP and [$^{14}$C]-AM-ACP can be generated using the reconstituted extender unit biosynthetic pathways by starting the reactions with [$^{14}$C]-3-phosphoglycerate or [$^{14}$C]-L-serine, respectively (FIG. 4).

The different ZmaA derivatives can be incubated independently with [$^{14}$C]-HM-ACP or [$^{14}$C]-AM-ACP in the presence or absence of ZmaF. After termination of the reactions, the proteins in each reaction are separated by SDS-PAGE, the proteins visualized by Coomassie blue staining, and the ZmaA derivatives containing radiolabeled extender units are identified by phosphoimaging of the stained gel. Not wanting to be bound by the following theory, based on the inventors' model for ZMA biosynthesis, [$^{14}$C]-HM can be detected on the wild-type ZmaA and ZmaA-ACP1$^M$, but not on ZmaA-ACP2$^M$ or ZmaA-AT$^M$ regardless of whether ZmaF is present. However, [$^{14}$C]-AM can be detected on wild-type ZmaA, ZmaA-ACP2$^M$, and ZmaA-AT$^M$, and will require ZmaF. The hypotheses for the domains involved in HM-ACP and AM-ACP utilization are based on bioinformatics analysis of the ZMA biosynthetic pathway. Alternatives to this model are possible, and can be detected by the above experiments.

Thus, the AT domains and their partner ACP domains that are involved in the recognition and incorporation of HM-ACP and AM-ACP extender units can be identified. Furthermore, domains can be identified that can be used for investigating the metabolic engineering of other Type I PKSs to create novel, potentially clinically useful molecules.

Figure 13:
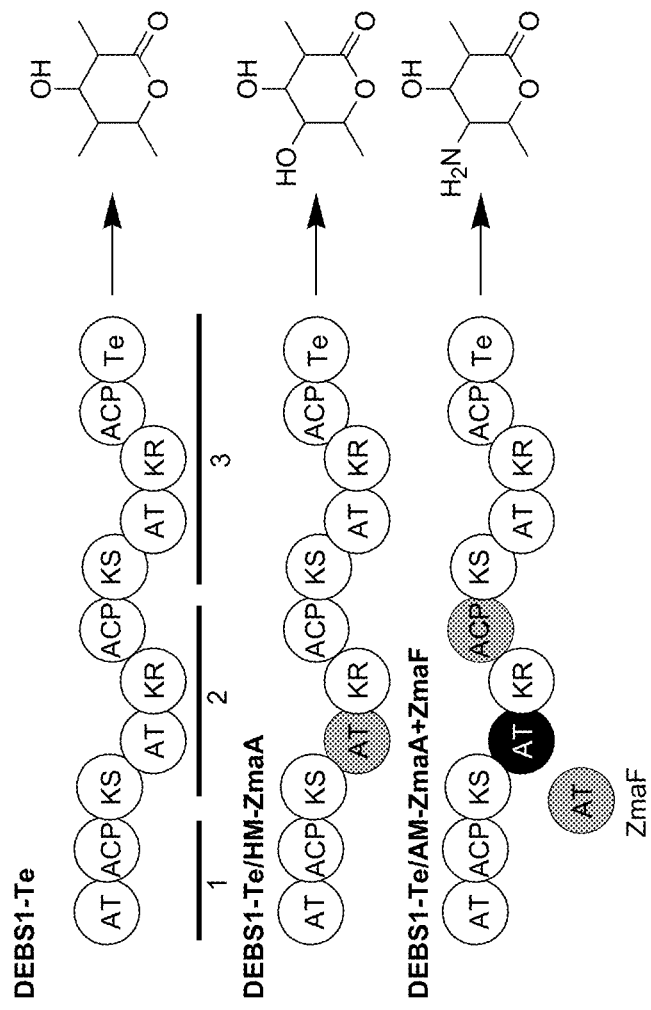
FIG. 13 is a schematic representation of wild-type DEBS1-Te and its derivatives that can be generated according to this invention.

Metabolic Engineering of a Portion of the Erythromycin Type I PKS to Incorporate HM-ACP or AM-ACP Extender Units A modified version of the erythromycin PKS can be used, which contains only its first three modules fused to a thioesterase domain. This construct, called DEBS1-Te, naturally condenses and cyclizes one propionyl-CoA starter unit with two methylmalonyl-CoA extender units into a triketide lactone (FIG. 13). This construct is commonly used for initial investigations into metabolic engineering of Type I PKSs.

FIG. 13 is a schematic representation of wild-type DEBS1-Te and its derivatives that can be constructed according to this invention. The structures on the right are the established or proposed triketide lactone structures produced by the Type I PKSs. Circles represent PKS domains. Grey circles represent ZMA PKS domains used to engineer DEBS1-Te. Black circle represents inactivated AT domain. Abbreviations are as defined in text and FIG. 7 with the addition of Te, thioesterase. Bars and numbers under DEBS1-Te denote the three modules of the Type I PKS.

Derivatives of DEBS1-Te can be engineered with the ability to incorporate either HM-ACP or AM-ACP as the first extender unit. Importantly, the sites for inserting noncognate domains into the erythromycin PKS have been previously defined (McDaniel et al., 1999, Proc. Natl. Acad. Sci. USA 96: 1846-1851; Hans et al., 2003, J. Am. Chem. Soc. 125: 5366-5374); thus, the construction of these engineered derivatives is straightforward. One PKS derivative can have the natural methylmalonyl-CoA-specific AT domain switched with the HM-ACP-specific AT domain from ZmaA, resulting in a hybrid Type I PKS that can generate 2-methyl-3,4,5-trihydroxy heptanoic acid γ-lactone (FIG. 13). A second PKS derivative can have the natural ACP domain of module 2 replaced by the ACP1 domain of ZmaA, and the natural AT domain of module 2 inactivated by site-directed mutagenesis. This modified DEBS1-Te can incorporate AM-ACP when ZmaF is added in trans, thereby generating 2-methyl-3,5-dihydroxy-4-amino heptanoic acid γ-lactone (FIG. 13).

The modified DEBS1-Te PKSs can be overproduced in Streptomyces coelicolor and the proteins can be purified using established protocols (Kao et al., 1994, Science 265: 509-512). The purified proteins can be incubated with propionyl-CoA, methylmalonyl-CoA, and [$^{14}$C]-HM-ACP or [$^{14}$C]-AM-ACP along with the required cofactors. ZmaF can also be added to those reactions containing [$^{14}$C]-AM-ACP. The products of the reactions can be separated by thin-layer chromatography as previously described for triketide lactone separation, and detected by phosphorimaging. If a new product is detected, the reaction can be scaled up with nonradioactive substrates, and the triketide lactones can be purified by HPLC and analyzed by mass spectrometry. Examples of predicted products are shown in FIG. 13. The overproduction of these proteins is straightforward based on previous success with this method (Pieper et al., 1995, Nature 378: 263-266). However, one skilled in the art is aware that a gene from B. cereus will have a different codon usage compared to S. coelicolor, which may change the production levels of the engineered enzymes. If desired, the codon usage of the inserted portions of zmaA can be changed to more closely match that for actinomycetes following established protocols (Menzella et al., 2005, Nature Biotech. 23: 1171-1176).

Thus, in some embodiments, the conditions for the engineering of a model Type I PKS to incorporate either HM-ACP or AM-ACP are provided. This is the first known example of engineering a PKS to incorporate a noncognate extender unit other than malonyl-CoA or methylmalonyl-CoA. Additionally, the triketide lactones are first known examples of hydroxyl or amino moiety functionality being introduced into a noncognate polyketide backbone.

Incorporation of Hydroxymalonyl-Acyl Carrier Protein (HM-ACP)

Cloning of the zwittermicin A (ZMA) biosynthetic genes. The genes zmaD, zmaE, zmaG, and zmaN were PCR amplified from B. cereus UW85 chromosomal DNA or the supernatant of boiled overnight cultures of *E. coli* DH10b/pBelo11-ZmA, a BAC vector containing the ZMA gene cluster. PCR products for zmaD, zmaE, zmaG, and zmaN were cloned into pET28b (Novagen) (kanamycin-resistant) using NdeI and either HindIII, SacI, or XhoI restriction sites. The gene zmaA was amplified as two overlapping fragments, consisting of a 4.5 kb fragment containing a naturally-occurring SmaI restriction site at the 3' end and a 5.5 kb fragment containing the SmaI restriction site at the 5' end. Both of these fragments were individually cloned into pCRBluntII-TOPO (Invitrogen) (kanamycin-resistant). The first fragment was subcloned to pET15b (ampicillin-resistant) using NdeI and NotI, and the second fragment was then subcloned into this construct using SmaI and XhoI to generate pET15b-zmaA. The DNA encoding the acyl transferase domain (AT) and second acyl carrier protein (ACP) domain of zmaA (ACP2) was PCR amplified from pET15b-zmaA. The AT domain was cloned into pET30a (kanamycin-resistant) using NcoI and XhoI, and ACP2 was cloned into pET28b using NdeI and XhoI. All clones were verified by sequencing at the University of Wisconsin Biotechnology Sequencing Center.

Heterologous overproduction of enzymes. All expression constructs were transformed into competent *Escherichia coli* BL21 (λDE3) cells for heterologous overexpression. For overproduction of ZmaD, ZmaG, ZmaN, AT, and ACP2, cells were grown at 25° C. with vigorous shaking in LB medium supplemented with 50 μg/mL kanamycin; when the $OD_{600}$ reached 0.4-0.6, the temperature was dropped to 15° C. After growing at 15° C. for 1.5-2.5 h, isopropyl-D-thiogalactopyranoside (IPTG) was added to a final concentration of 60-300 μM, and the cells were grown for an additional 16 h at 15° C.

For overproduction of ZmaE, cells were grown at 25° C. with vigorous shaking for 24 h in LB medium supplemented with 50 μg/mL kanamycin. Cells were harvested by centrifugation.

Purification of proteins. E. coli cells containing the expression constructs for zmaD, zmaE, zmaG, zmaN, AT, and ACP2 were resuspended in histidine-tag purification buffer (for ZmaG: 20 mM Tris-Cl [pH 8.0], 300 mM NaCl, 10% [w/v] sucrose; for all other proteins: 20 mM Tris-Cl [pH 8.0], 300 mM NaCl, 10% [v/v] glycerol). The resuspended cells were broken by sonication, and cell debris was removed by centrifugation. Imidazole was added to the cell-free extract at a final concentration of 5 mM, and the extract was incubated with 1-2 mL of Ni-NTA agarose resin (Qiagen) for 1-2 hours at 4° C. with gentle shaking. The resin was collected by centrifugation and packed into a column. The resin was washed with histidine-tag buffer containing imidazole (5 mM), and stepwise elutions were performed with histidine-tag buffer containing imidazole at final concentrations of 20, 40, 60, 100, and 250 mM. SDS-PAGE analysis of the collected fractions was performed. Fractions containing purified protein (as determined by Coomassie Blue-staining of the gel) were pooled and dialyzed at 4° C. in 1 L dialysis buffer (for ZmaD, ZmaE, ZmaN, ACP2: 50 mM Tris-Cl [pH 8 at 4° C.], 100 mM NaCl, and 10% [v/v] glycerol; for ZmaG: 50 mM Tris-Cl [pH 8 at 4° C.], 100 mM NaCl, and 10% [w/v] sucrose; for AT: 50 mM Tris-Cl [pH 8 at 4° C.], 50 mM NaCl, and 10% [v/v] glycerol). ZmaE was dialyzed further in high salt buffer (50 mM Tris-Cl [pH 8 at 4° C.], 300 mM NaCl, and 10% [v/v] glycerol) at 4° C.

Purified ZmaD, ZmaE, ZmaG, ZmaN, and ACP2 were concentrated using Millipore Centriprep protein concentrators, flash frozen with liquid nitrogen, and stored at −80° C.

The AT domain was concentrated using a Millipore Centriprep protein concentrator and then loaded onto BioRad BioScale Mini UNOSphere Q (5 mL) column for further purification. The column was washed with Buffer A (50 mM Tris-Cl [pH 8 at 4° C.], 50 mM NaCl, and 10% [v/v] glycerol), and the protein was eluted using a gradient of 0-100% B (50 mM Tris-Cl [pH 8 at 4° C.], 1 M NaCl, and 10% [v/v] glycerol) (flow rate 3 mL/min). Fractions containing the AT domain were pooled and dialyzed in 1 L dialysis buffer (50 mM Tris-Cl [pH 8 at 4° C.], 100 mM NaCl, and 10% [v/v] glycerol) at 4° C. The protein was then concentrated as before, flash frozen with liquid nitrogen, and stored at −80° C. Protein concentrations were determined using the calculated molar extinction coefficients (ZmaD, 2560 $M^{-1}$ $cm^{-1}$; ZmaE, 44410 $M^{-1}$ $cm^{-1}$; ZmaG, 21180 $M^{-1}$ $cm^{-1}$; ZmaN, 41070 $M^{-1}$ $cm^{-1}$; ACP2, 27880 $M^{-1}$ $cm^{-1}$; AT, 50810 $M^{-1}$ $cm^{-1}$).

Formation of HM-ACP2. Reaction mixtures contained the following components: 75 mM Tris-Cl (pH 7.5), 10 mM $MgCl_2$, 1 mM TCEP, 500 μM CoA, 12.5 μM ACP2, 1 μM ZmaD, 1 μM Sfp, 1 μM ZmaN, 200 μM $NAD^+$, 100 μM FAD, 1 μM ZmaG, 1 μM ZmaE, 1 μM AT, 1 U 3-phosphoglycerate phosphokinase (3-PGPK, Sigma), 250 μM 3-phosphoglycerate (3-PG, Sigma), and 5 mM ATP. Prior to the addition of ZmaN, $NAD^+$, FAD, ZmaG, ZmaE, AT, 3-PGPK, 3-PG, and ATP, the ACPs ZmaD and ACP2 were allowed to react with Sfp for an hour at room temperature to become phosphopantetheinylated. The complete reaction was initiated with the addition of ATP, and the reaction was incubated at room temperature for 45 minutes. Control reactions lacking ACP2, ZmaD, ZmaN, ZmaG, ZmaE, AT, and ATP were performed, as were control reactions in which ZmaF replaced AT.

HPLC analysis of reaction products. HPLC analysis of reaction products was performed with a Vydac (Hesperia, Calif.) C18 peptide column (250×4.6 mm). Two-hundred microliters of the reactions were injected, and the reaction products were separated using a 20-80% acetonitrile/0.1% TFA gradient over 20 min at a flow rate of 1 mL/min. Elution was monitored at 220 nm.

MALDI-TOF MS analysis of reaction products. The reaction products were collected as they eluted from the HPLC, flash-frozen with $CO_2$(s)/ethanol, and lyophilized overnight. Lyophilized samples were resuspended in double-distilled water and added to the sinipinic acid matrix (10 mg/L in 50% acetonitrile/0.05% TFA). MALDI-TOF MS analysis was performed using a Voyager Biospectrometry Workstation (DE-Pro; Applied Biosystems, Foster City, Calif.) in linear, positive mode. Cytochrome c, apomyoglobin, and aldolase (Sigma) were used as standards for calibration.

Incorporation of Aminomalonyl-ACP (AM-ACP)

Cloning of the ZMA biosynthetic genes. The genes zmaA and zmaG were cloned as described for HM-ACP incorporation. The genes zmaF, zmaH, zmaI, and zmaJ were PCR amplified from B. cereus UW85 chromosomal DNA or the supernatant of boiled overnight cultures of E. coli DH10b/pBelo11-ZmA, a BAC vector containing the ZMA gene cluster.

The PCR product for zmaF was cloned into pCRBluntII-TOPO and cloned into pET28b using NdeI and HindIII. The PCR products for zmaH, zmaI, and zmaJ were cloned into PGEM®-T Easy (Promega) (ampicillin-resistant) and subcloned into pET28b using NdeI and XhoI restriction sites. The DNA encoding the first ACP domain of zmaA was PCR amplified from pET15b-zmaA, cloned into pCRBluntII-TOPO, and subcloned into pET28b using NdeI and HindIII. All clones were verified by sequencing at the University of Wisconsin Biotechnology Sequencing Center.

Heterologous overproduction of enzymes. ZmaG was heterologously overproduced as described for HM-incorporation. All expression constructs were transformed into competent Escherichia coli BL21 (λDE3) cells for heterologous overexpression. For overproduction of ZmaA, cells were grown at 30° C. with vigorous shaking in LB medium containing 100 μg/mL ampicillin. When the $OD_{600}$ reached 0.8, the temperature was dropped to 15° C. After growing at 15° C. for 1.5 h, IPTG was added at a final concentration of 200 μM. Cells were grown for an additional 7.5 h and harvested. For overproduction of ZmaF, ZmaH, ZmaJ, and ACP1, cells were grown at 25° C. with vigorous shaking in LB medium supplemented with 50 μg/mL kanamycin; when the $OD_{600}$ reached 0.4-0.6, the temperature was dropped to 15° C. After growing at 15° C. for 1.5-2.5 h, IPTG was added to a final concentration of 60-300 μM, and the cells were grown for an additional 16 h at 15° C. For overproduction of ZmaI, cells were grown at 25° C. with vigorous shaking for 24 h in LB medium supplemented with 50 μg/mL kanamycin. Cells were harvested by centrifugation.

Purification of proteins. ZmaG was purified as described above for HM-ACP incorporation. E. coli cells containing the expression constructs for zmaA, zmaF, zmaH, zmaI, zmaJ, and ACP1 were resuspended in histidine-tag purification buffer (20 mM Tris-Cl [pH 8.0], 300 mM NaCl, 10% [v/v] glycerol). The resuspended cells were broken by sonication, and cell debris was removed by centrifugation. Imidazole was added to the cell-free extract at a final concentration of 5 mM, and the extract was incubated with 1-2 mL of Ni-NTA agarose resin (Qiagen) for 1-2 hours at 4° C. with gentle shaking. The resin was collected by centrifugation and packed into a column. The resin was washed with histidine-tag buffer containing imidazole (5 mM), and stepwise elutions were performed with histidine-tag buffer containing imidazole at final concentrations of 20, 40, 60, 100, and 250 mM. SDS-PAGE analysis of the collected fractions was performed. Fractions containing purified protein (as determined by Coomassie Blue-staining of the gel) were pooled and dialyzed at 4° C. in 1 L dialysis buffer (for ZmaH and ZmaJ: 50 mM Tris-Cl [pH 8 at 4° C.], 100 mM NaCl, and 10% [v/v] glycerol; for ACP1 and ZmaF: 50 mM Tris-Cl [pH 8 at 4° C.], 50 mM NaCl, and 10% [v/v] glycerol); for ZmaI: 50 mM Tris-Cl [pH 8 at 4° C.], 300 mM NaCl, and 10% [v/v] glycerol; for ZmaA: 50 mM Tris-Cl [pH 8 at 4° C.], 100 mM NaCl, and 10% [v/v] glycerol, 1 mM EDTA, and 20 µM PMSF). ACP1 was dialyzed further in a buffer containing higher salt concentration (50 mM Tris-Cl [pH 8 at 4° C.], 100 mM NaCl, and 10% [v/v] glycerol). ZmaI was dialyzed further in high salt buffer containing FAD (50 mM Tris-Cl [pH 8 at 4° C.], 300 mM NaCl, 10% [v/v] glycerol, and 100 µM FAD) and then in high salt buffer lacking FAD. Purified ZmaH, ZmaI, ZmaJ, and ACP1 were concentrated using Millipore Centriprep protein concentrators, flash frozen with liquid nitrogen, and stored at −80° C. Purified ZmaA was flash frozen with liquid nitrogen and stored at −80° C. ZmaF was loaded onto 2 BioRad Bio-Scale™ Mini DEAE Affi-Gel Blue cartridges (5 mL) for further purification. The column was washed with Buffer A (50 mM Tris-Cl [pH 8 at 4° C.], 50 mM NaCl, and 10% [v/v] glycerol), and the protein was eluted using a gradient of 0-100% B (50 mM Tris-Cl [pH 8 at 4° C.], 1 M NaCl, and 10% [v/v] glycerol) (flow rate 3.5 mL/min). Fractions containing ZmaF were pooled and dialyzed in 1 L dialysis buffer (50 mM Tris-Cl [pH 8 at 4° C.], 50 mM NaCl, and 10% [v/v] glycerol) at 4° C., further dialyzed in a buffer containing higher salt concentration (50 mM Tris-Cl [pH 8 at 4° C.], 100 mM NaCl, and 10% [v/v] glycerol), concentrated using a Millipore Centriprep protein concentrator, and flash frozen with liquid nitrogen and stored at −80° C. Protein concentrations were determined using the calculated molar extinction coefficients (ZmaH, 2560 $M^{-1}$ $cm^{-1}$; ZmaI, 44770 $M^{-1}$ $cm^{-1}$; ZmaJ, 46760 $M^{-1}$ $cm^{-1}$; ZmaF, 37820 $M^{-1}$ $cm^{-1}$).

Formation of AM-ZmaA. ZmaA and ZmaH were first converted to holo-form in separate reactions with Sfp. ZmaA was incubated at room temperature for 1.5 h in a 50 µL reaction mixture containing 75 mM Tris-Cl (pH 7.5), 10 mM $MgCl_2$, 500 µM CoA, 37.75 µL ZmaA (partially purified), and 1 µM Sfp. ZmaH was incubated at room temperature for 1 h in a 50 µL reaction mixture containing 75 mM Tris-Cl (pH 7.5), 10 mM $MgCl_2$, 50 µM CoA, 40 µM ZmaH, and 1 µM Sfp. AM-ZmaH was formed in a 65 µL reaction mixture containing 36 µL of holo-ZmaH, 100 µM [$^{14}$C(U)]-L-serine, 5 mM ATP, 200 µM $NAD^+$, 100 µM FAD, 1 µM ZmaG, and 1 µM ZmaI. AM-ZmaA was formed in a 120 µL reaction mixture containing 65 µL of AM-ZmaH, 50 µL holo-ZmaA, and 5 µL of ZmaF. A control reaction was set up lacking ZmaF. After incubating at room temperature for 2.5 h, 30 µL of each reaction was removed to a tube containing an equal volume of 2× cracking buffer (lacking β-mercaptoethanol), and 25 µL of this mixture was loaded onto a Tris-Cl 4-15% gradient SDS-polyacrylamide gel (BioRad). The gel was stained with Coomassie, destained, dried, exposed to a phosphorimaging screen, and visualized after 9 days of exposure.

Formation of AM-ACP1. Fifty µL reaction mixtures contained the following components: 75 mM Tris-Cl (pH 7.5), 10 mM $MgCl_2$, 1 mM TCEP, 500 µM CoA, 15.96 µL ACP2 (partially purified), 1 µM ZmaH, 1 µM Sfp, 1 µM ZmaJ, 200 µM $NAD^+$, 100 µM FAD, 1.5 µM ZmaG, 1.5 µM ZmaI, 2 µM ZmaF, 100 µL [$^{14}$C(U)]-L-serine, and 5 mM ATP. Prior to the addition of ZmaJ, $NAD^+$, FAD, ZmaG, ZmaI, ZmaF, [$^{14}$C(U)]-L-serine, and ATP, the ACPs ZmaH and ACP1 were allowed to react with Sfp for an hour at room temperature to become phosphopantetheinylated. The complete reaction was initiated with the addition of ATP, and the reaction was incubated at room temperature for 1.5 h. Control reactions lacking ACP2, ZmaF, ZmaI, ZmaG, and ZmaJ were performed. Parallel reaction mixtures were set up containing the same components except with 18.5 µM instead of 1 µM ZmaH. Thirty µL of the reaction mixtures were removed to tubes containing an equal volume of 2× cracking buffer, and 25 µL of the mixtures were loaded onto Tris-Cl 12% SDS-polyacrylamide gel. The gels were stained with Coomassie, destained, dried, exposed to a phosphorimaging screen, and visualized after 9 days of exposure.

Metabolic Engineering of *Saccharopolyspora erythraea* to Produce 13-Amino- or 13-Hydroxy-Erythromycin Derivatives

*Saccharopolyspora erythraea* naturally produces erythromycin and has been metabolically engineered by to generate structural derivatives of this antibiotic. Metabolic engineering of this strain can be used for in vivo production of erythromycin derivatives that incorporate HM-ACP and AM-ACP extender units into the polyketide backbone of this important antibiotic. Briefly, the chromosomal eryAI gene, encoding the DEBS1 Type I PKS, can be modified so that it results in the production of DEBS1 derivatives that are analogous to the DEBS1-Te constructs discussed above, but will lack the Te domain. Therefore, either HM-ACP or AM-ACP extender units can be used as the second extender unit incorporated into the erythromycin polyketide backbone. The construction of these strains is straightforward since genetic techniques commonly used for other actinomycetes are transferable to *Saccharopolyspora erythraea*.

While the modification of eryA1 can result in a hybrid Type I PKS, *Saccharopolyspora erythaea* does not naturally produce HM-ACP or AM-ACP; thus, this bacterium has to be engineered to produce these extender units. This can be accomplished, for example, by generating artificial operons expressing zmaD, E, G, and N for HM-ACP formation, or zmaG, H, I, and J for AM-ACP formation (FIG. 4). The operon for AM-ACP formation can also contain the zmaF gene, coding for the AM-ACP recognizing AT domain. The construction of these operons can follow an established protocol whereby the target genes are cloned in sequence downstream of a desired promoter, with a ribosome-binding site separating each gene (Watanabe et al., 2006, *Nat. Chem. Biol.* 2: 423-428). The artificial operons can then be subcloned into a vector, pSET152, which has been shown to stably integrate into the *Saccharopolyspora erythraea* genome (Brunker et al, 1998, *Microbiology* 144: 2441-2448). The resulting strains can contain an engineered eryA1 within the natural erythromycin biosynthetic gene cluster, while production of the new extender unit can be controlled by genes constitutively expressed by the integrated pSET152 vector.

Figure 14:
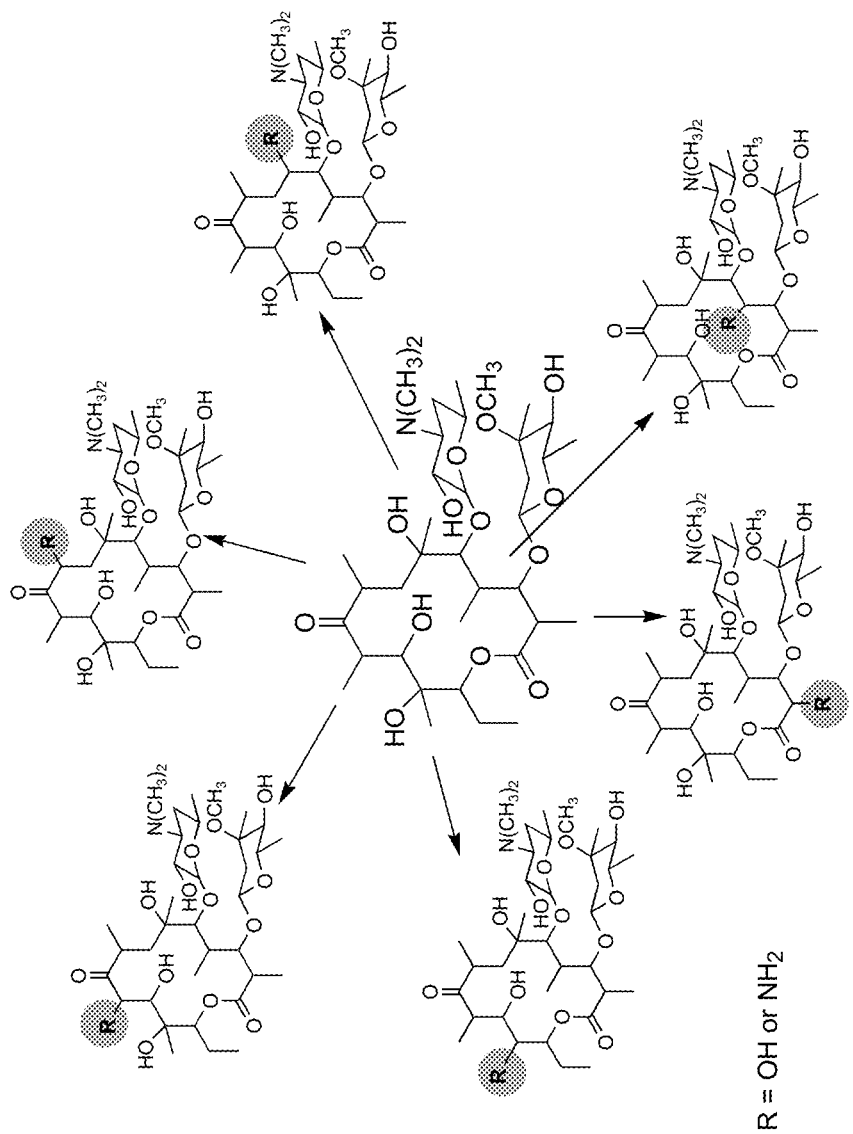
FIG. 14 is a schematic representation of the chemical structures of erythromycin (center) and putative six erythromycin derivatives that can be generated according to this invention.

The engineered *Saccharopolyspora erythraea* strains can be grown under standard conditions for optimal erythromycin production and the erythromycin derivatives can be purified from the culture supernatant using established protocols (Wilkinson et al., 2000, *Chem. Biol.* 7: 111-117). The products can be analyzed by mass spectrometry and [$^1$H]- and [$^{13}$C]-NMR. In one example, using the methods of this invention, 13-amino and 13-hydroxy derivatives of erythromycin can be generated by these strains. FIG. 14 illustrates the chemical structures of erythromycin (center) and putative erythromycin derivatives generated by using metabolic engineering. Grey circle highlights the C13 position of the inserted hydroxyl or amino group.

Using the methods of this invention, it would be possible to systematically change each position of the erythromycin polyketide backbone with amino or hydroxyl moieties (FIG.

14). Each of these derivatives can then be screened for activity against *M. tuberculosis*, and can also be used a starting compound for downstream chemical modifications. For example, each free amino group can be modified by simply incubating the molecule with N-hydroxysuccinimide esters, which react spontaneously with primary amines. There are hundreds of N-hydroxysuccinimide esters available through various chemical supply companies, raising the possibility of generating hundreds of new erythromycin derivatives. This example of the invention, with emphasis on antituberculosis drugs, can be particularly relevant, as the introduction of modifications to the C12 position of erythromycin results in an antibiotic with enhanced activity against *M. tuberculosis* (Kanakeshwari et al., 2004, *Antimicrob. Agents Chemother.* 49: 1447-1454).

It is to be understood that this invention is not limited to the particular devices, methodology, protocols, subjects, or reagents described, and as such may vary. It is also to be understood that the terminology used herein is for the purpose of describing particular embodiments only, and is not intended to limit the scope of the present invention, which is limited only by the claims. Other suitable modifications and adaptations of a variety of conditions and parameters normally encountered in molecular biology and biochemistry, and obvious to those skilled in the art, are within the scope of this invention. All publications, patents, and patent applications cited herein are incorporated by reference in their entirety for all purposes.

SUMMARY OF SEQUENCE LISTINGS

SEQ ID NO:1 is the amino acid sequence of ZmaN.
SEQ ID NO:2 is the amino acid sequence of ZmaD.
SEQ ID NO:3 is the amino acid sequence of ZmaE.
SEQ ID NO:4 is the amino acid sequence of ZmaG.
SEQ ID NO:5 is the amino acid sequence of ZmaA.
SEQ ID NO:6 is the amino acid sequence of ZmaF.
SEQ ID NO:7 is the amino acid sequence of the KS1 domain of ZmaA.
SEQ ID NO:8 is the amino acid sequence of the KR1 domain of ZmaA.
SEQ ID NO:9 is the amino acid sequence of the ACP1 domain of ZmaA.
SEQ ID NO:10 is the amino acid sequence of the KS2 domain of ZmaA.
SEQ ID NO:1 is the amino acid sequence of the AT domain of ZmaA.
SEQ ID NO:12 is the amino acid sequence of the KR2 domain of ZmaA.
SEQ ID NO:13 is the amino acid sequence of the ACP2 domain of ZmaA.
SEQ ID NO:14 is the amino acid sequence of the ZmaH site of post-translational modification by 4'-phosphopantetheinyl group.

What is claimed is:

1. A method for incorporating an aminomalonyl into a hybrid polyketide molecule, comprising adding and reacting aminomalonyl-acyl carrier protein (AM-ACP) in a cell-free system with (a) an isolated polypeptide comprising an amino acid sequence selected from the group consisting of the amino acid sequence of SEQ ID NO:6 and an amino acid sequence that is at least 95% identical to SEQ ID NO:6, wherein said isolated polypeptide has the biological activity of catalyzing the incorporation of an ethanolamine subunit from AM-ACP into a polyketide; and (b) a second isolated polypeptide comprising (i) an amino acid sequence selected from the group consisting of the amino acid sequence of SEQ ID NO:7 and an amino acid sequence that is at least 95% identical to SEQ ID NO:7, whereby the second isolated polypeptide has ketosynthase activity, (ii) an amino acid sequence selected from the group consisting of the amino acid sequence of SEQ ID NO:8, whereby the second isolated polypeptide has ketoreductase activity, and (iii) an amino acid sequence selected from the group consisting of the amino acid sequence of SEQ ID NO:9 and an amino acid sequence that is at least 95% identical to SEQ ID NO:9, whereby the second isolated polypeptide has acyl carrier protein activity, wherein said isolated polypeptides of (a) and (b) incorporate the aminomalonyl into the hybrid polyketide molecule.

2. The method of claim 1, further comprising expressing in a host cell a polynucleotide encoding each of the isolated polypeptides selected in (a) and (b) and subsequently isolating the polypeptides expressed by the host cell from the host cell to use in the cell-free system.

3. A method for incorporating an aminomalonyl into a hybrid polyketide molecule, comprising adding and reacting aminomalonyl-acyl carrier protein (AM-ACP) in a cell-free system with (a) an isolated polypeptide comprising an amino acid sequence selected from the group consisting of the amino acid sequence of SEQ ID NO:6 and an amino acid sequence that is at least 95% identical to SEQ ID NO:6, wherein said isolated polypeptide has the biological activity of catalyzing the incorporation of an ethanolamine subunit from AM-ACP into a polyketide; and (b) a second isolated polypeptide comprising an amino acid sequence selected from the group consisting of the amino acid sequence of SEQ ID NO:5 and an amino acid sequence that is at least 95% identical to SEQ ID NO:5, whereby the second isolated polypeptide has ketosynthase activity, ketoreductase activity, and acyl carrier protein activity, wherein said isolated polypeptides of (a) and (b) incorporate the aminomalonyl into the hybrid polyketide molecule.

4. The method of claim 3, further comprising expressing in a host cell a polynucleotide encoding each of the isolated polypeptides selected in (a) and (b) and subsequently isolating the polypeptides expressed by the host cell from the host cell to use in the cell free system.

5. A method for incorporating a hydroxymalonyl into a hybrid polyketide molecule, comprising adding and reacting hydroxymalonyl-acyl carrier protein (HM-ACP) in a cell-free system with an isolated polypeptide comprising (a) an amino acid sequence selected from the group consisting of the amino acid sequence of SEQ ID NO:10 and an amino acid sequence that is at least 95% identical to SEQ ID NO:10, (b) an amino acid sequence selected from the group consisting of the amino acid sequence of SEQ ID NO:11 and an amino acid sequence that is at least 95% identical to SEQ ID NO:11, whereby the isolated polypeptide has acyltransferase activity, (c) an amino acid sequence selected from the group consisting of the amino acid sequence of SEQ ID NO:12 and an amino acid sequence that is at least 95% identical to SEQ ID NO:12, whereby the isolated polypeptide has ketoreductase activity, and (d) an amino acid sequence selected from the group consisting of the amino acid sequence of SEQ ID NO:13 and an amino acid sequence that is at least 95% identical to SEQ ID NO:13, whereby the isolated polypeptide has acyl carrier protein activity, wherein said isolated polypeptide incorporates the hydroxymalonyl into the hybrid polyketide molecule.

6. The method of claim 5, further comprising expressing in a host cell a polynucleotide encoding the isolated polypeptide and subsequently isolating the polypeptide expressed by the host cell from the host cell to use in the cell free system.

7. A method for incorporating a hydroxymalonyl into a hybrid polyketide molecule comprising adding and reacting hydroxymalonyl-acyl carrier protein (HM-ACP) in a cell-free system with an isolated polypeptide comprising an amino acid sequence selected from the group consisting of the amino acid sequence of SEQ ID NO:5 and an amino acid sequence that is at least 95% identical to SEQ ID NO:5, wherein said isolated polypeptide has the biological activity of recognition, activation, and condensation of HM-ACP into a polyketide, wherein said isolated polypeptide incorporates the hydroxymalonyl into the hybrid polyketide molecule.

8. The method of claim 7, further comprising expressing in a host cell a polynucleotide encoding the isolated polypeptide and subsequently isolating the polypeptide expressed by the host cell from the host cell to use in the cell free system.

9. A method for incorporating an aminomalonyl into a hybrid polyketide molecule, comprising adding and reacting aminomalonyl-acyl carrier protein (AM-ACP) in a cell-free system with an isolated polypeptide comprising an amino acid sequence selected from the group consisting of the amino acid sequence of SEQ ID NO:6 and an amino acid sequence that is at least 95% identical to SEQ ID NO:6, wherein said isolated polypeptide has the biological activity of catalyzing the incorporation of an ethanolamine subunit from AM-ACP into a polyketide, wherein the aminomalonyl is incorporated into the hybrid polyketide molecule.

10. The method of claim 9, further comprising reacting the AM-ACP in the cell-free system with a second isolated polypeptide comprising one or more of (a) an amino acid sequence selected from the group consisting of the amino acid sequence of SEQ ID NO:7 and an amino acid sequence that is at least 95% identical to SEQ ID NO:7, whereby the second isolated polypeptide has ketosynthase activity; (b) an amino acid sequence selected from the group consisting of the amino acid sequence of SEQ ID NO:8 and an amino acid sequence that is at least 95% identical to SEQ ID NO:8, whereby the second isolated polypeptide has ketoreductase activity; and (c) an amino acid sequence selected from the group consisting of the amino acid sequence of SEQ ID NO:9 and an amino acid sequence that is at least 95% identical to SEQ ID NO:9, whereby the second isolated polypeptide has acyl carrier protein activity.

\* \* \* \* \*

UNITED STATES PATENT AND TRADEMARK OFFICE
CERTIFICATE OF CORRECTION

Page 1 of 1

PATENT NO. : 8,759,031 B2
APPLICATION NO. : 12/100150
DATED : June 24, 2014
INVENTOR(S) : Michael G. Thomas et al.

It is certified that error appears in the above-identified patent and that said Letters Patent is hereby corrected as shown below:

In the Specification:

Column 15, line 49 "27, 28, 29" should be -- 27, 28, 29, 30 --

In the Claims:

Column 69, line 33 "ID NO:8," should be -- "ID NO:8 and an amino acid sequence that is at least 95% identical to SEQ ID NO: 8, --

Signed and Sealed this
Fourteenth Day of October, 2014

Michelle K. Lee
*Deputy Director of the United States Patent and Trademark Office*